United States Patent
Belliotti et al.

(10) Patent No.: US 6,642,398 B2
(45) Date of Patent: Nov. 4, 2003

(54) MONO-AND DISUBSTITUTED 3-PROPYL GAMMA-AMINOBUTYRIC ACIDS

(75) Inventors: Thomas Richard Belliotti, Saline, MI (US); Justin Stephen Bryans, Balsham (GB); Ihoezo Victor Ekhato, West Chester, PA (US); Augustine Tobi Osuma, Ann Arbor, MI (US); Robert Michael Schelkun, Ypsilanti, MI (US); Jacob Bradley Schwarz, Ann Arbor, MI (US); Andrew John Thorpe, Ann Arbor, MI (US); Lawrence David Wise, Ann Arbor, MI (US); David Juergen Wustrow, Ann Arbor, MI (US); Po-Wai Yuen, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 23 days.

(21) Appl. No.: 10/324,929

(22) Filed: Dec. 20, 2002

(65) Prior Publication Data

US 2003/0181523 A1 Sep. 25, 2003

Related U.S. Application Data

(63) Continuation of application No. 10/009,938, filed as application No. PCT/US00/15070 on May 31, 2000, now abandoned.
(60) Provisional application No. 60/138,485, filed on Jun. 10, 1999.

(51) Int. Cl.[7] .............................................. C07D 10/00
(52) U.S. Cl. .................... 554/108; 554/103; 514/557; 514/558; 514/559; 514/560; 514/740; 514/741; 562/433; 562/512; 562/553; 564/453; 564/454; 564/463; 564/503; 564/509

(58) Field of Search .................................. 554/103, 108; 514/557, 558, 559, 560, 740, 741; 562/433, 512, 553; 564/453, 454, 463, 503, 504

(56) References Cited

U.S. PATENT DOCUMENTS 6,197,819 B1   3/2001   Silverman et al. .......... 514/561

FOREIGN PATENT DOCUMENTS

| WO | 9209560 | 6/1992 |
|----|---------|--------|
| WO | 9323383 | 11/1993 |
| WO | 9817627 | 4/1998 |
| WO | 9921824 | 5/1999 |

*Primary Examiner*—Deborah Carr
(74) *Attorney, Agent, or Firm*—Mehdi Ganjeizadeh; Karen DeBenedictis; Charles Ashbrook

(57) ABSTRACT

The instant invention is a series of novel mono- and disubstituted 3-propyl gamma aminobutyric acids of Formula I

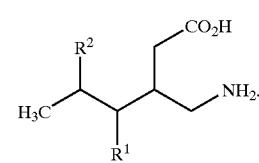

The compounds are useful as therapeutic agents in the treatment of epilepsy, faintness attacks, hypokinesia, cranial disorders, neurodegenerative disorders, depression, anxiety, panic, pain, neuropathological disorders, arthritis, sleep disorders, IBS, and gastric damage. Methods of preparing the compounds and useful intermediates are also part of the invention.

28 Claims, No Drawings

MONO- AND DISUBSTITUTED 3-PROPYL GAMMA-AMINOBUTYRIC ACIDS

This application is a continuation of U.S. application Ser. No. 10/009,938 filed Dec. 10, 2001, which is a §371 filing of PCT/US00/15070 filed May 31, 2000, now abandoned which claims the benefit of U.S. Provisional Application 60/138,485 filed Jun. 10, 1999; the entire contents of each of which are hereby incorporated herein by reference.

BACKGROUND OF THE INVENTION

Compounds of formula

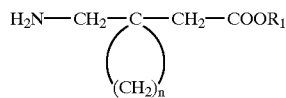

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

Compounds of formula

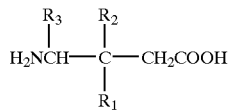

or a pharmaceutically acceptable salt thereof wherein $R_1$ is a straight or branched alkyl group having from 1 to 6 carbon atoms, phenyl or cycloalkyl having from 3 to 6 carbon atoms; $R_2$ is hydrogen or methyl; and $R_3$ is hydrogen, or carboxyl are known in U.S. Pat. No. 5,563,175 and its various divisionals. These patents are hereby incorporated by reference.

SUMMARY OF THE INVENTION

The compounds of the instant invention are those of Formula I

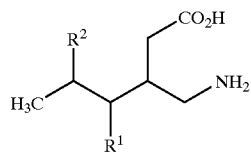

or a pharmaceutically acceptable salt thereof wherein:
$R^1$ is hydrogen, straight or branched alkyl of from 1 to 6 carbon atoms or phenyl;
$R^2$ is straight or branched alkyl of from 1 to 8 carbon atoms,
straight or branched alkenyl of from 2 to 8 carbon atoms,
cycloalkyl of from 3 to 7 carbon atoms,
alkoxy of from 1 to 6 carbon atoms,
alkylcycloalkyl,
alkylalkoxy,
alkyl OH
alkylphenyl,
alkylphenoxy,
phenyl or substituted phenyl; and
$R^1$ is straight or branched alkyl of from 1 to 6 carbon atoms or phenyl when $R^2$ is methyl.

Preferred compounds are those of Formula I wherein $R^1$ is hydrogen, and $R^2$ is alkyl.

Other preferred compounds are those of Formula I wherein $R^1$ is methyl, and $R^2$ is alkyl.

Still other preferred compounds are those of Formula I wherein $R^1$ is methyl, and $R^2$ is methyl or ethyl.

Especially preferred compounds are selected from:

3-Aminomethyl-5-methylheptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5-methyl-dodecanoic acid;
3-Aminomethyl-5-methyl-tridecanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-trifluoromethyl-hexanoic acid;
3-Aminomethyl-5-phenyl-hexanoic acid;
3-Aminomethyl-5-(2-chlorophenyl)-hexanoic acid;
3-Aminomethyl-5-(3-chlorophenyl)-hexanoic acid;
3-Aminomethyl-5-(4-chlorophenyl)-hexanoic acid;
3-Aminomethyl-5-(2-methoxyphenyl)-hexanoic acid;
3-Aminomethyl-5-(3-methoxyphenyl)-hexanoic acid;
3-Aminomethyl-5-(4-methoxyphenyl)-hexanoic acid; and
3-Aminomethyl-5-(phenylmethyl)-hexanoic acid.

Other especially preferred compounds are selected from:

(3R,4S)-3-Aminomethyl-4,5-dimethyl-hexanoic acid;
3-Aminomethyl-4,5-dimethyl-hexanoic acid;
(3R,4S)-3-Aminomethyl-4,5-dimethyl-hexanoic acid MP;
(3S,4S)-3-Aminomethyl-4,5-dimethyl-hexanoic acid;
(3R,4R)-3-Aminomethyl-4,5-dimethyl-hexanoic acid MP;
3-Aminomethyl-4-isopropyl-hexanoic acid;
3-Aminomethyl-4-isopropyl-heptanoic acid;
3-Aminomethyl-4-isopropyl-octanoic acid;
3-Aminomethyl-4-isopropyl-nonanoic acid;
3-Aminomethyl-4-isopropyl-decanoic acid; and
3-Aminomethyl-4-phenyl-5-methyl-hexanoic acid.

Other preferred compounds are selected from (3S,5S)-3-Aminomethyl-5-methoxy-hexanoic acid;
(3S,5S)-3-Aminomethyl-5-ethoxy-hexanoic acid;
(3S,5S)-3-Aminomethyl-5-propoxy-hexanoic acid;
(3S,5S)-3-Aminomethyl-5-isopropoxy-hexanoic acid;
(3S,5S)-3-Aminomethyl-5-tert-butoxy-hexanoic acid;
(3S,5S)-3-Aminomethyl-5-fluoromethoxy-hexanoic acid;
(3S,5S)-3-Aminomethyl-5-(2-fluoro-ethoxy)-hexanoic acid;
(3S,5S)-3-Aminomethyl-5-(3,3,3-trifluoro-propoxy)-hexanoic acid;
(3S,5S)-3-Aminomethyl-5-phenoxy-hexanoic acid;
(3S,5S)-3-Aminomethyl-5-(4-chloro-phenoxy)-hexanoic acid;
(3S,5S)-3-Aminomethyl-5-(3-chloro-phenoxy)-hexanoic acid;
(3S,5S)-3-Aminomethyl-5-(2-chloro-phenoxy)-hexanoic acid;

(3S,5S)-3-Aminomethyl-5-(4-fluoro-phenoxy)-hexanoic acid;
(3S,5S)-3-Aminomethyl-5-(3-fluoro-phenoxy)-hexanoic acid;
(3S,5S)-3-Aminomethyl-5-(2-fluoro-phenoxy)-hexanoic acid;
(3S,5S)-3-Aminomethyl-5-(4-methoxy-phenoxy)-hexanoic acid;
(3S,5S)-3-Aminomethyl-5-(3-methoxy-phenoxy)-hexanoic acid;
(3S,5S)-3-Aminomethyl-5-(2-methoxy-phenoxy)-hexanoic acid;
(3S,5S)-3-Aminomethyl-5-(4-nitro-phenoxy)-hexanoic acid;
(3S,5S)-3-Aminomethyl-5-(3-nitro-phenoxy)-hexanoic acid;
(3S,5S)-3-Aminomethyl-5-(2-nitro-phenoxy)-hexanoic acid;
(3S,5S)-3-Aminomethyl-6-hydroxy-5-methyl-hexanoic acid;
(3S,5S)-3-Aminomethyl-6-methoxy-5-methyl-hexanoic acid;
(3S,5S)-3-Aminomethyl-6-ethoxy-5-methyl-hexanoic acid;
(3S,5S)-3-Aminomethyl-5-methyl-6-propoxy-hexanoic acid;
(3S,5S)-3-Aminomethyl-6-isopropoxy-5-methyl-hexanoic acid;
(3S,5S)-3-Aminomethyl-6-tert-butoxy-5-methyl-hexanoic acid;
(3S,5S)-3-Aminomethyl-6-fluoromethoxy-5-methyl-hexanoic acid;
(3S,5S)-3-Aminomethyl-6-(2-fluoro-ethoxy)-5-methyl-hexanoic acid;
(3S,5S)-3-Aminomethyl-5-methyl-6-(3,3,3-trifluoro-propoxy)-hexanoic acid;
(3S,5S)-3-Aminomethyl-5-methyl-6-phenoxy-hexanoic acid;
(3S,5S)-3-Aminomethyl-6-(4-chloro-phenoxy)-5-methyl-hexanoic acid;
(3S,5S)-3-Aminomethyl-6-(3-chloro-phenoxy)-5-methyl-hexanoic acid;
(3S,5S)-3-Aminomethyl-6-(2-chloro-phenoxy)-5-methyl-hexanoic acid;
(3S,5S)-3-Aminomethyl-6-(4-fluoro-phenoxy)-5-methyl-hexanoic acid;
(3S,5S)-3-Aminomethyl-6-(3-fluoro-phenoxy)-5-methyl-hexanoic acid;
(3S,5S)-3-Aminomethyl-6-(2-fluoro-phenoxy)-5-methyl-hexanoic acid;
(3S,5S)-3-Aminomethyl-6-(4-methoxy-phenoxy)-5-methyl-hexanoic acid;
(3S,5S)-3-Aminomethyl-6-(3-methoxy-phenoxy)-5-methyl-hexanoic acid;
(3S,5S)-3-Aminomethyl-6-(2-methoxy-phenoxy)-5-methyl-hexanoic acid;
(3S,5S)-3-Aminomethyl-5-methyl 6-(4-trifluoromethyl-phenoxy)-hexanoic acid;
(3S,5S)-3-Aminomethyl-5-methyl 6-(3-trifluoromethyl-phenoxy)-hexanoic acid;
(3S,5S)-3-Aminomethyl-5-methyl 6-(2-trifluoromethyl-phenoxy)-hexanoic acid;
(3S,5S)-3-Aminomethyl-5-methyl 6-(4-nitro-phenoxy)-hexanoic acid;
(3S,5S)-3-Aminomethyl-5-methyl 6-(3-nitro-phenoxy)-hexanoic acid;
(3S,5S)-3-Aminomethyl-5-methyl 6-(2-nitro-phenoxy)-hexanoic acid;
(3S,5S)-3-Aminomethyl-6-benzyloxy-5-methyl-hexanoic acid;
(3S,5S)-3-Aminomethyl-7-hydroxy-5-methyl-heptanoic acid;
(3S,5S)-3-Aminomethyl-7-methoxy-5-methyl-heptanoic acid;
(3S,5S)-3-Aminomethyl-7-ethoxy-5-methyl-heptanoic acid;
(3S,5S)-3-Aminomethyl-5-methyl-7-propoxy-heptanoic acid;
(3S,5S)-3-Aminomethyl-7-isopropoxy-5-methyl-heptanoic acid;
(3S,5S)-3-Aminomethyl-7-tert-butoxy-5-methyl-heptanoic acid;
(3S,5S)-3-Aminomethyl-7-fluoromethoxy-5-methyl-heptanoic acid;
(3S,5S)-3-Aminomethyl-7-(2-fluoro-ethoxy)-5-methyl-heptanoic acid;
(3S,5S)-3-Aminomethyl-5-methyl-7-(3,3,3-trifluoro-propoxy)-heptanoic acid;
(3S,5S)-3-Aminomethyl-7-benzyloxy-5-methyl-heptanoic acid;
(3S,5S)-3-Aminomethyl-5-methyl-7-phenoxy-heptanoic acid;
(3S,5S)-3-Aminomethyl-7-(4-chloro-phenoxy)-5-methyl-heptanoic acid;
(3S,5S)-3-Aminomethyl-7-(3-chloro-phenoxy)-5-methyl-heptanoic acid;
(3S,5S)-3-Aminomethyl-7-(2-chloro-phenoxy)-5-methyl-heptanoic acid;
(3S,5S)-3-Aminomethyl-7-(4-fluoro-phenoxy)-5-methyl-heptanoic acid;
(3S,5S)-3-Aminomethyl-7-(3-fluoro-phenoxy)-5-methyl-heptanoic acid;
(3S,5S)-3-Aminomethyl-7-(2-fluoro-phenoxy)-5-methyl-heptanoic acid;
(3S,5S)-3-Aminomethyl-7-(4-methoxy-phenoxy)-5-methyl-heptanoic acid;
(3S,5S)-3-Aminomethyl-7-(3-methoxy-phenoxy)-5-methyl-heptanoic acid;
(3S,5S)-3-Aminomethyl-7-(2-methoxy-phenoxy)-5-methyl-heptanoic acid;
(3S,5S)-3-Aminomethyl-5-methyl-7-(4-trifluoromethyl-phenoxy)-heptanoic acid;
(3S,5S)-3-Aminomethyl-5-methyl-7-(3-trifluoromethyl-phenoxy)-heptanoic acid;
(3S,5S)-3-Aminomethyl-5-methyl-7-(2-trifluoromethyl-phenoxy)-heptanoic acid;
(3S,5S)-3-Aminomethyl-5-methyl-7-(4-nitro-phenoxy)-heptanoic acid;
(3S,5S)-3-Aminomethyl-5-methyl-7-(3-nitro-phenoxy)-heptanoic acid;
(3S,5S)-3-Aminomethyl-5-methyl-7-(2-nitro-phenoxy)-heptanoic acid;
(3S,5S)-3-Aminomethyl-5-methyl-6-phenyl-hexanoic acid;
(3S,5S)-3-Aminomethyl-6-(4-chloro-phenyl)-5-methyl-hexanoic acid;
(3S,5S)-3-Aminomethyl-6-(3-chloro-phenyl)-5-methyl-hexanoic acid;
(3S,5S)-3-Aminomethyl-6-(2-chloro-phenyl)-5-methyl-hexanoic acid;
(3S,5S)-3-Aminomethyl-6-(4-methoxy-phenyl)-5-methyl-hexanoic acid;
(3S,5S)-3-Aminomethyl-6-(3-methoxy-phenyl)-5-methyl-hexanoic acid;
(3S,5S)-3-Aminomethyl-6-(2-methoxy-phenyl)-5-methyl-hexanoic acid;
(3S,5S)-3-Aminomethyl-6-(4-fluoro-phenyl)-5-methyl-hexanoic acid;

(3S,5S)-3-Aminomethyl-6-(3-fluoro-phenyl)-5-methyl-hexanoic acid;
(3S,5S)-3-Aminomethyl-6-(2-fluoro-phenyl)-5-methyl-hexanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid;
(3S,5R)-3-Aminomethyl-5-methyl-oct-7-enoic acid;
(3S,5R)-3-Aminomethyl-5-methyl-non-8-enoic acid;
(E)-(3S,5S)-3-Aminomethyl-5-methyl-oct-6-enoic acid;
(Z)-(3S,5S)-3-Aminomethyl-5-methyl-oct-6-enoic acid;
(Z)-(3S,5S)-3-Aminomethyl-5-methyl-non-6-enoic acid;
(E)-(3S,5S)-3-Aminomethyl-5-methyl-non-6-enoic acid;
(E)-(3S,5R)-3-Aminomethyl-5-methyl-non-7-enoic acid;
(Z)-(3S,5R)-3-Aminomethyl-5-methyl-non-7-enoic acid;
(Z)-(3S,5R)-3-Aminomethyl-5-methyl-dec-7-enoic acid;
(E)-(3S,5R)-3-Aminomethyl-5-methyl-undec-7-enoic acid;
(3S,5S)-3-Aminomethyl-5,6,6-trimethyl-heptanoic acid;
(3S,5S)-3-Aminomethyl-5,6-dimethyl-heptanoic acid;
(3S,5S)-3-Aminomethyl-5-cyclopropyl-hexanoic acid;
(3S,5S)-3-Aminomethyl-5-cyclobutyl-hexanoic acid;
(3S,5S)-3-Aminomethyl-5-cyclopentyl-hexanoic acid; and
(3S,5S)-3-Aminomethyl-5-cyclohexyl-hexanoic acid.

Still other more preferred compounds are:

(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5-methyl-dodecanoic acid;
(3S,5R)-3-Aminomethyl-5,9-dimethyl-decanoic acid;
(3S,5R)-3-Aminomethyl-5,7-dimethyl-octanoic acid;
(3S,5R)-3-Aminomethyl-5,8-dimethyl-nonanoic acid;
(3S,5R)-3-Aminomethyl-6-cyclopropyl-5-methyl-hexanoic acid;
(3S,5R)-3-Aminomethyl-6-cyclobutyl-5-methyl-hexanoic acid;
(3S,5R)-3-Aminomethyl-6-cyclopentyl-5-methyl-hexanoic acid;
(3S,5R)-3-Aminomethyl-6-cyclohexyl-5-methyl-hexanoic acid;
(3S,5R)-3-Aminomethyl-7-cyclopropyl-5-methyl-heptanoic acid;
(3S,5R)-3-Aminomethyl-7-cyclobutyl-5-methyl-heptanoic acid;
(3S,5R)-3-Aminomethyl-7-cyclopentyl-5-methyl-heptanoic acid;
(3S,5R)-3-Aminomethyl-7-cyclohexyl-5-methyl-heptanoic acid;
(3S,5R)-3-Aminomethyl-8-cyclopropyl-5-methyl-octanoic acid;
(3S,5R)-3-Aminomethyl-8-cyclobutyl-5-methyl-octanoic acid;
(3S,5R)-3-Aminomethyl-8-cyclopentyl-5-methyl-octanoic acid;
(3S,5R)-3-Aminomethyl-8-cyclohexyl-5-methyl-octanoic acid;
(3S,5S)-3-Aminomethyl-6-fluoro-5-methyl-hexanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5R)-3-Aminomethyl-9-fluoro-5-methyl-nonanoic acid;
(3S,5S)-3-Aminomethyl-7,7,7-trifluoro-5-methyl-heptanoic acid;
(3S,5R)-3-Aminomethyl-8,8,8-trifluoro-5-methyl-octanoic acid;
(3S,5R)-3-Aminomethyl-5-methyl-8-phenyl-octanoic acid;
(3S,5S)-3-Aminomethyl-5-methyl-6-phenyl-hexanoic acid; and
(3S,5R)-3-Aminomethyl-5-methyl-7-phenyl-heptanoic acid.

The invention is also a pharmaceutical composition comprising a therapeutically effective amount of one or more compounds of Formula I and a pharmaceutically acceptable carrier.

The compounds of the invention are useful in the treatment of epilepsy, faintness attacks, hypokinesia, cranial disorders, neurodegenerative disorders, depression, anxiety, panic, pain, neuropathological disorders, arthritis, sleep disorders, irritable bowel syndrome (IBS), and gastric damage.

DETAILED DESCRIPTION OF THE INVENTION

The compounds of the instant invention are mono- and disubstituted 3-propyl gamma-aminobutyric acids as shown in Formula I above.

The terms are as described below or as they occur in the specification.

The term alkyl or alkenyl is a straight or branched group of from 1 to 8 carbon atoms or 2 to 8 carbon atoms including but not limited to methyl, ethyl, propyl, n-propyl, isopropyl, butyl, 2-butyl, tert-butyl, and octyl. Alkyl can be unsubstituted or substituted by from 1 to 3 fluorine atoms. Preferred groups are methyl and ethyl.

Cycloalkyl is a cyclic group of from 3 to 7 carbon atoms.

The benzyl and phenyl groups may be unsubstituted or substituted with from 1 to 3 groups each independents selected from halogen, especially fluoro, alkoxy, alkyl, and amino.

Halogen includes fluorine, chlorine, bromine, and iodine.

Alkoxy is as described above for alkyl.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion.

Prodrugs of compounds I–VIII are included in the scope of the instant invention. Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990;15(4):361–368). The last two citations are hereby incorporated by reference.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug which has been chemically modified and may be biologically inactive at its site of action, but which may be degraded or modified by one or more enzymatic or other in vivo processes to the parent bioactive form.

This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

2) peptides which may be recognized by specific or nonspecific proteinases. A peptide may be coupled to the drug molecule via amide bond formation with the amine or carboxylic acid moiety of the drug molecule by known means.

3) derivatives that accumulate at a site of action through membrane selection of a prodrug form or modified prodrug form, 4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., $R-N^+(CH_3)_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention includes all enantiomeric and epimeric forms as well as the appropriate mixtures thereof. For example, the compound of Example 1 is a mixture of all four possible stereoisomers. The compound of Example 6 is one of the isomers. The configuration of the cyclohexane ring carbon centers may be R or S in these compounds where a configuration can be defined.

The radioligand binding assay using [$^3$H]gabapentin and the $\alpha_2\delta$ subunit derived from porcine brain tissue was used (Gee N. S., Brown J. P., Dissanayake V. U. K., Offord J., Thurlow R., Woodruff G. N., "The Novel Anti-convulsant Drug, Gabapentin, Binds to the $\alpha_2\delta$ Subunit of a Calcium Channel," *J. Biol. Chem.*, 1996;271:5879–5776).

TABLE 1

| Structure | [$^3$H] GBP Binding (IC$_{50}$, nM) | Anticonvulsant % Protect | |
|---|---|---|---|
| | | 1 hr | 2 hr |
| ![structure] CO$_2$H, NH$_2$ | 0.218 | | 100 |
| ![structure] CO$_2$H, NH$_2$ | 1.8 | 0 | 0 |
| ![structure] CO$_2$H, NH$_2$ | 0.04 | 80 | 100 |
| ![structure] CO$_2$H, NH$_2$ | 0.206 | 0 | 20 |
| ![structure] CO$_2$H, NH$_2$ | On test | 0 | 20 |
| ![structure] CO$_2$H, NH$_2$ | 0.092 | 60 | 100 |

Table 1 above shows the binding affinity of the compounds of the invention to the $\alpha_2\delta$ subunit.

The compounds of the invention are compared to Neurontin®, a marketed drug effective in the treatment of such disorders as epilepsy. Neurontin® is 1-(aminomethyl)-cyclohexaneacetic acid of structural formula

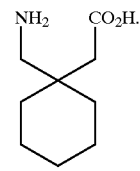

Gabapentin (Neurontin®) is about 0.10 to 0.12 μM in this assay. The compounds of the instant invention are expected, therefore, to exhibit pharmacologic properties comparable to or better than gabapentin. For example, as agents for convulsions, anxiety, and pain.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

The compounds of the invention are also expected to be useful in the treatment of sleep disorders. Sleep disorders are disturbances that affect the ability to fall and/or stay asleep, that involves sleeping to much, or that result in abnormal behavior associated with sleep. The disorders include, for example, insomnia, drug-associated sleeplessness, hypersomnia, narcolepsy, sleep apnea syndromes, and parasomnias.

The compounds of the invention are also useful in the treatment of arthritis.

Biological Activity

TABLE 2

| Example | [$^3$H] GBP Binding (IC$_{50}$, $\mu$M) | Anxiolytic Activity* % Preg. Act. | Anticonvulsant % Protect* 1 h | 2 h |
|---|---|---|---|---|
| Pregabalin | 0.218 | 100 | | 100 |
| (3S,4R)3-Aminomethyl 4,5-dimethyl-hexanoic acid | 2.2 | 12 | 20 | 20 |
| (3R,4S)3-Aminomethyl-4,5-dimethyl-hexanoic acid | 1.7 | 58 | 20 | 0 |
| (3R,4R)3-Aminomethyl-4,5-dimethyl-hexanoic acid | 0.022 | 204 | 100 | 100 |
| 3-Aminomethyl-5-methylheptanoic acid | 0.092 | 79 | 60 | 100 |
| 3-Aminomethyl-5-methyloctanoic acid | 0.019 | NT | 40 | 100 |
| 3-Aminomethyl-5-methyldecanoic acid | 0.150 | NT | 0 | 0 |
| 3-Aminomethyl-5-methylnonanoic acid | 0.178 | NT | 40 | 80 |

TABLE 2-continued

| Example | [³H] GBP Binding (IC$_{50}$, μM) | Anxiolytic Activity* % Preg. Act. | Anticonvulsant % Protect* 1 h | 2 h |
|---|---|---|---|---|
| 3-Aminomethyl-5-methylundecanoic acid | 0.163 | NT | NT | |
| (3S,5R)-3-Aminomethyl-5-methyl-heptanoic acid | On test | On test | 80 | 100 |
| (3S,5R)-3-Aminomethyl-5-methyl-octanoic acid hydrochloride | 0.012 | 160 | 100 | 100 |
| (3S,5R)-3-Aminomethyl-5-methyl-nonanoic acid hydrochloride | 0.026 | 125.94 | 100 | 100 |
| (3S,5R)-3-Aminomethyl-5-methyl-decanoic acid | 0.0297 | 105.59 | 100 | 100 |
| (3S,5S)-3-Aminomethyl-5-methyl-heptanoic acid | On test | On test | 0 | 0 |
| (3S,5S)-3-Aminomethyl-5-methyl-octanoic acid | 1.2 | 15.6 | 0 | 20 |
| (3S,5S)-3-Aminomethyl-5-methyl-nonanoic acid | On test | On test | 0 | 0 |
| 3-Aminomethyl-5-methyl-6-phenyl-hexanoic acid | 9.08 | NT | 0 | 0 |
| 3-Aminomethyl-5,7,7-trimethyl-octanoic acid | >10 | NT | NT | |
| (S)-3-Aminomethyl-5-methyl-octanoic acid | 0.0126 | 135.38 | 100 | 100 |
| 3-Aminomethyl-5,7-dimethyl-octanoic acid | 0.359 | NT | NT | |
| 3-Aminomethyl-6,6,6-trifluoro-5-methyl-hexanoic acid | 4.69 | NT | 0 | 0 |
| 3-Aminomethyl-5-methyl-oct-7-enoic acid | >10 | NT | 0 | 0 |
| (S)-3-Aminomethyl-6-methoxy-5-methyl-hexanoic acid | On test | On test | 0 | 0 |
| 3-aminomethyl-4-isopropyl-heptanoic acid | 0.671 | NT | NT | |
| 3-aminomethyl-4-isopropyl-octanoic acid | 5.4 | NT | 0 | 0 |
| 3-aminomethyl-4-isopropyl-hexanoic acid | 0.49 | NT | 0 | 0 |
| 3-Aminomethyl-5-methyl-4-phenyl-hexanoic acid | | NT | 0 | 0 |
| (S)-3-Aminomethyl-6-fluoro-5-methyl-hexanoic acid | 0.605 | NT | NT | |
| 3-Aminomethyl-5-cyclohexyl-hexanoic acid | 7.3 | NT | NT | |
| 3-Aminomethyl-5-cyclopentyl-hexanoic acid | >10 | | | |
| 3-Aminomethyl-5-phenyl-hexanoic acid | 10.1 | NT | NT | |
| (3S,5S)-3-Aminomethyl-5-methyl-decanoic acid | On test | On test | 0 | 20 |

*Compounds dosed at 30 mg/kg PO
NT is not tested.

The compounds of the instant invention are useful as anxiolytics and anticonvulsants as shown in Table 2 above. They are compared to pregabalin which is isobutylgaba or (S)-3-(Aminomethyl)-5-methylhexanoic acid of formula

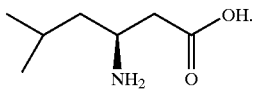

Material and Methods
Carrageenin-Induced Hyperalgesia

Nociceptive pressure thresholds were measured in the rat paw pressure test using an analgesimeter (Randall-Selitto method: Randall L. O. and Selitto J. J., "A method for measurement of analgesic activity on inflamed tissue," Arch. Int. Pharmacodyn., 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 μL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg, s.c.), morphine (3 mg/kg, s.c.) or saline at 3.5 hours after carrageenin and nociceptive thresholds were examined at 4, 4.5, and 5 hours postcarrageenin.

(R)-2-Aza-spiro[4.5]decane-4-carboxylic acid hydrochloride was tested in the above carrageenan-induced hyperalgesia model. The compound was dosed orally at 30 mg/kg, and 1 hour postdose gave a percent of maximum possible effect (MPE) of 53%. At 2 hours postdose, it gave only 4.6% of MPE.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., "Exploration of mice in a black and white box: validation as a model of anxiety," Pharmacol. Biochem. Behav., 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., "Effects of anxiolytic and anxiogenic drugs on exploratory activity in a simple model of anxiety in mice," Neuropharmacol., 1989;28:901–905).

Rat Elevated X-Maze

A standard elevated X-maze (Handley S. L., et al., "Effects of alpha-adrenoceptor agonists and antagonists in a maze-exploration model of 'fear'-motivated behavior," Naunyn-Schiedeberg's Arch. Pharmacol., 1984;327:1–5), was automated as previously described (Field, et al., "Automation of the rat elevated X-maze test of anxiety," Br. J. Pharmacol., 1991;102(Suppl.):304P). The animals are placed on the center of the X-maze facing one of the open arms. For determining anxiolytic effects the entries and time spent on the end half sections of the open arms is measured during the 5-minute test period (Costall, et al., "Use of the elevated plus maze to assess anxiolytic potential in the rat," Br. J. Pharmacol., 1989;96(Suppl.):312p).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

DBA2 Mouse Model of Anticonvulsant Efficacy

All procedures were carried out in compliance with the NIH Guide for the Care and Use of Laboratory Animals under a protocol approved by the Parke-Davis Animal Use Committee. Male DBA/2 mice, 3 to 4 weeks old were obtained from Jackson Laboratories, Bar Harbour, Me. Immediately before anticonvulsant testing, mice were placed upon a wire mesh, 4 inches square, suspended from a steel rod. The square was slowly inverted through 180° and mice observed for 30 seconds. Any mouse falling from the wire mesh was scored as ataxic (Coughenour L. L., McLean J. R., Parker R. B., "A new device for the rapid measurement of impaired motor function in mice," Pharm. Biochem. Behav., 1977;6(3):351–3). Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds. The incidence of all the seizure phases in the drug-treated and vehicle-treated mice was recorded, and the occurrence of tonic seizures were used for calculating anticonvulsant $ED_{50}$ values by probit analysis (Litchfield J. T., Wilcoxon F. "A simplified method for evaluating dose-effect experiments," J. Pharmacol., 1949;96:99–113). Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. Compounds that are insoluble will be suspended in 1% carboxymethocellulose. Doses are expressed as weight of the active drug moiety.

The compounds of the instant invention are also expected to be useful in the treatment of pain and phobic disorders (Am. J. Pain Manag., 1995;5:7–9).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

The compounds of the invention are also expected to be useful in sleep disorders. The assessment is as described in Drug Dev Res 1988;14:151–159.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

General Synthetic Schemes

Generic Description

Method 1

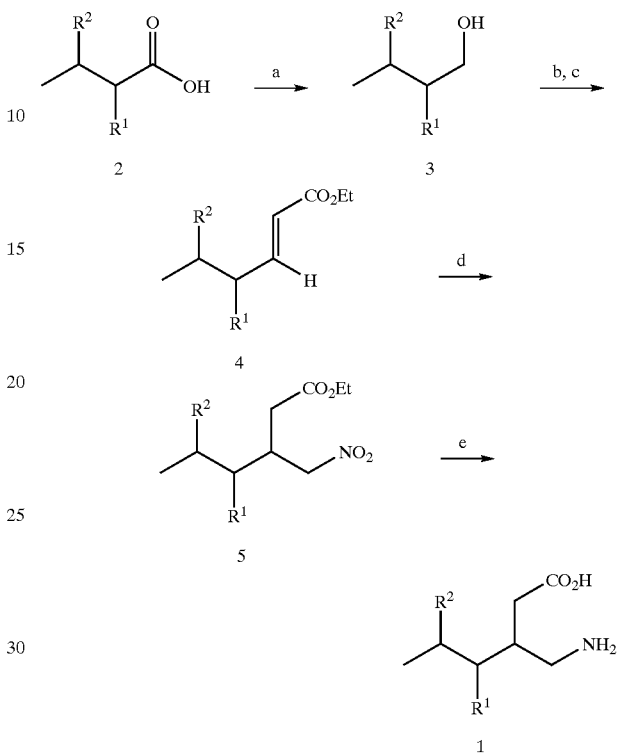

a) LiAlH$_4$;
b) pyridinium dichormate;
c) triethylphosphonoacetate, NaH;
d) Nitromethane DBU;
e) i. H2 Pd/C; ii. HCl; iii ion exchange chromatography.

Method 2

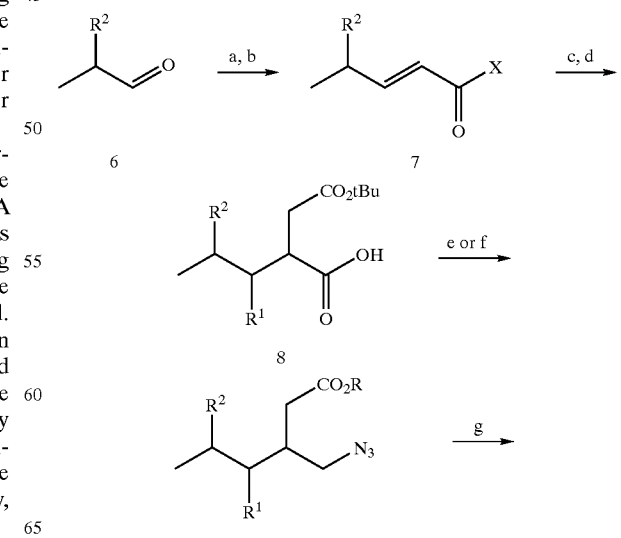

-continued

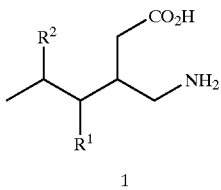

X=OEt or chiral oxazolidine auxiliary.
a) Triethylphosphonoacetate, NaH;
b) i. NaOH, ii. Pivaloyl chloride, Et$_3$N, XH;
c) R$^1$MgBr, CuBr$_2$ DMS;
d) NaHMDS, BrCH$_2$CO$_2$tBu;
e) R=tBu i. LiOH, H$_2$O$_2$; ii. BH$_3$, iii. TsCl, ET$_3$N, iv. NaN$_3$, DMSO;
f) R=Et i. LiOH, H$_2$O$_2$; ii. BH$_3$, iii. PTSA, THF; iv HBr EtOH, v. NaN$_3$ DMSO;
g) i. H$_2$ Pd/C; ii. HCl, iii. Ion exchange chromatography.

Specific Examples
Synthesis of Example 1
3-Aminomethyl-5-methylheptanoic acid

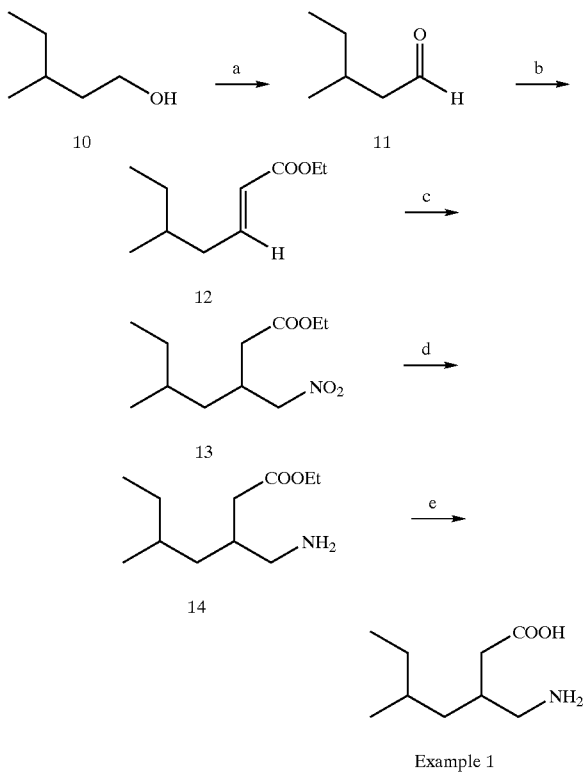

a) PDC, CH$_2$Cl$_2$;
b) NaH, triethylphosphonoacetate;
c) DBU, CH$_3$NO$_2$;
d) H$_2$, 10% Pd/C;
e) 6N HCl, reflux, ion exchange resin (Dowex 50WX8, strongly acidic).

3-Methyl-1-pentanal 11

To a stirred suspension of pyridinum dichromate (112.17 g, 298.1 mmol) in dichloromethane 500 mL was added 3-methyl-1-pentanol 10 (15 g, 146.79 mmol). After stirring for 2.5 hours, ether 400 mL was added, and stirring was continued for another 5 minutes. The filtrate from the mixture was concentrated to a small volume and applied to a column of Florisil. The compound was eluted with petroleum ether, and further chromatographed on silica gel column using 10% ether in petroleum ether as eluent gave 11 (6.5 g, 44%). $^1$H-NMR (CDCl$_3$) δ9.72, (d, —C$\underline{H}$O), 2.38 (dd, 1H, —C$\underline{H}_2$CHO), 2.19 (dd, 1H, —C$\underline{H}_2$CHO), 1.95 (m, 1H, C$_2$H$_5$(CH$_3$)C$\underline{H}$CH$_2$—), 1.4–1.0 (m), 0.9–0.8 (m).

Ethyl 5-methyl-2-heptenoate 12

Sodium hydride (60% dispersion, 2.4 g, 65 mmol) was washed with hexane and suspended in dimethoxyethane 60 mL. While cooling in ice water bath triethyl phosphonoacetate was slowly added, calcd. 5 minutes. The reaction was stirred for 15 minutes at 0° C. and a solution of 3-methyl-1-pentanal 11 (6.5 g, 65 mmol) in imethoxyethane 20 mL was added. After refluxing overnight, it was concentrated, water and hexane were added, the organic phase was separated, and the aqueous portion discarded. The solution was washed twice with brine and dried on magnesium sulfate. The solvent was evaporated to give 12 (6.75 g, 61%). $^1$H-NMR (CDCl$_3$) δ6.89 (m, 1H, —CH$_2$C$\underline{H}$:CHCOOEt), 5.77 (d, 1H, —CH$_2$CH:C$\underline{H}$COOEt), 4.16 (q, 2H, —COOC$\underline{H}_2$CH$_3$), 2.15 and 1.98 (1H each and a multiplet, —C$\underline{H}_2$CH:CHCOOEt), 1.48 (m, 1H, C$_2$H$_5$(CH$_3$)C$\underline{H}$CH$_2$), 1.30–1.10 (m), and 0.83.

Ethyl 5-methyl-3-nitromethylheptanoate 13

Ethyl 5-methyl-2-heptenoate 12 (6.75 g, 39.70 mmol), DBU (6.0 g, 39.7 mmol), nitromethane (21.97 g, 359.9 mmol) in acetonitrile 80 mL was stirred at room temperature under nitrogen atmosphere overnight. The mixture was concentrated to an oil. A solution of the oil in ether was washed with 1N HCl, brine and dried. It was evaporated to give a light oil which was chromatographed on silica gel, eluting with 5% to 10% ether in Pet. ether to give 13 (3.6 g, 42%). $^1$H-NMR (CDCl$_3$) δ4.49–4.39 (m), 4.12–4.07 (m), 3.61 (m), 2.36 (m), 1.36–1.18 (m), 0.86–0.79.

3-Aminomethyl-5-methylheptanoic acid (Example 1)

Ethyl 5-methyl-3-nitromethylheptanoate 13 (3.6 g) was hydrogenated in ethanol in the presence of 20% Pd/C and evaporated to give 14. Six normal hydrochloric acid 30 mL was added and refluxed overnight. The solvent was evaporated at reduced pressure, and the residue was azeotroped with toluene. Aqueous solution of the residue was applied to Dowex 50WX 8-100 ion exchange resin that had been washed to neutral pH with HPLC grade water. The column was eluted with water until eluent was neutral pH, and then with 0.5N. NH$_4$OH solution to give factions containing 3-aminomethyl-5-methylheptanoic acid. The fractions were combined and further chromatographed on a C$_{18}$ column. The compound was eluted with 40% water in methanol and crystallized from methanol-ether to give Example 1 630 mg. $^1$H-NMR (CD$_3$OD) δ2.83 (m, 1H), 2.75 (m, 1H), 2.35 (m, 1H), 2.15 (m, 1H), 1.95 (1H, bs), 1.38 (1H, m), 1.3–1.15 (m, 2H), 1.14–0.95 (m, 2H). 0.80 (m, 2CH$_3$). MS found molecular ion at (M+1) 174 and other ions at 156, 139, and 102. Anal. Calcd. for C$_9$H$_{19}$NO$_2$: C, 62.39; H, 11.05; N, 8.08. Found C, 62.00; H, 10.83; N, 7.98.

In a similar way the following examples can be prepared.

3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5-methyl-dodecanoic acid;
3-Aminomethyl-5-methyl-tridecanoic acid;
3-Aminomethyl-5-cyclopropyl-hexanoic acid;

3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-trifluoromethyl-hexanoic acid;
3-Aminomethyl-5-phenyl-hexanoic acid;
3-Aminomethyl-5-(2-chlorophenyl)-hexanoic acid;
3-Aminomethyl-5-(3-chlorophenyl)-hexanoic acid;
3-Aminomethyl-5-(4-chlorophenyl)-hexanoic acid;
3-Aminomethyl-5-(2-methoxyphenyl)-hexanoic acid;
3-Aminomethyl-5-(3-methoxyphenyl)-hexanoic acid;
3-Aminomethyl-5-(4-methoxyphenyl)-hexanoic acid; and
3-Aminomethyl-5-(phenylmethyl)-hexanoic acid.

Synthesis of Example 2
(3R,4S)3-Aminomethyl-4,5-dimethyl-hexanoic acid

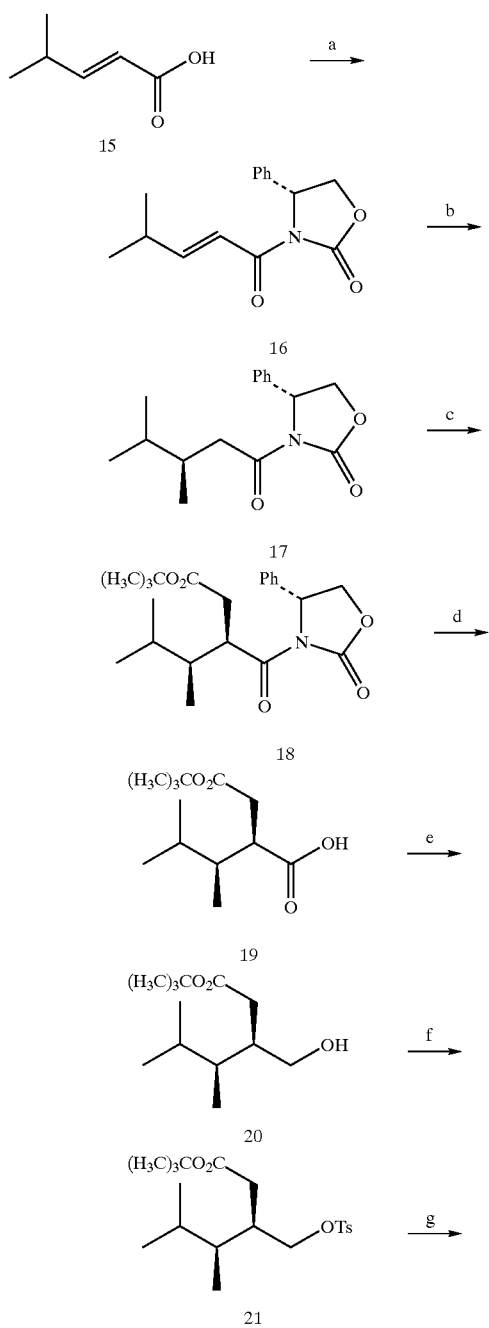

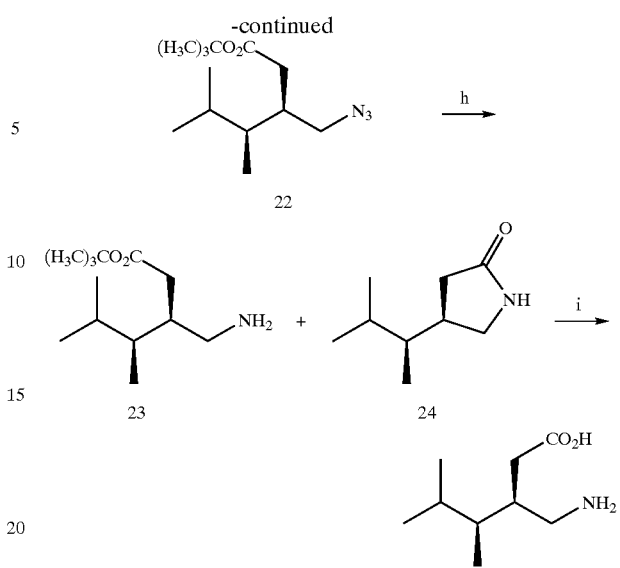

Example 2

Reagents and Conditions:
a) (R)-(−)-4-phenyl-2-oxazolidinone, $(CH_3)_3CCOCl$, $Et_3N$, LiCl, THF, −20 to 23° C.;
b) MeMgCl, $CuBrSMe_2$, THF, −35° C.;
c) NaHMDS, $BrCH_2CO_2tBu$, THF, −78° C. to −40° C.;
d) LiOH, $H_2O_2$, THF, $H_2O$, 25° C.;
e) $BH_3SMe_2$, THF, 0 to 25° C.;
f) pTsCl, pyridine, 25° C.;
g) $NaN_3$, DMSO, 60° C.;
h) Raney nickel, MeOH, $H_2$; i) 3M HCl, reflux, ion exchange resin (Dowex 50WX8, strongly acidic).

[R-(E)]3-(4-Methyl-pent-2-enoyl)-4-phenyl-oxazolidin-2-one 16

Trimethylacetyl chloride (7.8 g, 0.065 mol) was added to acid 14 (6.9 g, 0.06 mol) and triethylamine (18 g, 0.187 mol) in THF (200 mL) at −20° C. After 1 hour, lithium chloride (2.35 g, 0.55 mol) and (R)-(−)-4-phenyl-2-oxazolidinone (8.15 g, 0.05 mol) were added and the thick suspension warmed to room temperature. After 20 hours, the suspension was filtered and the filtrate concentrated. The resultant solid was recrystallized from hexane/ethyl acetate (5:1) to give the oxazolidinone 16 as a white solid (8.83 g, 68%). $^1H$ NMR ($CDCl_3$) δ7.35 (m, 5H), 7.18 (dd, 1H, J=15.4 and 1.2 Hz), 7.02 (dd, 1H, J=15.4 and 6.8 Hz), 5.45 (dd, 1H, J=8.8 and 3.9 Hz), 4.68 (t, 1H, J=8.8 Hz), 4.22 (dd, 1H, J=8.8 and 3.9 Hz), 2.50 (m, 1H), 1.04 (d, 1H, J=1.4 Hz), 1.02 (d, 1H, J=1.4 Hz). MS, m/z (relative intensity): 260 [M+H, 100%].

(3R,3R*)3-(3,4-Dimethyl-pentanoyl)-4-phenyl-oxazolidin-2-one 17

To copper(I) bromide-dimethyl sulphide complex in THF (45 mL) at −20° C. was added methylmagnesium chloride (as a 3 M solution in THF). After 20 minutes, the oxazolidinone 16 (3.69 g, 0.014 mol) in THF (20 mL) was added dropwise over 10 minutes. After 2.5 hours, the reaction was quenched through the addition of a saturated aqueous solution of ammonium chloride. The resultant two layers were separated and the aqueous phase extracted with ether. The combined organic phases were washed with 1 M hydrochloric acid, then with 5% aqueous ammonium hydroxide. The organic phases were dried ($MgSO_4$) and concentrated to give the oxazolidinone 17 as a white solid (3.39 g, 88%). $^1$H NMR (CDCl$_3$) δ7.30 (m, 1H), 5.40 (dd, 1H, J=8.8 and 3.7 Hz), 4.63 (t, 1H, J=8.8 Hz), 4.21 (dd, 1H, J=8.8 and 3.7 Hz), 2.85 (dd, 1H, J=16.1 and 5.6 Hz), 2.8 (dd, 1H, J=16.1 and 8.5 Hz), 1.90 (m, 1H), 1.56 (m, 2H), 0.83 (d, 3H, J=6.8 Hz), 0.78 (d, 3H, J=6.8 Hz), 0.75 (d, 3H, J=6.8 Hz). MS, m/z (relative intensity): 276 [M+H, 100%].

[3R-(3R*(R*),4S*)]-4,5-Dimethyl-3-(2-oxo-4-phenyl-oxazolidine-3-carbonyl)-hexanoic acid tert-butyl ester 18

Sodium bis(trimethylsilyl)amide (14.4 mL, 0.014 mol of a 1 M solution in THF) was added to a solution of the oxazolidinone 17 (3.37 g, 0.012 mol) in THF (35 mL) at −78° C. After 35 minutes, tert-butyl bromoacetate (3.5 g, 0.018 mol) was added and the solution immediately warmed to −40° C. After 3 hours, the reaction was quenched through the addition of a saturated aqueous solution of ammonium chloride. The resultant two layers were separated and the aqueous phase extracted with ether. The combined organic phases were dried (MgSO$_4$) and concentrated. Flash chromatography (9:1 to 5:1 hexane/ethyl acetate gradient) gave the ester 18 (3.81 g, 82%) as a white solid. $^1$H NMR (CDCl$_3$) δ7.35 (m, 5H), 5.37 (dd, 1H, J=8.4 and 3.1 Hz), 4.67 (t, 1H, J=8.7 Hz), 4.41 (dt, 1H, J=12.0 and 3.5 Hz), 4.25 (dd, 1H, J=8.68 and 3.1 Hz), 2.65 (dd, 1H, J=16.9 and 12.0 Hz), 2.25 (dd, 1H, J=16.9 and 3.5 Hz), 1.6 (m, 1H), 1.45 (m, 1H), 1.23 (s, 9H), 1.02 (d, 1H, J=6.5 Hz), 0.93 (d, 1H, J=6.7 Hz), 0.80 (d, 1H, J=7.0 Hz). MS, m/z (relative intensity): 429 [M−H+CH$_3$CN, 100%], 388 [M−H, 20%].

(3R,4S)-2-(1,2-Dimethyl-propyl)-succinic acid 4-tert-butyl ester 19

To the oxazolidinone 18 (3.62 g, 9.3 mmol) in THF (54 mL)/water (15 mL) was added a premixed solution of lithium hydroxide (20 mL of a 0.8 M aqueous solution, 0.016 mol)/H$_2$O$_2$ (5.76 mL of a 30% aqueous solution). After 7 hours, the solution was diluted with water and sodium bisulfite added (~10 g). After stirring for a further 0.5 hours, the two layers were separated and the aqueous phase extracted with ether. The aqueous phase was then rendered acidic (pH 2) with 1 M hydrochloric acid and extracted with ether. The combined organic phases were dried (MgSO$_4$) and concentrated. Flash chromatography (5:1 hexane/ethyl acetate) gave the acid 19 (2.1 g, 95%) as a colorless oil. $^1$H NMR (CDCl$_3$) δ3.0 (m, 1H), 2.55 (dd, 1H, J=16.6 and 11.2 Hz), 2.27 (dd, 1H, J=16.6 and 3.4 Hz), 1.70 (m, 1H), 1.53 (m, 1H), 1.45 (m, 1H), 1.43 (s, 9H), 0.95 (d, 1H, J=6.8 Hz), 0.90 (d, 1H, J=6.6 Hz), 0.83 (d, 1H, J=6.8 Hz). MS, m/z (relative intensity): 243 [M−H, 100%].

(3R,4S)-3-Hydroxymethyl-4,5-dimethyl-hexanoic acid tert-butyl ester 20

Borane-methyl sulfide complex (16 mL, 0.032 mol of a 2 M solution in THF) was added to a stirred solution of the acid 19 (1.96 g, 8 mmol) in THF (20 mL) at 0° C. After 20 hours, methanol was added until effervescence ceased and the solution concentrated. Flash chromatography (5:1 hexane/ethyl acetate gradient) gave the alcohol 20 (1.29 g, 70%) as a colorless oil. $^1$H NMR (CDCl$_3$) δ3.62 (m, 1H), 2.32 (m, 1H), 2.14 (m, 1H), 1.6 (m, 1H), 1.45 (s, 9H), 1.35 (m, 1H), 0.93 (d, 1H, J=6.8 Hz), 0.86 (d, 1H, J=6.8 Hz), 0.77 (d, 1H, J=6.9 Hz). MS, m/z (relative intensity): 175 [M−tBu, 100%].

(3R,4S)-4,5-Dimethyl-3-(toluene-4-sulfonyloxymethyl)-hexanoic acid tert-butyl ester 21 p-Toluenesulfonyl chloride (847 mg, 4.4 mmol) was added to a stirred solution of the alcohol 6 (850 mg, 3.7 mmol), DMAP (10 mg, 0.08 mmol) and triethylamine (1.23 mL, 8.88 mmol) in CH$_2$Cl$_2$ (20 mL) at 0° C. and the solution warmed to room temperature. After 15 hours, the solution was washed with 1N hydrochloric acid then with brine. The combined organic phases were dried (MgSO$_4$) and concentrated. Flash chromatography (100 to 92% hexane/ethyl acetate gradient) gave the tosylate 7 (1.22 g, 86%) as a thick gum. $^1$H NMR (CDCl$_3$) δ7.80 (d, 2H, J=8.2 Hz), 7.25 (d, 2H, J=8.2 Hz), 3.92 (m, 1H), 2.38 (s, 3H), 2.20 (m, 2H), 1.95 (m, 1H), 1.40 (m, 1H), 1.32 (s, 9H), 1.27 (m, 1H), 0.78 (d, 1H, J=6.6 Hz), 0.73 (d, 1H, J=6.6 Hz), 0.63 (d, 1H, J=7.1 Hz). MS, m/z (relative intensity): 311 [85%], 198 [100%], 157 [95%].

(3R,4S)-3-Azidomethyl-4,5-dimethyl-hexanoic acid tert-butyl ester 22

A solution of the tosylate 21 (1.19 g, 3.1 mmol) and sodium azide (402 mg, 6.2 mmol) in DMSO (15 mL) was warmed to 60° C. for 2.5 hours. Water (100 mL) was added and the solution extracted with ether. The combined organic phases were dried (MgSO$_4$) and concentrated. Flash chromatography (9:1 hexane/ethyl acetate) gave the azide 22 (628 mg, 80%) as a colorless oil. $^1$H NMR (CDCl$_3$) δ3.4 (dd, 1H, J=12.21 and 6.11 Hz), 3.3 (dd, 1H, J=21.11 and 6.59 Hz), 2.30 (dd, 1H, J=15.14 and 3.66 Hz), 2.25 (m, 1H), 2.05 (dd, 1H, J=15.14 and 9.04 Hz), 1.55 (m, 1H), 1.45 (s, 9H), 1.35 (m, 1H), 0.95 (d, 1H, J=6.59 Hz), 0.90 (d, 1H, J=6.83 Hz), 0.80 (d, 1H, J=7.08 Hz). MS (m/z): (relative intensity): 228 [M−N$_2$, 35%], 172 [M−N$_2$−tBu, 100%].

(3R,4S)-3-Aminomethyl-4,5-dimethyl-hexanoic acid tert-butyl ester 23 and [4R-[4R*(S*)]]-4-(1,2-Dimethyl-propyl)-pyrrolidin-2-one 24

The azide 8 (640 mg, 2.5 mmol) and Raney nickel (1 g) in methanol (50 mL) were shaken under an atmosphere of hydrogen for 4 hours. The solution was filtered and the filtrate concentrated to give a mixture of the amine 23 and lactam 24 which was used without further purification in the next step.

(3R,4S)-3-Aminomethyl-4,5-dimethyl-hexanoic acid (Example 2)

A solution of the amine 23 and lactam 24 (500 mg) in 3 M hydrochloric acid were heated to reflux for 9 hours, then stirred at room temperature for 15 hours. The solution was concentrated and the resultant solid subjected to a sequential purification which involved ion exchange chromatography (Dowex 50WX8, strongly acidic), oxalate salt formation then further purification by ion exchange chromatography (Dowex 50WX8, strongly acidic) to give the Example 2 (343 mg) as a white solid. $^1$H NMR (D$_2$O) δ2.87 (m, 2H), 2.22 (dd, 1H, J=15.4 and 3.4 Hz), 2.12 (m, 1H), 1.93 (dd, 1H, J=15.4 and 9.5 Hz), 1.38 (m, 1H), 1.12 (m, 1H), 0.77 (d, 1H, J=6.6 Hz), 0.74 (d, 1H, J=6.6 Hz), 0.70 (d, 1H, J=6.8 Hz). MS, m/z (relative intensity): 174 [M+H, 100%].

In a similar way, the following examples can be prepared:

3-Aminomethyl-4,5-dimethyl-hexanoic acid;
(3R,4S)-3-Aminomethyl-4,5-dimethyl-hexanoic acid MP;
(3S,4S)-3-Aminomethyl-4,5-dimethyl-hexanoic acid;
(3R,4R)-3-Aminomethyl-4,5-dimethyl-hexanoic acid MP;
3-Aminomethyl-4-isopropyl-hexanoic acid;
3-Aminomethyl-4-isopropyl-heptanoic acid;
3-Aminomethyl-4-isopropyl-octanoic acid;
3-Aminomethyl-4-isopropyl-nonanoic acid;
3-Aminomethyl-4-isopropyl-decanoic acid; and
3-Aminomethyl-4-phenyl-5-methyl-hexanoic acid.

Method 3

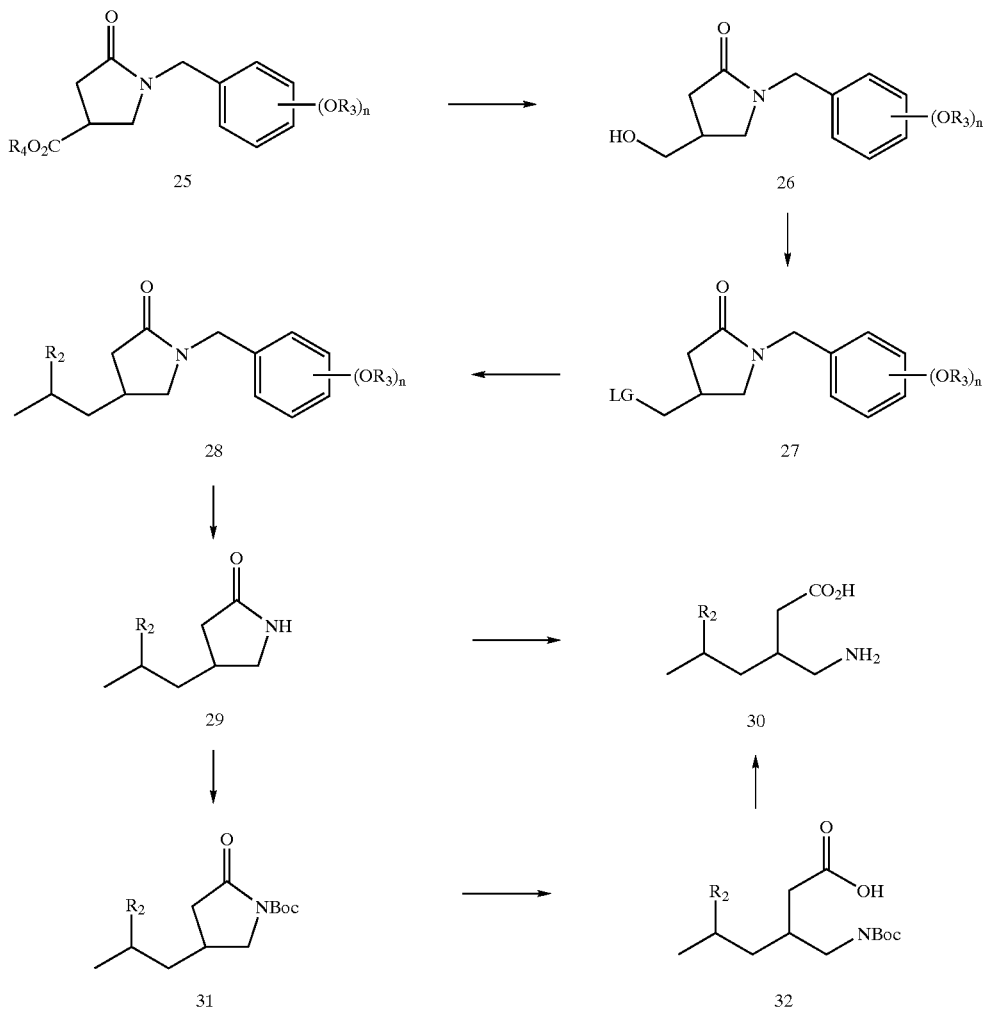

where
$R_3$ = OMe or H
$R_4$ = Me, Et
n = 0 to 2 benzyl groups from nitrogen are described in Green, *Protective Groups in Organic Synthesis,* Wiley, 2 ed, 1991 and could be utilized.

A compound of structure 28 could be prepared from a compound of structure 27 (where LG is a suitable leaving group such as a halide or an alkyl sulphonate, preferably an iodide would be used) by carbon-carbon bond forming reactions known in the art. Several methods exist in the literature for the coupling of organohalides or organoalkyl sulphonates with organometallic reagents in the presence of various metal salts as summarized in *Comprehensive Organic Synthesis,* volume 3:413 which could be utilized. For example, a compound of structure 28 could be prepared from a compound of structure 27 (where LG is iodide) by treatment with a suitable secondary halide (chloride or iodide) in the presence of magnesium metal, iodine and copper bromide dimethylsulphide in a solvent such as tetrahydrofuran and alike. Alternatively the method according to El Marini, *Synthesis,* 1992:1104 could be used. Hence, a compound of structure 28 could be prepared from a compound of structure 27 (where LG is iodide) by treatment with suitable methyl-substituted secondary halide such as an A compound of structure 30 could be prepared from a compound of structure 29 treatment with an aqueous acid such as hydrochloric acid and alike at a temperature between room temperature and reflux. As an alternative, a compound of structure 30 can be prepared from a compound of structure 32 by treatment with trifluoroacetic acid in a solvent such as $CH_2Cl_2$ or EtOAc and alike. Compound 32 could be prepared by base mediate hydrolysis of a Boc protected lactam such as compound 31 which itself could be prepared from a compound of structure 29 by treatment with di-tert-butyl dicarbonate in a solvent such as THF and alike. The treatment of the Boc-lactam 31 with aqueous sodium hydroxide for example would give rise to the acid 32.

A compound of structure 29 could be prepared from compound of structure 28 (n=0) by treatment with sodium or lithium metal in ammonia. Preferably, the reaction is carried out with sodium metal in ammonia. Alternatively, a compound of structure 29 could be prepared from compound of structure 28 (n=1 or 2) by treatment with ceric ammonium nitrate in a mixture of acetonitrile and water. Other methods known in the literature for the removal of substituted alkoxy iodide in the presence of magnesium, iodine and lithium tetrachlorocuprate in a solvent such as tetrahydrofuran and alike.

A compound of structure 27 incorporates a suitable leaving group, which would undergo nucleophilic substitution with suitable nucleophile. Examples of such leaving groups include halides such as chloride, bromide, or iodide, and sulphonic esters such as mesylate, tosylate, triflate, nosylate, and alike. A compound of structure 27 (where LG=iodide) could be prepared from a compound of structure 26 through treatment with iodine, triphenylphosphine, and imidazole in a solvent such as toluene and alike.

A compound of structure 26 could be prepared from compound of structure 25 by treatment with a metal borohydride, such as sodium borohydride in a solvent such as tetrahydrofuran or DME and alike.

Compound 25 could be prepared in a similar fashion to the procedures of Zoretic et al, *J. Org. Chem.*, 1980;45:810–814 or Nielsen et al *J. Med. Chem.*, 1990;33:71–77 using an appropriate benzylamine, such as but not limited to benzylamine, 4-methoxybenzylamine or 2,4-dimethoxybenzylamine.

As an alternative approach, a compound of structure 26 could be treated with sodium metal and ammonia to give 4-hydroxymethyl-pyrrolidinone which could be iodinated affording 4-iodomethyl-pyrrolidinone. 4-iodomethyl-pyrrolidinone could then be coupled with organometallic reagents according to the above procedures avoiding protection of the lactam nitrogen as below.

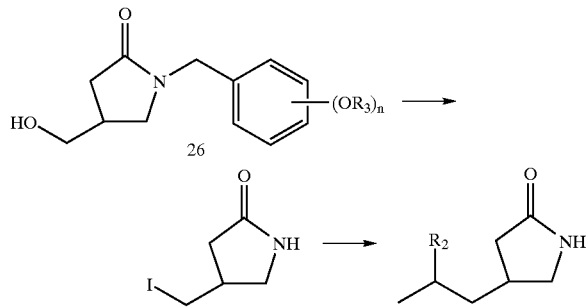

Analogous to the above methods a lactam of structure 33 (see Nielsen et. al., *J. Med. Chem.*, 1990;33:71–77 for general method of preparation) could be employed thus establishing fixed stereochemistry at C3 of the final amino acids.

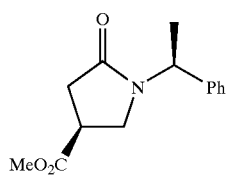

Compounds which could be prepared in this manner include:

3-Aminomethyl-5-methyl-6-phenyl-hexanoic acid;
3-Aminomethyl-6-(4-chloro-phenyl)-5-methyl-hexanoic acid;
3-Aminomethyl-6-(3-chloro-phenyl)-5-methyl-hexanoic acid;
3-Aminomethyl-6-(2-chloro-phenyl)-5-methyl-hexanoic acid;
3-Aminomethyl-6-(4-fluoro-phenyl)-5-methyl-hexanoic acid;
3-Aminomethyl-6-(3-fluoro-phenyl)-5-methyl-hexanoic acid;
3-Aminomethyl-6-(2-fluoro-phenyl)-5-methyl-hexanoic acid;
3-Aminomethyl-5-methyl-7-phenyl-heptanoic acid;
3-Aminomethyl-7-(4-chloro-phenyl)-5-methyl-heptanoic acid;
3-Aminomethyl-7-(3-chloro-phenyl)-5-methyl-heptanoic acid;
3-Aminomethyl-7-(2-chloro-phenyl)-5-methyl-heptanoic acid;
3-Aminomethyl-7-(4-fluoro-phenyl)-5-methyl-heptanoic acid;
3-Aminomethyl-7-(3-fluoro-phenyl)-5-methyl-heptanoic acid;
3-Aminomethyl-7-(2-fluoro-phenyl)-5-methyl-heptanoic acid;
(3S)-3-Aminomethyl-6-cyclopropyl-5-methyl-hexanoic acid;
(3S)-3-Aminomethyl-6-cyclobutyl-5-methyl-hexanoic acid;
(3S)-3-Aminomethyl-6-cyclopentyl-5-methyl-hexanoic acid;
(3S)-3-Aminomethyl-6-cyclohexyl-5-methyl-hexanoic acid;
(3S)-3-Aminomethyl-7-cyclopropyl-5-methyl-heptanoic acid;
(3S)-3-Aminomethyl-7-cyclobutyl-5-methyl-heptanoic acid;
(3S)-3-Aminomethyl-7-cyclopentyl-5-methyl-heptanoic acid;
(3S)-3-Aminomethyl-7-cyclohexyl-5-methyl-heptanoic acid;
(3S)-3-Aminomethyl-8-cyclopropyl-5-methyl-octanoic acid;
(3S)-3-Aminomethyl-8-cyclobutyl-5-methyl-octanoic acid;
(3S)-3-Aminomethyl-8-cyclopentyl-5-methyl-octanoic acid;
(3S)-3-Aminomethyl-8-cyclohexyl-5-methyl-octanoic acid;
(3S)-3-Aminomethyl-5-methyl-heptanoic acid;
(3S)-3-Aminomethyl-5-methyl-octanoic acid;
(3S)-3-Aminomethyl-5-methyl-nonanoic acid;
(3S)-3-Aminomethyl-5-methyl-decanoic acid;
(3S)-3-Aminomethyl-5-methyl-undecanoic acid;
(3S)-3-Aminomethyl-5,7-dimethyl-octanoic acid;
(3S)-3-Aminomethyl-5,8-dimethyl-nonanoic acid;
(3S)-3-Aminomethyl-5,9-dimethyl-decanoic acid;
(3S)-3-Aminomethyl-5,6-dimethyl-heptanoic acid;
(3S)-3-Aminomethyl-5,6,6-trimethyl-heptanoic acid;
(3S)-3-Aminomethyl-5-cyclopropyl-hexanoic acid;
(3S)-3-Aminomethyl-6-fluoro-5-methyl-hexanoic acid;
(3S)-3-Aminomethyl-7-fluoro-5-methyl-heptanoic acid;
(3S)-3-Aminomethyl-8-fluoro-5-methyl-octanoic acid;
(3S)-3-Aminomethyl-7,7,7-trifluoro-5-methyl-heptanoic acid;
(3S)-3-Aminomethyl-8,8,8-trifluoro-5-methyl-octanoic acid;
(3S)-3-Aminomethyl-5-methyl-hept-6-enoic acid;
(3S)-3-Aminomethyl-5-methyl-oct-7-enoic acid;
(3S)-3-Aminomethyl-5-methyl-non-8-enoic acid;
(E)-(3S)-3-Aminomethyl-5-methyl-oct-6-enoic acid;
(Z)-(3S)-3-Aminomethyl-5-methyl-oct-6-enoic acid;
(E)-(3S)-3-Aminomethyl-5-methyl-non-6-enoic acid;
(Z)-(3S)-3-Aminomethyl-5-methyl-non-6-enoic acid;
(E)-(3S)-3-Aminomethyl-5-methyl-non-7-enoic acid;
(Z)-(3S)-3-Aminomethyl-5-methyl-non-7-enoic acid;

(E)-(3S)-3-Aminomethyl-5-methyl-dec-7-enoic acid;
(Z)-(3S)-3-Aminomethyl-5-methyl-dec-7-enoic acid;
3-Aminomethyl-6-cyclopropyl-5-methyl-hexanoic acid;
3-Aminomethyl-6-cyclobutyl-5-methyl-hexanoic acid;
3-Aminomethyl-6-cyclopentyl-5-methyl-hexanoic acid;
3-Aminomethyl-6-cyclohexyl-5-methyl-hexanoic acid;
3-Aminomethyl-7-cyclopropyl-5-methyl-heptanoic acid;
3-Aminomethyl-7-cyclobutyl-5-methyl-heptanoic acid;
3-Aminomethyl-7-cyclopentyl-5-methyl-heptanoic acid;
3-Aminomethyl-7-cyclohexyl-5-methyl-heptanoic acid;
3-Aminomethyl-8-cyclopropyl-5-methyl-octanoic acid;
3-Aminomethyl-8-cyclobutyl-5-methyl-octanoic acid;
3-Aminomethyl-8-cyclopentyl-5-methyl-octanoic acid;
3-Aminomethyl-8-cyclohexyl-5-methyl-octanoic acid;
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5,7-dimethyl-octanoic acid;
3-Aminomethyl-5,8-dimethyl-nonanoic acid;
3-Aminomethyl-5,9-dimethyl-decanoic acid;
3-Aminomethyl-5,6-dimethyl-heptanoic acid;
3-Aminomethyl-5,6,6-trimethyl-heptanoic acid;
3-Aminomethyl-5-cyclopropyl-hexanoic acid;
3-Aminomethyl-6-fluoro-5-methyl-hexanoic acid;
3-Aminomethyl-7-fluoro-5-methyl-heptanoic acid;
3-Aminomethyl-8-fluoro-5-methyl-octanoic acid;
3-Aminomethyl-7,7,7-trifluoro-5-methyl-heptanoic acid;
3-Aminomethyl-8,8,8-trifluoro-5-methyl-octanoic acid;
3-Aminomethyl-5-methyl-hept-6-enoic acid;
3-Aminomethyl-5-methyl-oct-7-enoic acid;
3-Aminomethyl-5-methyl-non-8-enoic acid;
(E)-3-Aminomethyl-5-methyl-oct-6-enoic acid;
(Z)-3-Aminomethyl-5-methyl-oct-6-enoic acid;
(E)-3-Aminomethyl-5-methyl-non-6-enoic acid;
(Z)-3-Aminomethyl-5-methyl-non-6-enoic acid;
(E)-3-Aminomethyl-5-methyl-non-7-enoic acid;
(Z)-3-Aminomethyl-5-methyl-non-7-enoic acid;
(E)-3-Aminomethyl-5-methyl-dec-7-enoic acid; and
(Z)-3-Aminomethyl-5-methyl-dec-7-enoic acid.

Method 4

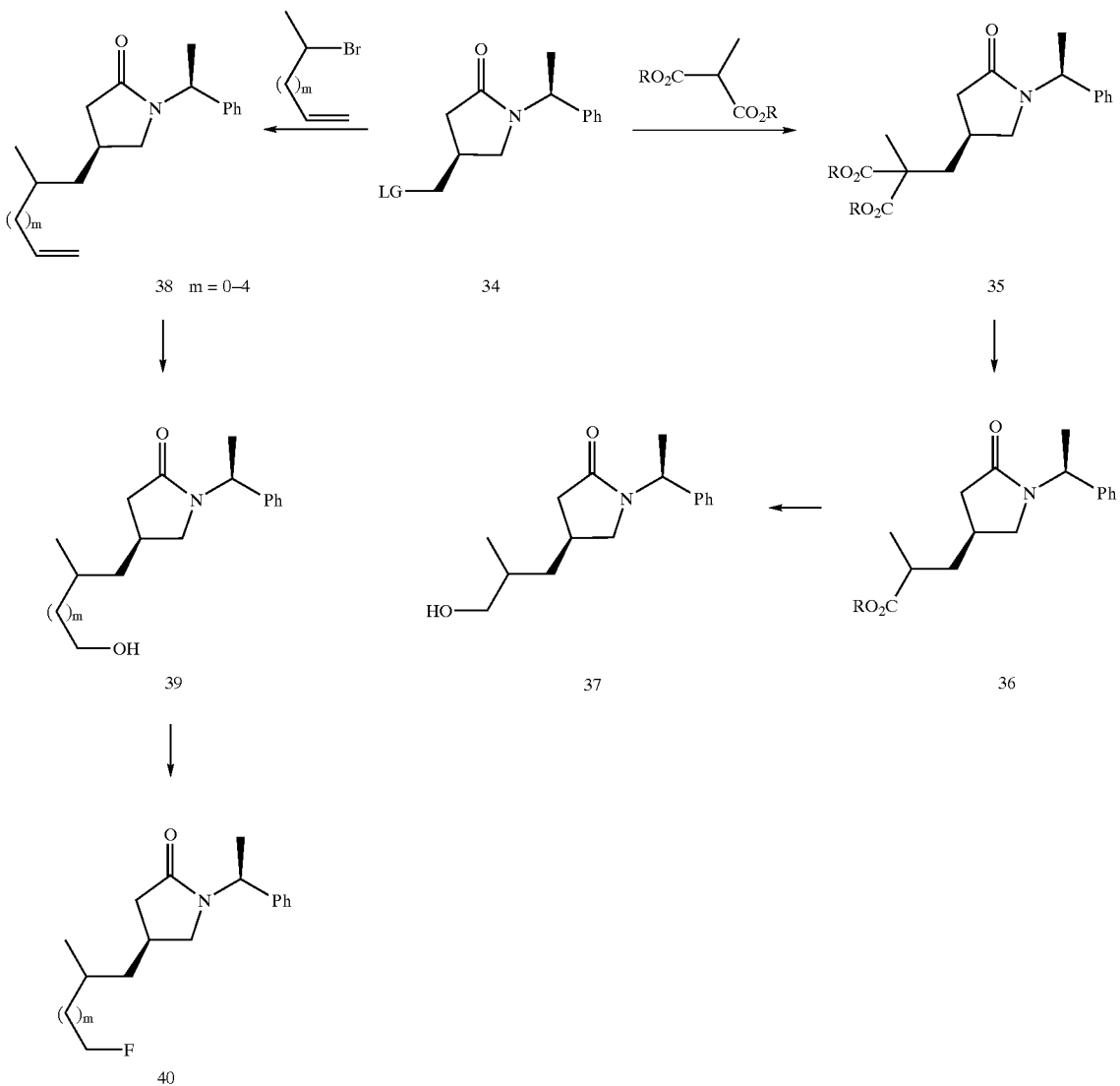

A compound of structure 40 could be prepared from compound of structure 39 through treatment with diethylaminosulphur trifluoride in a solvent such as methylene chloride at a temperature between −78° C. and room temperature. Other methods for the fluorination of alcohols are known and could be utilized as exemplified in Wilkinson, *Chem. Rev.* 1992;92:505–519. Compounds of structure 40 can be converted to the requisite γ-amino acid as described in method 3 above.

A compound of structure 39 could be prepared from compound of structure 38 through treatment with osmium tetroxide and sodium periodate in a solvent such as THF and water and reduction of the resultant intermediate with sodium borohydride in a solvent such as ethanol.

Compounds of structures 38 and 34 could be prepared from compound of structure 33 according to the principles described in method 3.

An alternative procedure for the synthesis of alcohol 39 (n=0) involves the treatment of a compound of structure 36 with a metal borohydride, such as sodium borohydride in a solvent such as tetrahydrofuran or DME and alike to give a compound of structure 37, the fluorination of which could be achived in a similar manner to the preparation of a compound of strucutre 40. A compound of structure 36 could be prepared from compound of structure 35 through treatment with sodium or lithium chloride in aqueous DMSO at a temperature between room temperature and reflux. Preferably the reaction is carried out using sodium chloride in aqueous DMSO at reflux. A compound of structure 35 could be prepared from compound of structure 34 through treatment with a suitable methyl malonic acid diester, such as dimethyl methylmalonate and alike with sodium hydride in a solvent such as DMSO or THF and alike. Preferably the reaction is carried out by adding NaH to a solution of dimethyl methylmalonate in DMSO followed by the addition of the lactam 34 (where LG is preferably iodide or as defined in method 3) pre-dissolved in DMSO.

Compounds 39 and 37 can be converted to the free amino acids bearing a hydroxyl group by the methods described above.

The following compounds could be prepared in this manner:

(3S)-3-Aminomethyl-6-fluoro-5-methyl-hexanoic acid;
(3S)-3-Aminomethyl-6-fluoro-5-methyl-hexanoic acid;
(3S)-3-Aminomethyl-7-fluoro-5-methyl-heptanoic acid;
(3S)-3-Aminomethyl-8-fluoro-5-methyl-octanoic acid;
(3S)-3-Aminomethyl-9-fluoro-5-methyl-nonanoic acid;
(3S)-3-Aminomethyl-7-hydroxy-5-methyl-heptanoic acid; and
(3S)-3-Aminomethyl-6-hydroxy-5-methyl-hexanoic acid.

Method 5

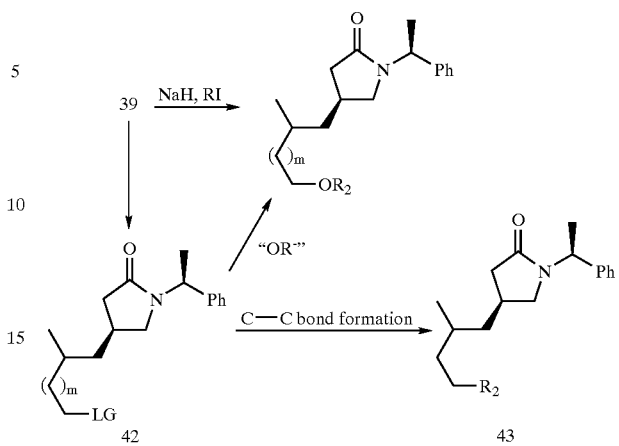

A compound of structure 41 could be prepared from compound of structure 39 through treatment with a suitable alkyl iodide (or alkyl sulphonate), such as methyl iodide and alike, and a base such as n-butyl lithium or sodium hydride and alike, in a solvent such as DMSO or THF and alike. Preferably the reaction is carried out by adding NaH to a solution of the alcohol in DMSO followed by the addition of the alkyl iodide and heating of the reaction mixture at a temperature between room temperature and reflux. The conversion of compounds of structure 41 to the γ-amino acids has been described above.

Alternatively, compounds of structure 41 could be derived from compounds of structure 42 (where LG=iodide, bromide or an sulphonic acid ester, as exampled in method 3) by treatment of an appropriate alkoxy anion in a solvent such as DMSO or THF and alike. A compound of structure 42 would also serve as a substrate for carbon-carbon bond forming procedures as outlined in method 3.

Compounds which could be prepared in this manner include:

(3S)-3-Aminomethyl-7-hydroxy-5-methyl-heptanoic acid;
(3S)-3-Aminomethyl-7-methoxy-5-methyl-heptanoic acid;
(3S)-3-Aminomethyl-7-ethoxy-5-methyl-heptanoic acid;
(3S)-3-Aminomethyl-5-methyl-7-propoxy-heptanoic acid;
(3S)-3-Aminomethyl-7-fluoromethoxy-5-methyl-heptanoic acid;
(3S)-3-Aminomethyl-7-(2-fluoro-ethoxy)-5-methyl-heptanoic acid;
(3S)-3-Aminomethyl-5-methyl-7-(3,3,3-trifluoro-propoxy)-heptanoic acid;
(3S)-3-Aminomethyl-6-hydroxy-5-methyl-hexanoic acid;
(3S)-3-Aminomethyl-6-methoxy-5-methyl-hexanoic acid;
(3S)-3-Aminomethyl-6-ethoxy-5-methyl-hexanoic acid;
(3S)-3-Aminomethyl-5-methyl-6-propoxy-hexanoic acid;
(3S)-3-Aminomethyl-6-fluoromethoxy-5-methyl-hexanoic acid;
(3S)-3-Aminomethyl-6-(2-fluoro-ethoxy)-5-methyl-hexanoic acid; and
(3S)-3-Aminomethyl-5-methyl-6-(3,3,3-trifluoro-propoxy)-hexanoic acid.

Method 6

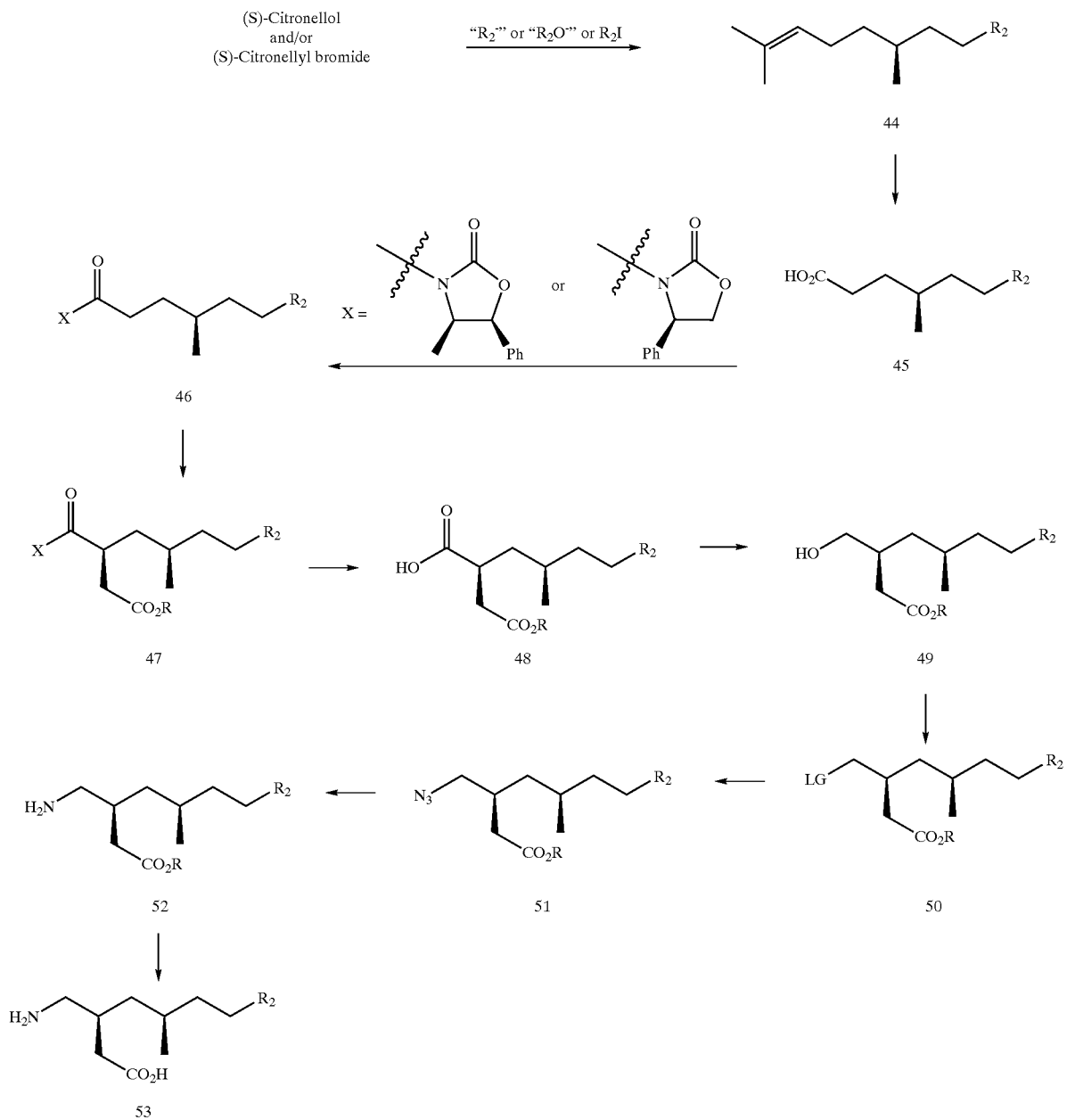

Compounds of structure 53 could be prepared from a compound of structure 45 as shown above and by the general procedures described in Hoekstra et. al., *Organic Process Research and Development*, 1997;1:26–38.

Compounds of structure 45 can be prepared from compounds of structure 44 by treatment with a solution of chromium trioxide in water/sulfuric acid. Alternative methods of cleaving the olefin in 44 could be utilized as detailed in Hudlicky, *Oxidations in Organic Chemistry*, ACS Monograph 186, ACS 1990:77.

Compounds of structure 44 (where $R_2$=alkyl, branched alkyl, cycloalkyl, alkyl-cycloalkyl) could be prepared from (S)-citronellyl bromide by carbon-carbon bond forming reactions known in the art and as described in method 3. The substitution of the halide in (S)-citronellyl bromide with alkoxy anions could also be used to provide compounds of structure 44 where R=alkoxy or phenoxy ethers (and appropriate substitutions thereof as according to Formula 1). Alternatively (S)-citronellol could be utilized to afford compounds of structure 44 by treatment of (S)-citronellol with a base such as sodium hydride, and treatment of the resultant alkoxide with an appropriate alkyl halide to afford ethers. In another method (S)-citronellyl bromide (or an appropriate sulphonic ester such as, but not limited to, methanesulfonic acid (S)-3,7-dimethyl-oct-6-enyl ester) could be reduced with an appropriate metal borohydride or with an aluminum hydride species, such as LAH, to provide (R)-2,6-dimethyl-oct-2-ene.

To one skilled in the art it will be appreciated that rational choice of either R- or S-citronellol or R- or S-citronellyl bromide would give rise to the requisite isomer at C5 of the final amino acid.

Compounds which could be prepared in this manner include:
(3S,5S)-3-Aminomethyl-7-methoxy-5-methyl-heptanoic acid;
(3S,5S)-3-Aminomethyl-7-ethoxy-5-methyl-heptanoic acid;
(3S,5S)-3-Aminomethyl-5-methyl-7-propoxy-heptanoic acid;
(3S,5S)-3-Aminomethyl-7-isopropoxy-5-methyl-heptanoic acid;
(3S,5S)-3-Aminomethyl-7-tert-butoxy-5-methyl-heptanoic acid;
(3S,5S)-3-Aminomethyl-7-fluoromethoxy-5-methyl-heptanoic acid;
(3S,5S)-3-Aminomethyl-7-(2-fluoro-ethoxy)-5-methyl-heptanoic acid;
(3S,5S)-3-Aminomethyl-5-methyl-7-(3,3,3-trifluoro-propoxy)-heptanoic acid;
(3S,5S)-3-Aminomethyl-7-benzyloxy-5-methyl-heptanoic acid;
(3S,5S)-3-Aminomethyl-5-methyl-7-phenoxy-heptanoic acid;
(3S,5S)-3-Aminomethyl-7-(4-chloro-phenoxy)-5-methyl-heptanoic acid;
(3S,5S)-3-Aminomethyl-7-(3-chloro-phenoxy)-5-methyl-heptanoic acid;
(3S,5S)-3-Aminomethyl-7-(2-chloro-phenoxy)-5-methyl-heptanoic acid;
(3S,5S)-3-Aminomethyl-7-(4-fluoro-phenoxy)-5-methyl-heptanoic acid;
(3S,5S)-3-Aminomethyl-7-(3-fluoro-phenoxy)-5-methyl-heptanoic acid;
(3S,5S)-3-Aminomethyl-7-(2-fluoro-phenoxy)-5-methyl-heptanoic acid;
(3S,5S)-3-Aminomethyl-7-(4-methoxy-phenoxy)-5-methyl-heptanoic acid;
(3S,5S)-3-Aminomethyl-7-(3-methoxy-phenoxy)-5-methyl-heptanoic acid;
(3S,5S)-3-Aminomethyl-7-(2-methoxy-phenoxy)-5-methyl-heptanoic acid;
(3S,5S)-3-Aminomethyl-5-methyl-7-(4-trifluoromethyl-phenoxy)-heptanoic acid;
(3S,5S)-3-Aminomethyl-5-methyl-7-(3-trifluoromethyl-phenoxy)-heptanoic acid;
(3S,5S)-3-Aminomethyl-5-methyl-7-(2-trifluoromethyl-phenoxy)-heptanoic acid;
(3S,5S)-3-Aminomethyl-5-methyl-7-(4-nitro-phenoxy)-heptanoic acid;
(3S,5S)-3-Aminomethyl-5-methyl-7-(3-nitro-phenoxy)-heptanoic acid;
(3S,5S)-3-Aminomethyl-5-methyl-7-(2-nitro-phenoxy)-heptanoic acid;
(3S,5R)-3-Aminomethyl-7-cyclopropyl-5-methyl-heptanoic acid;
(3S,5R)-3-Aminomethyl-7-cyclobutyl-5-methyl-heptanoic acid;
(3S,5R)-3-Aminomethyl-7-cyclopentyl-5-methyl-heptanoic acid;
(3S,5R)-3-Aminomethyl-7-cyclohexyl-5-methyl-heptanoic acid;
(3S,5R)-3-Aminomethyl-8-cyclopropyl-5-methyl-octanoic acid;
(3S,5R)-3-Aminomethyl-8-cyclobutyl-5-methyl-octanoic acid;
(3S,5R)-3-Aminomethyl-8-cyclopentyl-5-methyl-octanoic acid;
(3S,5R)-3-Aminomethyl-8-cyclohexyl-5-methyl-octanoic acid;
(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5,9-dimethyl-decanoic acid;
(3S,5R)-3-Aminomethyl-5,8-dimethyl-nonanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5R)-3-Aminomethyl-8,8,8-trifluoro-5-methyl-octanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid; and
(3S,5R)-3-Aminomethyl-5,10-dimethyl-undecanoic acid.

Method 7

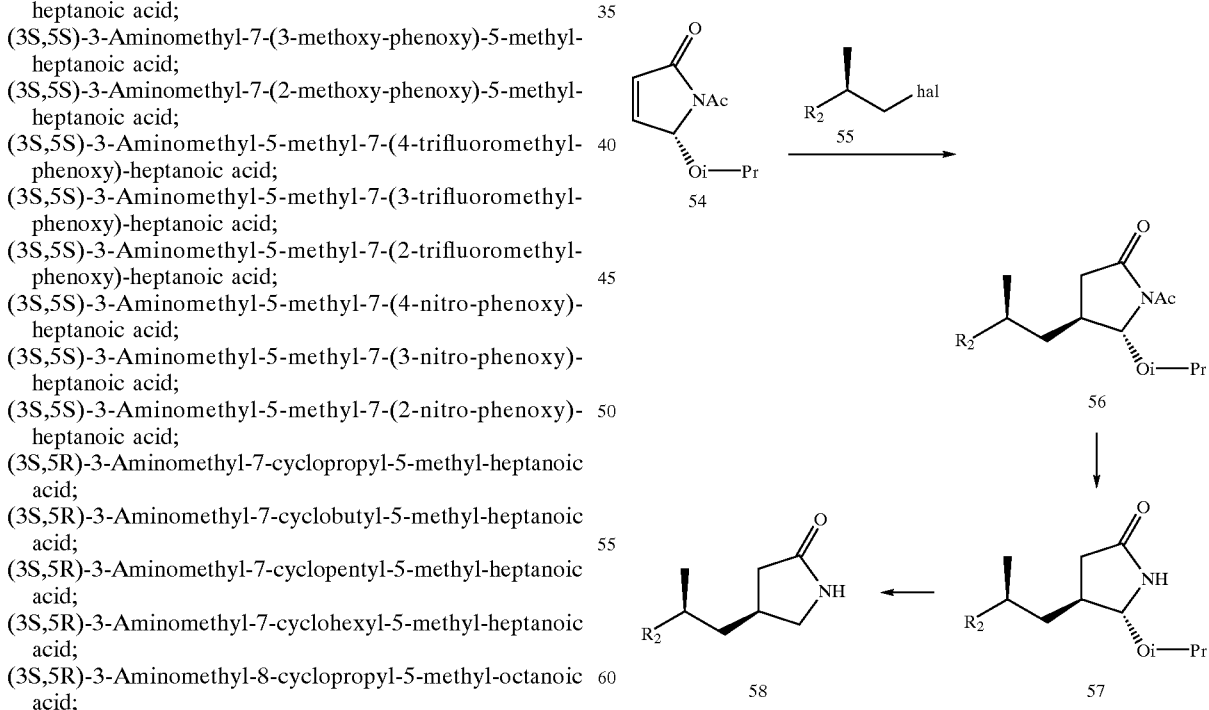

A compound of structure 58 can be prepared from a compound of structure 57 by treatment with borontrifluoride diethyletherate and triethylsilane in a solvent such as $CH_2Cl_2$. Alternatively the method described in Meyers, *J. Org. Chem.*, 1993;58:36–42, could be utilized thus treating a compound of structure 57 with sodium cyanoborohydride in a solvent such as THF/methanol with 3% HCl in methanol.

A compound of structure 57 can be prepared from a compound of structure 56 by treatment with dimethylamine in a solvent such as DMF and alike according to the procedure of Koot, *Tetrahedron Lett.*, 1992;33:7969–7972.

A compound of structure 56 can be prepared from a compound of structure 54 by treatment of a suitable primary halide 55 (iodide, bromide, or chloride) under standard transmetallation conditions with tBuLi and treatment of the resultant organometallic reagent with suitable copper salt, such as but not limited to, copper bromide or copper iodide. The resultant organo-cuprate is added to lactam (see Koot et al, *J. Org. Chem.*, 1992;57:1059–1061 for the preparation of the chiral lactam 54) in a solvent such as THF and alike. The procedure of Koot, *Tetrahedron Lett.*, 1992;33:7969–7972 exemplifies this method.

To one skilled in the art it will be appreciated that rational choice of either R- or S-primary halides 55 would give rise to the requisite isomer at C5 of the final amino acid.

Compounds which could be prepared in this manner include:

(3S,5S)-3-Aminomethyl-5-methoxy-hexanoic acid;
(3S,5S)-3-Aminomethyl-5-ethoxy-hexanoic acid;
(3S,5S)-3-Aminomethyl-5-propoxy-hexanoic acid;
(3S,5S)-3-Aminomethyl-5-isopropoxy-hexanoic acid;
(3S,5S)-3-Aminomethyl-5-tert-butoxy-hexanoic acid;
(3S,5S)-3-Aminomethyl-5-fluoromethoxy-hexanoic acid;
(3S,5S)-3-Aminomethyl-5-(2-fluoro-ethoxy)-hexanoic acid;
(3S,5S)-3-Aminomethyl-5-(3,3,3-trifluoro-propoxy)-hexanoic acid;
(3S,5S)-3-Aminomethyl-5-phenoxy-hexanoic acid;
(3S,5S)-3-Aminomethyl-5-(4-chloro-phenoxy)-hexanoic acid;
(3S,5S)-3-Aminomethyl-5-(3-chloro-phenoxy)-hexanoic acid;
(3S,5S)-3-Aminomethyl-5-(2-chloro-phenoxy)-hexanoic acid;
(3S,5S)-3-Aminomethyl-5-(4-fluoro-phenoxy)-hexanoic acid;
(3S,5S)-3-Aminomethyl-5-(3-fluoro-phenoxy)-hexanoic acid;
(3S,5S)-3-Aminomethyl-5-(2-fluoro-phenoxy)-hexanoic acid;
(3S,5S)-3-Aminomethyl-5-(4-methoxy-phenoxy)-hexanoic acid;
(3S,5S)-3-Aminomethyl-5-(3-methoxy-phenoxy)-hexanoic acid;
(3S,5S)-3-Aminomethyl-5-(2-methoxy-phenoxy)-hexanoic acid;
(3S,5S)-3-Aminomethyl-5-(4-nitro-phenoxy)-hexanoic acid;
(3S,5S)-3-Aminomethyl-5-(3-nitro-phenoxy)-hexanoic acid;
(3S,5S)-3-Aminomethyl-5-(2-nitro-phenoxy)-hexanoic acid;
(3S,5S)-3-Aminomethyl-6-methoxy-5-methyl-hexanoic acid;
(3S,5S)-3-Aminomethyl-6-ethoxy-5-methyl-hexanoic acid;
(3S,5S)-3-Aminomethyl-5-methyl-6-propoxy-hexanoic acid;
(3S,5S)-3-Aminomethyl-6-isopropoxy-5-methyl-hexanoic acid;
(3S,5S)-3-Aminomethyl-6-tert-butoxy-5-methyl-hexanoic acid;
(3S,5S)-3-Aminomethyl-6-fluoromethoxy-5-methyl-hexanoic acid;
(3S,5S)-3-Aminomethyl-6-(2-fluoro-ethoxy)-5-methyl-hexanoic acid;
(3S,5S)-3-Aminomethyl-5-methyl-6-(3,3,3-trifluoro-propoxy)-hexanoic acid;
(3S,5S)-3-Aminomethyl-5-methyl-6-phenoxy-hexanoic acid;
(3S,5S)-3-Aminomethyl-6-(4-chloro-phenoxy)-5-methyl-hexanoic acid;
(3S,5S)-3-Aminomethyl-6-(3-chloro-phenoxy)-5-methyl-hexanoic acid;
(3S,5S)-3-Aminomethyl-6-(2-chloro-phenoxy)-5-methyl-hexanoic acid;
(3S,5S)-3-Aminomethyl-6-(4-fluoro-phenoxy)-5-methyl-hexanoic acid;
(3S,5S)-3-Aminomethyl-6-(3-fluoro-phenoxy)-5-methyl-hexanoic acid;
(3S,5S)-3-Aminomethyl-6-(2-fluoro-phenoxy)-5-methyl-hexanoic acid;
(3S,5S)-3-Aminomethyl-6-(4-methoxy-phenoxy)-5-methyl-hexanoic acid;
(3S,5S)-3-Aminomethyl-6-(3-methoxy-phenoxy)-5-methyl-hexanoic acid;
(3S,5S)-3-Aminomethyl-6-(2-methoxy-phenoxy)-5-methyl-hexanoic acid;
(3S,5S)-3-Aminomethyl-5-methyl 6-(4-trifluoromethyl-phenoxy)-hexanoic acid;
(3S,5S)-3-Aminomethyl-5-methyl 6-(3-trifluoromethyl-phenoxy)-hexanoic acid;
(3S,5S)-3-Aminomethyl-5-methyl 6-(2-trifluoromethyl-phenoxy)-hexanoic acid;
(3S,5S)-3-Aminomethyl-5-methyl 6-(4-nitro-phenoxy)-hexanoic acid;
(3S,5S)-3-Aminomethyl-5-methyl 6-(3-nitro-phenoxy)-hexanoic acid;
(3S,5S)-3-Aminomethyl-5-methyl 6-(2-nitro-phenoxy)-hexanoic acid;
(3S,5S)-3-Aminomethyl-6-benzyloxy-5-methyl-hexanoic acid;
(3S,5R)-3-Aminomethyl-6-cyclopropyl-5-methyl-hexanoic acid;
(3S,5R)-3-Aminomethyl-6-cyclobutyl-5-methyl-hexanoic acid;
(3S,5R)-3-Aminomethyl-6-cyclopentyl-5-methyl-hexanoic acid;
(3S,5R)-3-Aminomethyl-6-cyclohexyl-5-methyl-hexanoic acid;
(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5-methyl-dodecanoic acid;
(3S,5R)-3-Aminomethyl-5,7-dimethyl-octanoic acid;
(3S,5R)-3-Aminomethyl-5,8-dimethyl-nonanoic acid;
(3S,5R)-3-Aminomethyl-5,9-dimethyl-decanoic acid;
(3S,5R)-3-Aminomethyl-5,10-dimethyl-undecanoic acid;
(3S,5S)-3-Aminomethyl-5,6-dimethyl-heptanoic acid;
(3S,5S)-3-Aminomethyl-5,6,6-trimethyl-heptanoic acid;
(3S,5S)-3-Aminomethyl-5-cyclopropyl-hexanoic acid;
(3S,5S)-3-Aminomethyl-6-fluoro-5-methyl-hexanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5S)-3-Aminomethyl-7,7,7-trifluoro-5-methyl-heptanoic acid;
(3S,5R)-3-Aminomethyl-8,8,8-trifluoro-5-methyl-octanoic acid;

(3S,5S)-3-Aminomethyl-5-methyl-6-phenyl-hexanoic acid;
(3S,5S)-3-Aminomethyl-6-(4-chloro-phenyl)-5-methyl-hexanoic acid;
(3S,5S)-3-Aminomethyl-6-(3-chloro-phenyl)-5-methyl-hexanoic acid;
(3S,5S)-3-Aminomethyl-6-(2-chloro-phenyl)-5-methyl-hexanoic acid;
(3S,5S)-3-Aminomethyl-6-(4-methoxy-phenyl)-5-methyl-hexanoic acid;
(3S,5S)-3-Aminomethyl-6-(3-methoxy-phenyl)-5-methyl-hexanoic acid;
(3S,5S)-3-Aminomethyl-6-(2-methoxy-phenyl)-5-methyl-hexanoic acid;
(3S,5S)-3-Aminomethyl-6-(4-fluoro-phenyl)-5-methyl-hexanoic acid;
(3S,5S)-3-Aminomethyl-6-(3-fluoro-phenyl)-5-methyl-hexanoic acid;
(3S,5S)-3-Aminomethyl-6-(2-fluoro-phenyl)-5-methyl-hexanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid;
(3S,5S)-3-Aminomethyl-5-methyl-hept-6-enoic acid;
(3S,5R)-3-Aminomethyl-5-methyl-oct-7-enoic acid;
(3S,5R)-3-Aminomethyl-5-methyl-non-8-enoic acid;
(E)-(3S,5S)-3-Aminomethyl-5-methyl-oct-6-enoic acid;
(Z)-(3S,5S)-3-Aminomethyl-5-methyl-oct-6-enoic acid;
(Z)-(3S,5S)-3-Aminomethyl-5-methyl-non-6-enoic acid;
(E)-(3S,5S)-3-Aminomethyl-5-methyl-non-6-enoic acid;
(E)-(3S,5R)-3-Aminomethyl-5-methyl-non-7-enoic acid;
(Z)-(3S,5R)-3-Aminomethyl-5-methyl-non-7-enoic acid;
(Z)-(3S,5R)-3-Aminomethyl-5-methyl-dec-7-enoic acid; and
(E)-(3S,5R)-3-Aminomethyl-5-methyl-undec-7-enoic acid.

Method 8

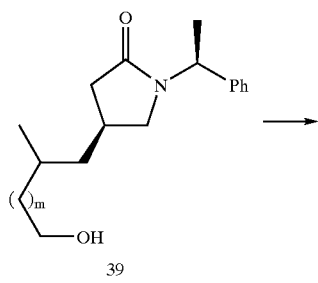

39

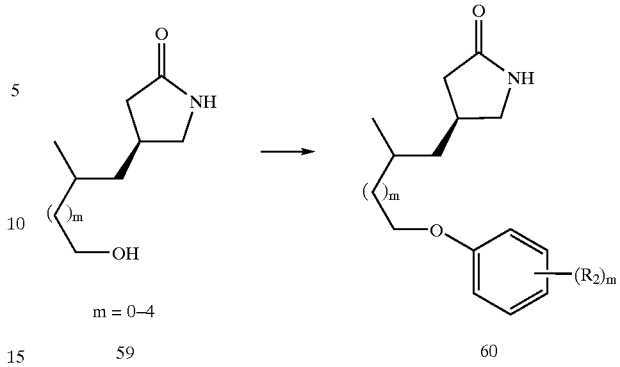

59  60 m = 0–4

A compound of structure 60 can be prepared from a compound of structure 59 through treatment with an appropriately substituted phenol (including phenol itself) under conditions described by Mitsunobu, *Synthesis,* 1981:1.

A compound of structure 59 could be prepared from compound of structure 39 by treatment with sodium or lithium metal and alike in ammonia. Preferably, the reaction is carried out with sodium metal in ammonia.

The direct hydrolysis of compound 60 would give rise to the desired amino acid or the approach via hydrolysis of the Boc protected lactam could be utilized.

Compounds which could be prepared in this manner include:

(3S)-3-Aminomethyl-5-methyl-7-phenoxy-heptanoic acid;
(3S)-3-Aminomethyl-7-(4-chloro-phenoxy)-5-methyl-heptanoic acid;
(3S)-3-Aminomethyl-7-(3-chloro-phenoxy)-5-methyl-heptanoic acid;
(3S)-3-Aminomethyl-7-(2-chloro-phenoxy)-5-methyl-heptanoic acid;
(3S)-3-Aminomethyl-7-(4-fluoro-phenoxy)-5-methyl-heptanoic acid;
(3S)-3-Aminomethyl-7-(3-fluoro-phenoxy)-5-methyl-heptanoic acid;
(3S)-3-Aminomethyl-7-(2-fluoro-phenoxy)-5-methyl-heptanoic acid;
(3S)-3-Aminomethyl-7-(4-methoxy-phenoxy)-5-methyl-heptanoic acid;
(3S)-3-Aminomethyl-7-(3-methoxy-phenoxy)-5-methyl-heptanoic acid;
(3S,)-3-Aminomethyl-7-(2-methoxy-phenoxy)-5-methyl-heptanoic acid;
(3S)-3-Aminomethyl-5-methyl-7-(4-trifluoromethyl-phenoxy)-heptanoic acid;
(3S)-3-Aminomethyl-5-methyl-7-(3-trifluoromethyl-phenoxy)-heptanoic acid;
(3S)-3-Aminomethyl-5-methyl-7-(2-trifluoromethyl-phenoxy)-heptanoic acid;
(3S)-3-Aminomethyl-5-methyl-7-(4-nitro-phenoxy)-heptanoic acid;
(3S)-3-Aminomethyl-5-methyl-7-(3-nitro-phenoxy)-heptanoic acid;
(3S)-3-Aminomethyl-5-methyl-7-(2-nitro-phenoxy)-heptanoic acid;
(3S)-3-Aminomethyl-6-(3-chloro-phenoxy)-5-methyl-hexanoic acid;
(3S)-3-Aminomethyl-6-(2-chloro-phenoxy)-5-methyl-hexanoic acid;
(3S)-3-Aminomethyl-6-(4-fluoro-phenoxy)-5-methyl-hexanoic acid;

(3S)-3-Aminomethyl-6-(3-fluoro-phenoxy)-5-methyl-hexanoic acid;
(3S)-3-Aminomethyl-6-(2-fluoro-phenoxy)-5-methyl-hexanoic acid;
(3S)-3-Aminomethyl-6-(4-methoxy-phenoxy)-5-methyl-hexanoic acid;
(3S)-3-Aminomethyl-6-(3-methoxy-phenoxy)-5-methyl-hexanoic acid;
(3S)-3-Aminomethyl-6-(2-methoxy-phenoxy)-5-methyl-hexanoic acid;
(3S)-3-Aminomethyl-5-methyl 6-(4-trifluoromethyl-phenoxy)-hexanoic acid;
(3S)-3-Aminomethyl-5-methyl 6-(3-trifluoromethyl-phenoxy)-hexanoic acid;
(3S)-3-Aminomethyl-5-methyl 6-(2-trifluoromethyl-phenoxy)-hexanoic acid;
(3S)-3-Aminomethyl-5-methyl 6-(4-nitro-phenoxy)-hexanoic acid;
(3S)-3-Aminomethyl-5-methyl 6-(3-nitro-phenoxy)-hexanoic acid;
(3S)-3-Aminomethyl-5-methyl 6-(2-nitro-phenoxy)-hexanoic acid;
(3S)-3-Aminomethyl-5-methyl-6-phenoxy-hexanoic acid; and
(3S)-3-Aminomethyl-6-(4-chloro-phenoxy)-5-methyl-hexanoic acid.

Method 9 Synthesis of C-4 Substituted Analogs

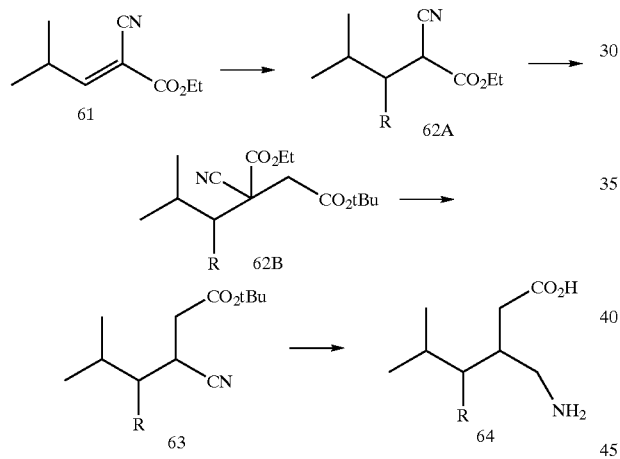

A compound of structure 64 could be prepared from compound of structure 63 by treatment of 63 with hydrogen at 50 psi in the presence of a catalyst such as such as Raney nickel in the presence of a base such as triethyl amine in an organic solvent for example methanol. The resulting product is then treated with an aqueous acid such as 6N HCl at a temperature between room temperature and reflux. The resulting mixture could be subjected to ion exchange chromatography to isolate the product 64.

A compound of structure 63 can be prepared from a compound of structure 62B by treatment with an appropriate base, such as but not limited too sodium hydride, n-butyl lithium and alike, and an alkylating reagent such as t-butylbromoacetate or benzylbromoacetate in a solvent such as DMSO or THF an alike. Preferably, the reaction is carried out by treating a solution of a compound of structure 62B in THF with sodium hydride and alkylation of the resultant anion with t-butylbromoaceate.

A compound of structure 62B can be prepared from a compound of structure 62A by treatment with sodium chloride in a solvent such as aqueous DMSO at a temperature between 50° C. and reflux.

A compound of structure 62A can be prepared from a compound of structure 61 by treatment with an appropriate alkylmetalhalide such as an alkyllithium reagent or an organomagnesium halide in a solvent such as THF or ether in the presence of a copper salt, such as but not limited to copper iodide, copper bromide dimethylsulphide. Alternatively, the reaction may be carried out by the treatment of the nitrile in a solvent such as ether at, or below, room temperature with an alkylmagenisum chloride.

A compound such as 61 can be prepared according to known literature procedures between the condensation of isobutylaldheyde and methylcyanoacetate.

Method 10
C-4 Substitution

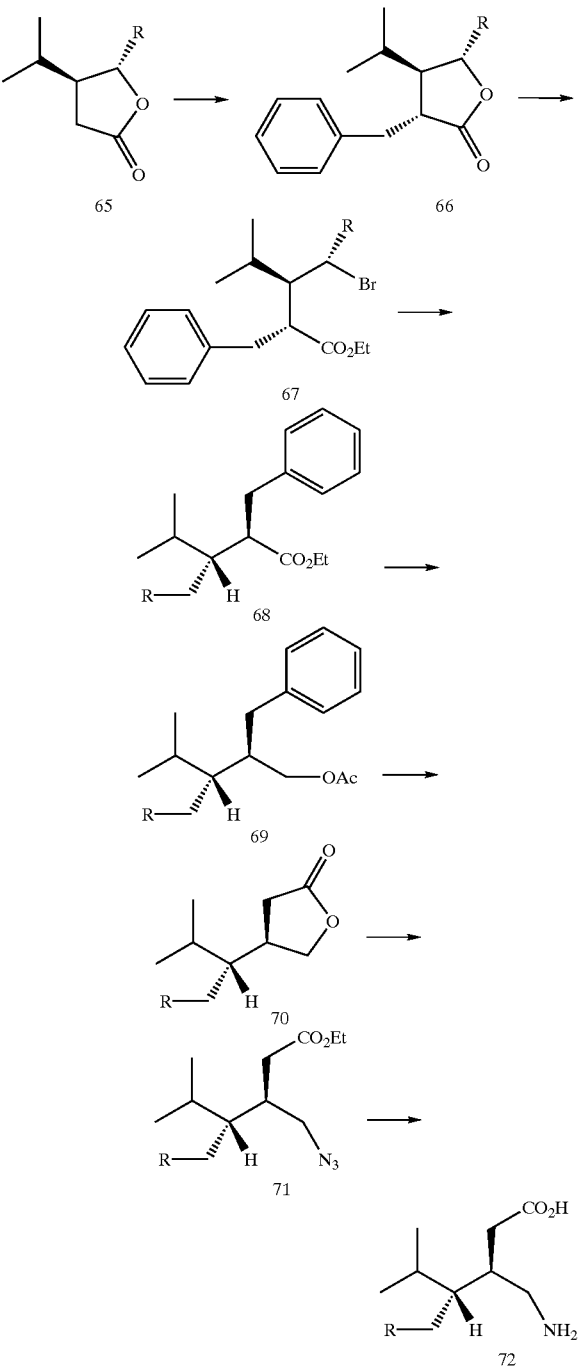

Doubly branched 3-substituted GABA analogs 72 can be prepared in two steps from the azide 71 through hydrogenation of the azide 71 in the presence of a noble metal catalyst such as 5% palladium on carbon and hydrolysis of the resulting lactam with a strong acid such as 6 N HCl at Specific Examples

Example 3

Synthesis of 3-Aminomethyl-5-methyl-octanoic acid

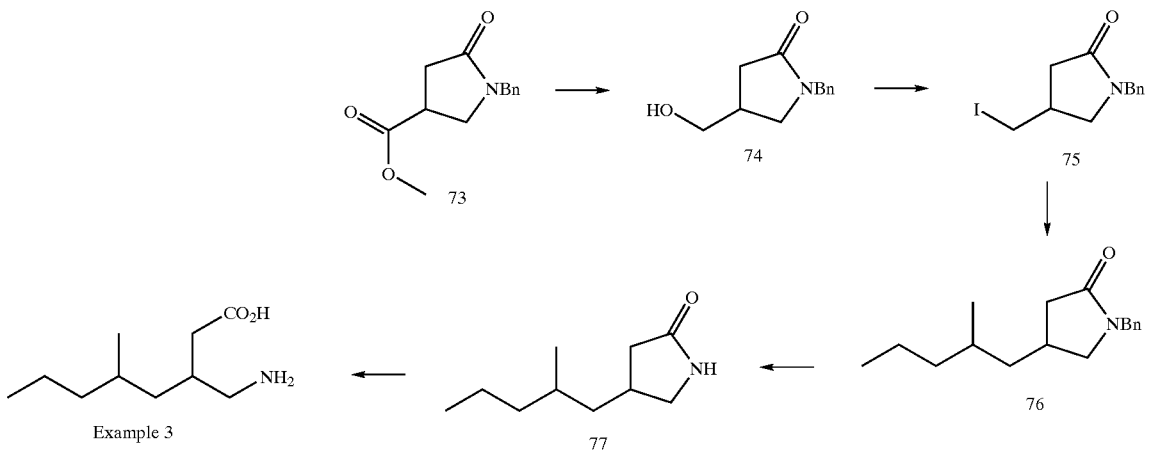

reflux. The final product 72 can then be isolated using ion exchange chromatography.

Compound 71 can be prepared in two steps by treatment of a lactone such as 70 with HBr in a solvent such as ethanol at a temperature such as 0° C. and reacting the resulting bromide with sodium azide in a solvent such as dimethyl sulfoxide at a temperature between 10° C. and 80° C.

Lactone 70 can be prepared in two steps by oxidation of a compound such as 69 with an oxidant such as sodium periodate in the presence of a catalytic amount of ruthenium trichloride in a solvent such as acetonitrile at a temperature between 0° C. and 100° C. and treatment of the resulting compound with potassium carbonate in methanol followed at a temperature between 25° C. and 70° C. and then treatment with an acid such as p-toluene sulfonic acid in a solvent such as THF at reflux or an aqueous acid such as HCl in water at ambient temperature.

A compound such as 69 can be prepared by a by reduction of a compound such as 68 with a hydride reducing agent such as lithium aluminum hydride in a solvent such as ether or THF and reaction of the resulting alcohol with an acylating agent such as acetic anhydride in the presence of a base such as triethyl amine or pyridine or the like.

Compounds of structure 68 can be prepared by reaction of a compound such as 67 with hydrogen at approximately 50 psi in the presence of a noble metal catalyst such as 5% palladium on carbon in a solvent such as ethanol. A compound of the formula 67 can be prepared by reaction of a compound of structure 66 with a solution of ethanol saturated with hydrogen bromide gas. A compound such as 66 can be prepared from a compound such as 65 by treatment of a compound such as one with a strong base such as lithium diisopropyl amine in a solvent such as THF at a temperature such as −78° C. and reaction of the resulting anion with a compound such as benzyl bromide or benzyl iodide. Compounds of the structure 66 (R=H or loweralkyl) can be prepared in optical form from methods known in the literature (Davies, *J. Org. Chem.,* 1999;64(23):8501–8508; Koch *J. Org. Chem.,* 1993;58(10):2725–37; Afonso, *Tetrahedron,* 1993;49(20):4283–92; Bertus, *Tetrahedron, Asymmetry* 1999;10(7):1369–1380; Yamamoto, *J. Am. Chem. Soc.,* 1992;114(20):7652–60).

1-Benzyl-4-hydroxymethyl-pyrrolidine-2-one 74

Sodium borohydride (8.0 g, 0.211 mol) was added to a solution of methyl-1-benzyl-5-oxo-3-pyrrolidnecarboxylate 73 (See Zoretic et al, *J. Org. Chem.,* 1980;45:810–814 for general method of synthesis) (32.0 g, 0.137 mol) in 1,2-dimethoxyethane (600 mL) and refluxed for 19 hours. The reaction was cooled to room temperature and 200 mL of water was added. The reaction was quenched with 1 M citric acid and concentrated under reduced pressure. The residue was extracted with dichloromethane, dried over magnesium sulfate, and evaporated to dryness to give 17.47 g, 62% of the alcohol 74 as clear oil. $^1$H NMR (CDCl$_3$) δ7.30 (m, 5H), 4.38 (d, 1H, J=14.7), 4.46 (d, 1H, J=14.7), 3.56 (m, 2H), 3.36 (m, 1H), 3.10 (m, 1H), 2.52 (m, 2H), 2.26 (m, 1H). MS, m/z (relative intensity): 207 [M+2H, 66%]. IR (KBr) 3345, 2946, 2866, 1651, 1445, 1025, 737, and 698 cm$^{-1}$.

1-Benzyl-4-iodomethyl-pyrrolidin-2-one 75

To alcohol lactam 74 (11.18 g, 0.056 mol) in 210 mL toluene was added in turn, triphenylphosphine (20.0 g, 0.076 mol), imidazole (10.8 g, 0.159 mol), and iodine (19.0 g, 0.075 mol). After stirring the suspension for 1.5 hours, the supernatant was poured into another flask. The sticky yellow residue was washed twice with ether and the solutions were combined. The solvent was evaporated and the residue was chromatographed on silica, eluting with 1:1 acetone/hexane to give 7.92 g, 46% of the iodolactam 75 as yellow oil. $^1$H NMR (CDCl$_3$) δ7.25 (m, 5H), 4.38 (d, 1H, J=14.6), 4.46 (d, 1H, J=14.6), 3.38 (dd, 1H, J=7.8 and 2.2), 3.20 (dd, 1H, J=5.6 and 4.4), 3.12 (dd, 1H, J=7.3 and 2.4), 2.96 (dd, 1H, J=5.8 and 4.4), 2.60 (m, 2H), 2.22 (dd, 1H, J=10.5 and 9.7). MS, m/z (relative intensity): 224 [M−H−Bn, 94%], 317 [M+2H, 64%]. IR 3027, 2917, 1688, 1438, 1267, and 701 cm$^{-1}$.

1-Benzyl-4-(2-methyl-pentyl)-pyrrolidin-2-one 76

To a suspension of magnesium turnings (0.50 g, 0.021 mol) in 15 mL of dry THF under nitrogen, was added an iodine crystal and 2-bromopentane (2.88 g, 0.019 mol). After an exothermic reaction which was periodically cooled in an ice bath, the reaction was stirred at room temperature for 2 hours. Eight milliliters of Li$_2$CuCl$_4$ (made from 84 mg LiCl and 134 mg CuCl$_2$ in 10 mL of dry THF) was added at 0° C. followed by dropwise addition of 1-Benzyl-4-iodomethyl-pyrolidine-2-one 75 in 15 mL dry THF, and the resulting suspension was let stir at 0° C. for 3 hours. Stirring was continued at room temperature for 1 hour before quenching with a saturated solution of ammonium chloride. Water was added to dissolve the precipitate formed, and the solution was then extracted with ether and dried over magnesium sulfate. The solvent was evaporated under vacuum and the residue chromatographed on silica eluting with 1:1 acetone/hexane to give 1.13 g, 69% of the 1-benzyl-4-(2-methyl-pentyl)-pyrrolidin-2-one 76. $^1$H NMR (CDCl$_3$) δ7.30 (m, 5H), 4.44 (m, 2H), 3.32 (m, 1H), 2.86 (m, 1H), 2.56 (m, 1H), 2.40 (m, 1H), 2.10 (m, 1H), 1.30 (m, 6H), 1.10 (m, 1H), 0.90 (m, 6H). MS, m/z (relative intensity): 261 [M+2H, 100%], 301 [M−H+CH$_3$CN, 82%], 260 [M+H, 72%].

4-(2-Methyl-pentyl)-pyrrolidin-2-one 77

A 250 mL 3-neck flask equipped with a dry ice condenser was chilled to −78° C. Ammonia (80 mL) was condensed into the flask and 1-benzyl-4-(2-methyl-pentyl)-pyrrolidin-2-one 76 (1.67 g, 0.006 mol) in 15 mL THF was added. Freshly cut sodium beads were added until a deep blue color persisted. The cooling bath was removed and the reaction stirred at reflux (−33° C.) for 1 hour. The reaction was quenched with ammonium chloride and the excess ammonia was allowed to evaporate. The resulting residue was diluted with water, extracted with dichloromethane, and dried over magnesium sulfate. Evaporation of the solvent followed by chromatography on silica eluting with 1:1 acetone/hexane gave 0.94 g, 86% of the 4-(2-Methyl-pentyl)-pyrrolidin-2-one 77. $^1$H NMR (CDCl$_3$) δ6.25 (br, 1H), 3.44 (m, 1H), 2.95 (m, 1H), 2.54 (m, 1H), 2.40 (m, 1H), 1.98 (m, 1H), 1.30 (m, 6H), 0.80 (m, 6H). MS, m/z (relative intensity): 212 [M+2H+CH$_3$CN, 100%], 171 [M+2H, 72%], 170 [M+1H, 65%].

3-Aminomethyl-5-methyl-octanoic acid (Example 3)

The 4-(2-methyl-pentyl)-pyrrolidin-2-one 77 (0.94 g, 0.007 mol) was dissolved in 70 mL of 6N HCl and refluxed for 20 hours. The solution was evaporated under vacuum and an aqueous solution of the residue was applied to Dowex 50WX 8-100 (strongly acidic) ion exchange resin that had been washed with HPLC grade water. The column was eluted, first with water until the eluent was at constant pH, and then with 5% ammonium hydroxide solution. The ammonium hydroxide fractions were evaporated and azeotroped with toluene. The white solid was washed with acetone filtered and dried in a vacuum oven for 24 hours to give the amino acid 0.61 g, 59%. $^1$H NMR (CD$_3$OD) δ3.00 (m, 1H), 2.85 (m, 1H), 2.48 (m, 1H), 2.30 (m, 1H), 2.14 (brm, 1H), 1.60 (brm, 1H), 1.38 (m, 4H), 1.18 (m, 2H), 0.60 (m, 6H). MS, m/z (relative intensity): 188 [M+H, 100%].

Example 4

Synthesis of 3-Aminomethyl-5,7-dimethyl-octanoic acid

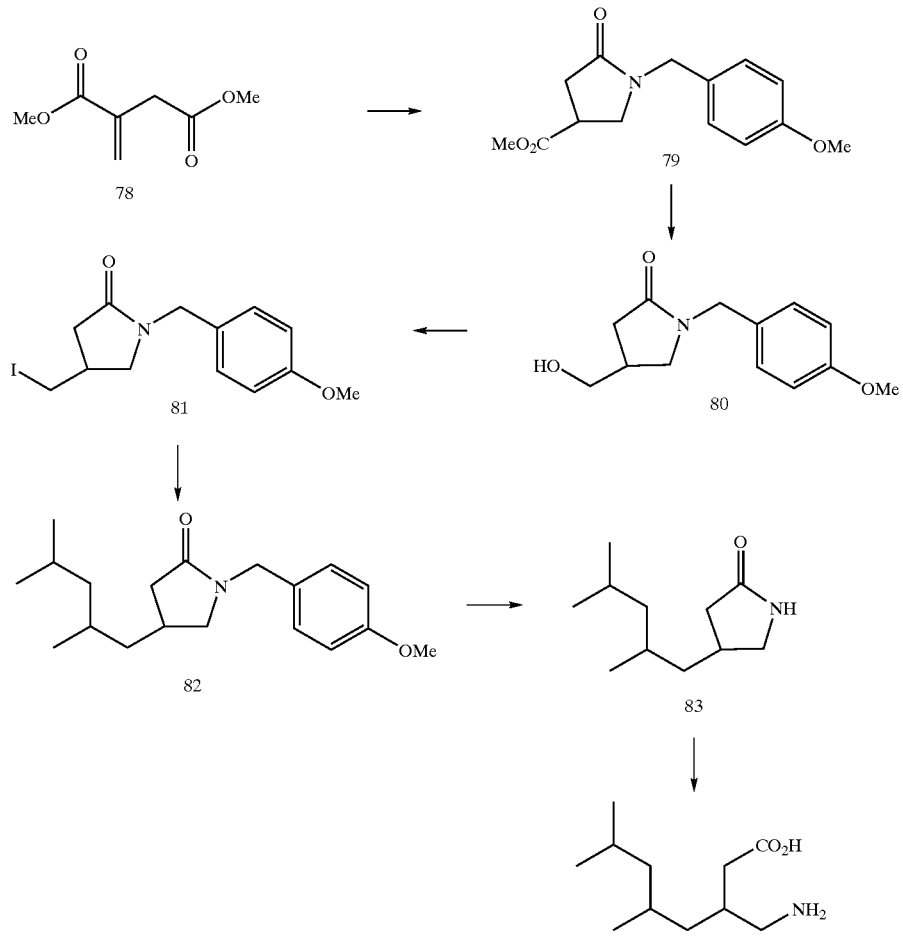

Example 4

1-(4-Methoxy-benzyl)-5-oxo-pyrrolidine-3-carboxylic acid methyl ester 79

To 4-methoxybenzylamine (42 g, 0.306 mol) in methanol (40 mL) at 0° C. was added the dimethyl itaconate (48 g, 0.306 mol) in methanol (13 mL). The solution was stirred at room temperature for 4 days. 1N HCl was added to the solution followed by ether. The two layers were separated and the aqueous phase extracted with ether. The combined organic phases were dried (MgSO$_4$). Upon filtration of the drying agent the desired material 79 precipitated from solution that was collected and dried under vacuum. 23.26 g, 29%. MS, m/z (relative intensity): 264 [M+H, 100%]. Anal. Calcd for $C_{14}H_{17}N_1O_4$: C, 63.87; H, 6.51; N, 5.32. Found: C, 63.96; H, 6.55; N, 5.29.

4-Hydroxymethyl-1-(4-methoxy-benzyl)-pyrrolidine-2-one 80

NaBH$_4$ (15 g, 0.081 mol) was added in portions to ester 79 in ethanol (600 mL) at room temperature. After 4.5 hours water (~200 mL) was carefully added to the reaction and the solution stirred at room temperature overnight. The resultant solid was removed by filtration and the filtrate concentrated to give alcohol 80 as an oil. 15.33 g, 81%. MS, m/z (relative intensity): 235 [M+H, 100%].

4-(2,4-Dimethyl-pentyl)-1-(4-methoxy-benzyl)-pyrrolidin-2-one 82

A procedure similar to the preparation of 1-benzyl-4-(2-methyl-pentyl)-pyrrolidin-2-one 76 was utilized to give 4-(2,4-dimethyl-pentyl)-1-(4-methoxy-benzyl)-pyrrolidin-2-one as an oil. 1.22 g, 29%. MS, m/z (relative intensity): 304 [M+H, 100%].

4-(2,4-Dimethyl-pentyl)-pyrrolidin-2-one 83

To the lactam (1.17 g, 3.86 mmol) in MeCN (20 mL) at 0° C. was added ceric ammonium nitrate (4.2 g, 7.7 mmol) in H$_2$O (10 mL). After 50 minutes a further portion of ceric ammonium nitrate (2.1 g, 3.86 mmol) was added, and after 1 hour the mixture was absorbed onto silica and flash chromatographed to give an oil. MS, m/z (relative intensity): 183 [M+H, 100%].

3-Aminomethyl-5,7-dimethyl-octanoic acid (Example 4)

A procedure similar to the preparation of 3-aminomethyl-5-methyl-octanoic acid (Example 3) was utilized to give the amino acid as a solid. MS, m/z (relative intensity): 202 [M+H, 100%].

Example 5

Synthesis of (S)-3-Aminomethyl-5-methyl-octanoic acid

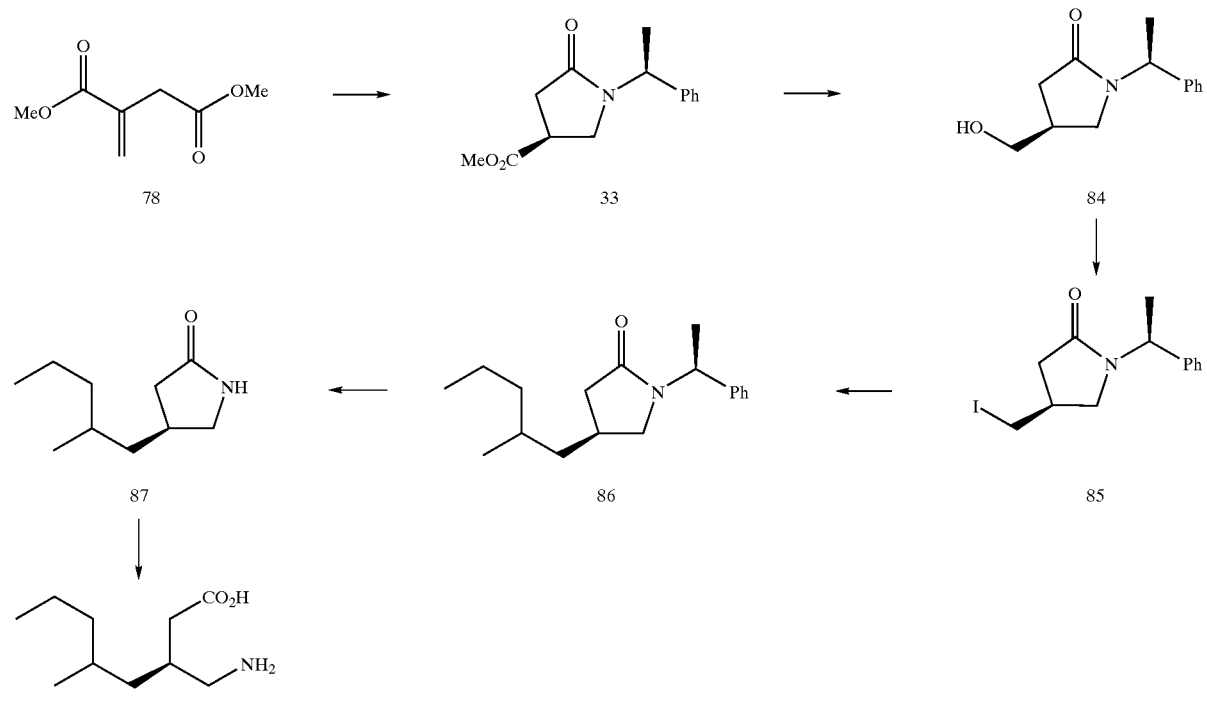

Example 5

4-Iodomethyl-1-(4-methoxy-benzyl)-pyrrolidin-2-one 81

To alcohol 80 (12.9 g, 0.055 mol) in PhMe was added triphenylphosphine (20 g, 0.077 mol), imidazole (10.8 g, 0.16 mol), and iodine (19 g, 0.075 mol). The suspension was stirred at room temperature 5 hours. A saturated aqueous solution of sodium thiosulphate was added and the two layers separated. The aqueous phase was extracted with ether and the combined organic phases washed with brine, dried (MgSO$_4$) and concentrated. Flash chromatography (6:1 to 4:1 toluene/acetone) of the residue gave iodide 81 as an oil. 11.9 g, 63%. MS, m/z (relative intensity): 346 [M+H, 100%].

(S)-4-Hydroxymethyl-1-((S)-1-phenyl-ethyl)-pyrrolidin-2-one 84

To the ester 33 (49 g, 0.198 mol) in EtOH (600 mL) was added sodium borohydride (22 g, 0.595 mol). After 7 hours, 1 M citric acid was carefully added and, after effervescence had ceased, water was added to fully quench the reaction. The ethanol was removed under reduced pressure and ethyl acetate added. The resultant two layers were separated, the aqueous phase was extracted with EtOAc, and the combined organic phases dried (MgSO$_4$) and concentrated to give a heavy oil. MS, m/z (relative intensity): [M+H, 100%].

(S)-4-Iodomethyl-1-((S)-1-phenyl-ethyl)-pyrrolidin-2-one 85

A procedure similar to the iodination of compound 80 was utilized giving iodide 85 as an oil. 35.2 g, 56%. Anal. Calcd for $C_{13}H_{16}I_1N_1O_1$: C, 47.43; H, 4.90; N, 4.25. Found: C, 47.41; H, 4.83; N, 4.17.

4-(2-Methyl-pentyl)-1-((S)-1-phenyl-ethyl)-pyrrolidin-2-one 86

A procedure similar to the preparation of 1-benzyl-4-(2-methyl-pentyl)-pyrrolidin-2-one 76 was utilized to give 2.71 g, 81.0% of 86 as an oil. MS, m/z (relative intensity): 274 [M+1H, 100%], 315 [M+H+CH$_3$CN, 65%].

(S)-4-(2-Methyl-pentyl)-pyrrolidin-2-one 87

A procedure similar to the preparation of 4-(2-methyl-pentyl)-pyrrolidin-2-one 77 was used to give 1.14 g, 72.8% of 87 as an oil. MS, m/z (relative intensity): 170 [M+1H, 10%], 211 [M+1H+CH$_3$CN, 90%].

Example 5
(S)-3-Aminomethyl-5-methyl-octanoic acid

A procedure similar to the preparation of 3-aminomethyl-5-methyl-octanoic acid (Example 3) was used to give the amino acid (example 5) 0.88 g, 74.3%. $^1$H NMR (CD$_3$OD) δ2.95 (m, 1H), 2.80 (m, 1H), 2.40 (m, 1H), 2.25 (m, 1H), 2.05 (brm, 1H), 1.50 (brm, 1H), 1.30 (m, 4H), 1.10 (m, 2H), 0.90 (m, 6H). MS, m/z (relative intensity): 188 [M+1H, 100%], 186 [M−1H, 100%], 229 [M+1H+CH$_3$CN, 30%].

Example 6
Synthesis of (S)-3-Aminomethyl-7-methoxy-5-methyl-heptanoic acid (S)-4-(4-Hydroxy-2-methyl-butyl)-1-((S)-1-phenyl-ethyl)-pyrrolidin-2-one 89

OsO$_4$ (2 mL of a 4% wt solution in t-BuOH) was added to the alkene 88 (5.8 g, 0.021 mol) in THF/H$_2$O (3:1, 100 mL). After 1 hour, sodium periodate (11.4 g, 0.053 mol) was added. After 2 hours, the suspension was filtered and the solids washed with dichloromethane. The filtrate was concentrated and the residue azeotroped with toluene. The residue was dissolved in ethanol and sodium borohydride (2.5 g) added. The suspension was stirred at room temperature overnight. 1N citric acid was added and the mixture diluted with ether. The resultant two layers were separated and the aqueous phase was extracted with ether and the combined organic dried (MgSO$_4$) and concentrated. Flash chromatography (1:1 hexane/EtOAc) of the residue gave an oil. 4.2 g, 73%. MS, m/z (relative intensity): 276 [M+H, 100%].

(S)-4-(4-Methoxy-2-methyl-butyl)-1-((S)-1-phenyl-ethyl)-pyrrolidin-2-one 90

To alcohol 89 (2 g, 7.66 mmol) in DMSO (60 mL) at room temperature was added NaH (368 mg, 60% in oil). After 30 minutes the methyl iodide (1.08 g, 7.66 mmol) was added and the solution stirred at room temperature overnight, upon which the reaction was diluted with water (500 mL). The solution was extracted with ether, and the combined organic extracts were dried (MgSO$_4$) and concentrated. Flash chromatography (90% to 50% hexane/acetone) of the residue gave the product 90 as an oil (1.1 g, 52%). MS m/z 290 (M+H, 100%).

(S)-4-(4-Methoxy-2-methyl-butyl)-pyrrolidin-2-one 91

A procedure similar to the synthesis of 4-(2-methyl-pentyl)-pyrrolidin-2-one 77 was utilized giving lactam 91 as an oil. MS m/z 186 (M+H, 100%).

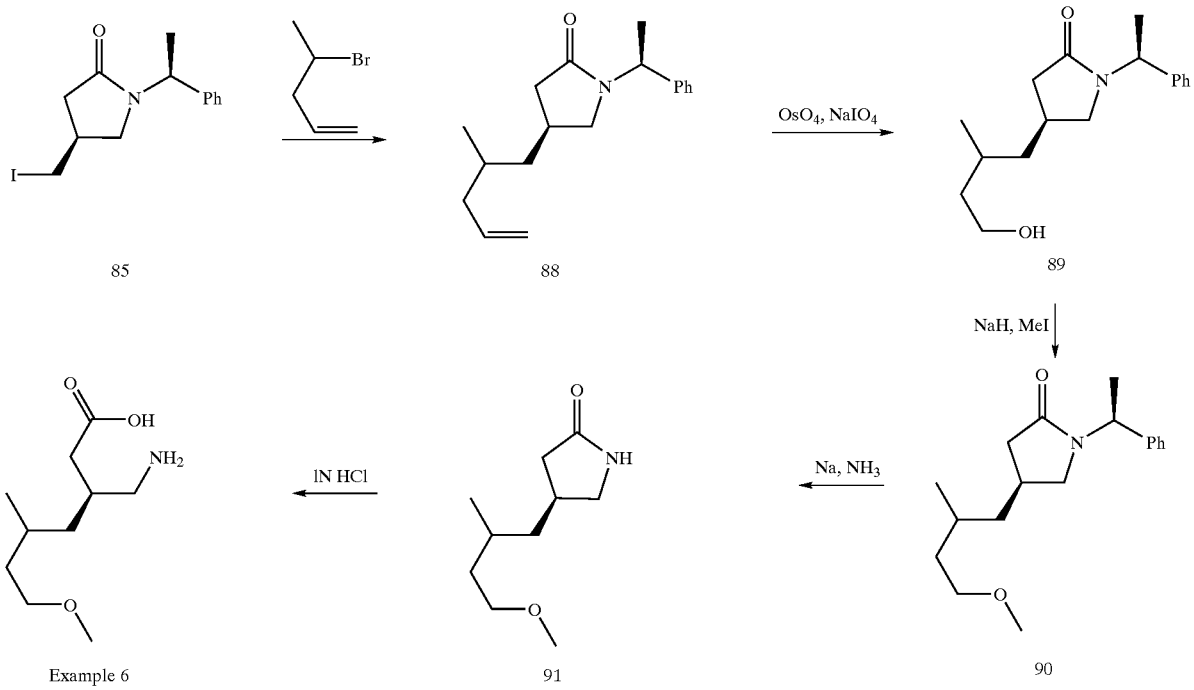

(S)-4-(2-Methyl-pent-4-enyl)-1-((S)-1-phenyl-ethyl)-pyrrolidin-2-one 88

A procedure similar to the preparation of 1-benzyl-4-(2-methyl-pentyl)-pyrrolidin-2-one 76 was followed giving the adduct 88 as an oil. 6 g, 74%. MS, m/z (relative intensity): 272 [M+H, 100%].

Example 6
(S)-3-Aminomethyl-7-methoxy-5-methyl-heptanoic acid

A procedure similar to the synthesis of example 3 was followed. The resultant amino acid isolated from ion-exchange chromatography was recrystallized from methanol/ethyl acetate to give the example 6 as a white solid. MS m/z 204 (M+H, 100%). Anal. Calcd for C$_{10}$H$_{21}$N$_1$O$_3$: C, 59.09; H, 10.41; N, 6.89. Found: C, 58.71; H, 10.21; N, 6.67.

Example 7
Synthesis of (S)-3-Aminomethyl-6-fluoro-5-methyl-hexanoic acid

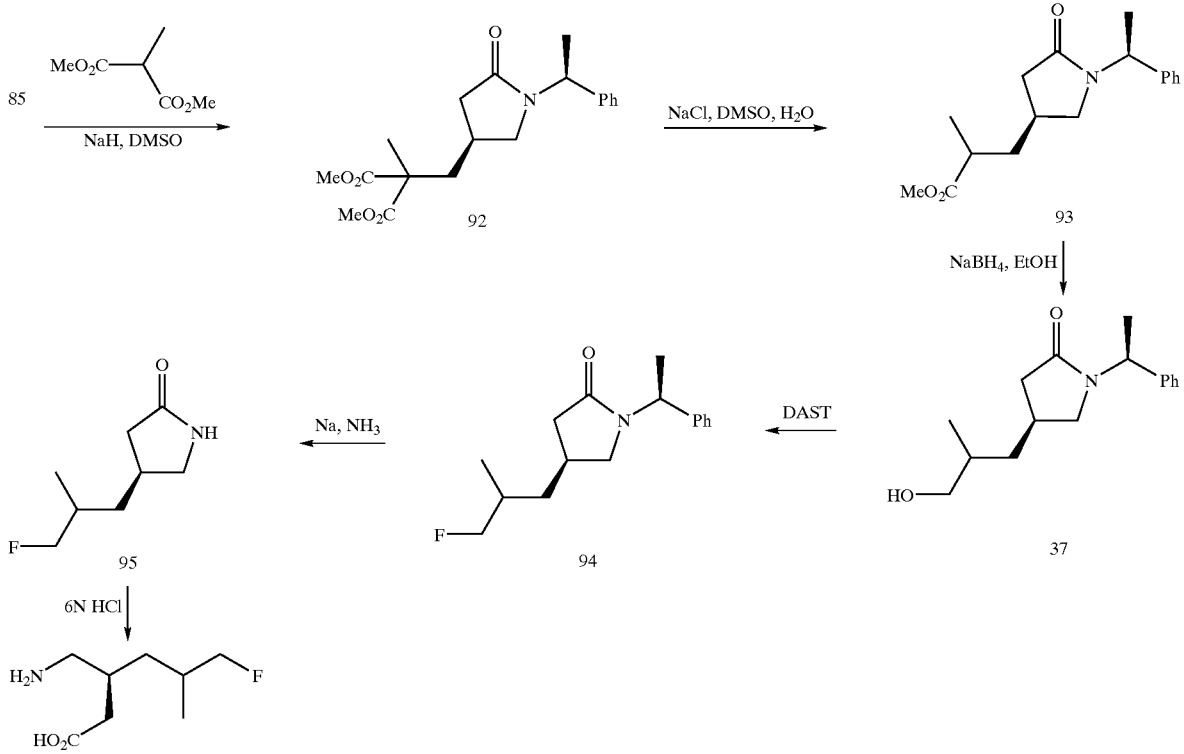

Example 7

2-Methyl-2-[(S)-5-oxo-1-((S)-1-phenyl-ethyl)-pyrrolidin-3-ylmethyl]-malonic acid dimethyl ester 92

To dimethyl methylmalonate (1.06 g, 7.29 mmol) in DMSO (7 mL) at room temperature was added NaH (291 mg of a 60% dispersion in oil). After the effervescence had ceased the lactam 85 (2 g, 7.29 mol) in DMSO (5 mL) was added. After 1 hour water was added and the aqueous solution extracted with ether. The combined organic extracts were dried (MgSO$_4$) and concentrated. Flash chromatography (1:1 hexane/acetone) of the residue gave the product as an oil (1.7 g, 81%). MS m/z 348 (M+H, 100%).

2-Methyl-3-[(S)-5-oxo-1-((S)-1-phenyl-ethyl)-pyrrolidin-3-yl]-propionic acid methyl ester 93

The ester 92 (483 mg, 1.4 mmol), NaCl (104 mg, 1.8 mmol), water (105 µL) and DMSO (5 mL) were heated to reflux for 2 hours. The solution was cooled to room temperature water was added and the aqueous solution extracted with ether. The combined organic extracts were dried (MgSO$_4$) and concentrated. Flash chromatography (80% to 66% hexane/acetone) of the residue gave the product as an oil (160 mg, 40%). MS m/z 290 (M+H, 100%).

(S)-4-(3-Hydroxy-2-methyl-propyl)-1-((S)-1-phenyl-ethyl)-pyrrolidin-2-one 37

To the ester 93 (4.82 g, 0.017 mol) in EtOH (100 mL) was added NaBH$_4$ (3.7 g, 0.10 mol) and the mixture heated to reflux for 2.5 hours. The solution was cooled to 0° C. and 1 M citric acid carefully added followed by water. The solution was concentrated to half volume added and extracted with ether. The combined organic extracts were dried (MgSO$_4$) and concentrated. Flash chromatography (1:1 hexane/acetone) of the residue gave the product as an oil (2.6 g, 59%). MS m/z 262 (M+H, 100%).

(S)-4-(3-Fluoro-2-methyl-propyl)-1-((S)-1-phenyl-ethyl)-pyrrolidin-2-one 94

To DAST (1 g, 6.2 mmol) in CH$_2$Cl$_2$ (20 mL) at −78° C. was added the alcohol 37 in CH$_2$Cl$_2$ (10 mL). After 1 hour at −78° C. the solution was warmed to room temperature. After 7 hours the solution was carefully quenched with a saturated aqueous solution of sodium bicarbonate and the two layers separated. The organic phase was dried (MgSO$_4$) and concentrated. Flash chromatography (90% to 66% hexane/acetone) of the residue gave the product as an oil (600 mg, 37%). MS m/z 264 (M+H, 100%).

(S)-4-(3-Fluoro-2-methyl-propyl)-pyrrolidin-2-one 95

A procedure similar to the preparation of 4-(2-methyl-pentyl)-pyrrolidin-2-one 77 was utilized affording the lactam as an oil (242 mg, 68%). MS m/z 159 (M, 100%).

Example 7

(S)-3-Aminomethyl-6-fluoro-5-methyl-hexanoic acid

A procedure similar to the synthesis of example 3 was followed. The resultant amino acid isolated from ion-exchange chromatography was recrystallized from methanol/ethyl acetate to give example 7 as a white solid. MS m/z 177 (M, 100%). Anal. Calcd for C$_8$H$_{16}$F$_1$N$_1$O$_2$:0.02 H$_2$O: C, 54.11; H, 9.10; N, 7.89. Found: C, 53.75; H, 9.24; N, 7.72.

Example 8
Synthesis of (S)-3-Aminomethyl-6-methoxy-5-methyl-hexanoic acid

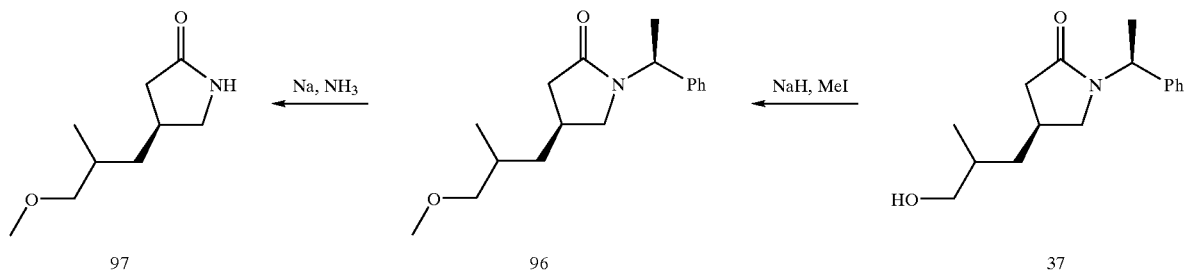

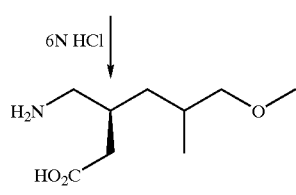

(S)-4-(3-Methoxy-2-methyl-propyl)-1-((S)-1-phenyl-ethyl)-pyrrolidin-2-one 96

A procedure similar to the synthesis of (S)-4-(4-methoxy-2-methyl-butyl)-1-((S)-1-phenyl-ethyl)-pyrrolidin-2-one 90 was utilized giving ether 96 as an oil (90 mg, 37%). MS m/z 276 (M+H, 100%).

(S)-4-(3-Methoxy-2-methyl-propyl)-pyrrolidin-2-one 97

A procedure similar to the synthesis of 4-(2-methyl-pentyl)-pyrrolidin-2-one 77 was utilized giving 97 as an oil (760 mg, 93%). MS m/z 171 (M+H, 100%).

Example 8
(S)-3-Aminomethyl-6-methoxy-5-methyl-hexanoic acid

A procedure similar to the synthesis of example 3 was followed. The resultant amino acid isolated from ion-exchange chromatography was recrystallized from methanol/ethyl acetate to give Example 8 as a white solid. MS m/z 190 (M+H, 100%). Anal. Calcd for $C_9H_{19}N_1O_3$: C, 57.12; H, 10.12; N, 7.40. Found: C, 57.04; H, 10.37; N, 7.30. A second batch precipitated from the mother liquors (1:5 ratio of C5 isomers by $^1$H NMR). MS m/z 190 (M+H, 100%).

Example 9
Synthesis of (3S,5R)-3-Aminomethyl-5-methyl-octanoic acid hydrochloride

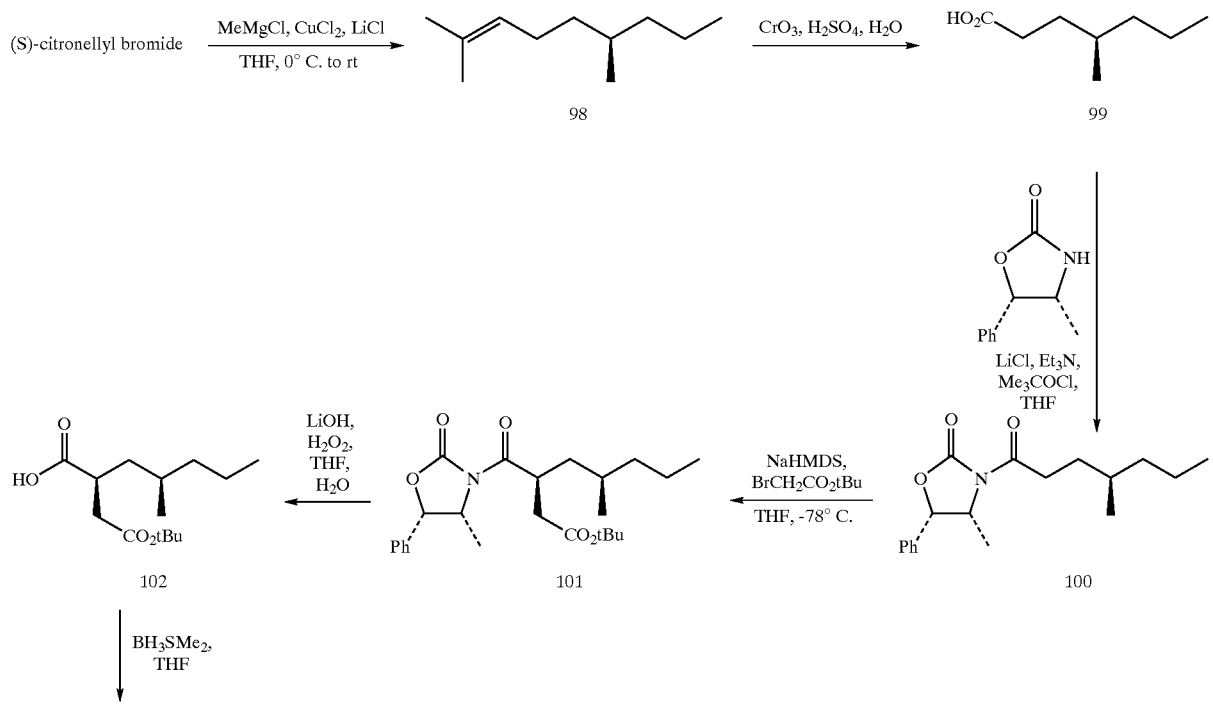

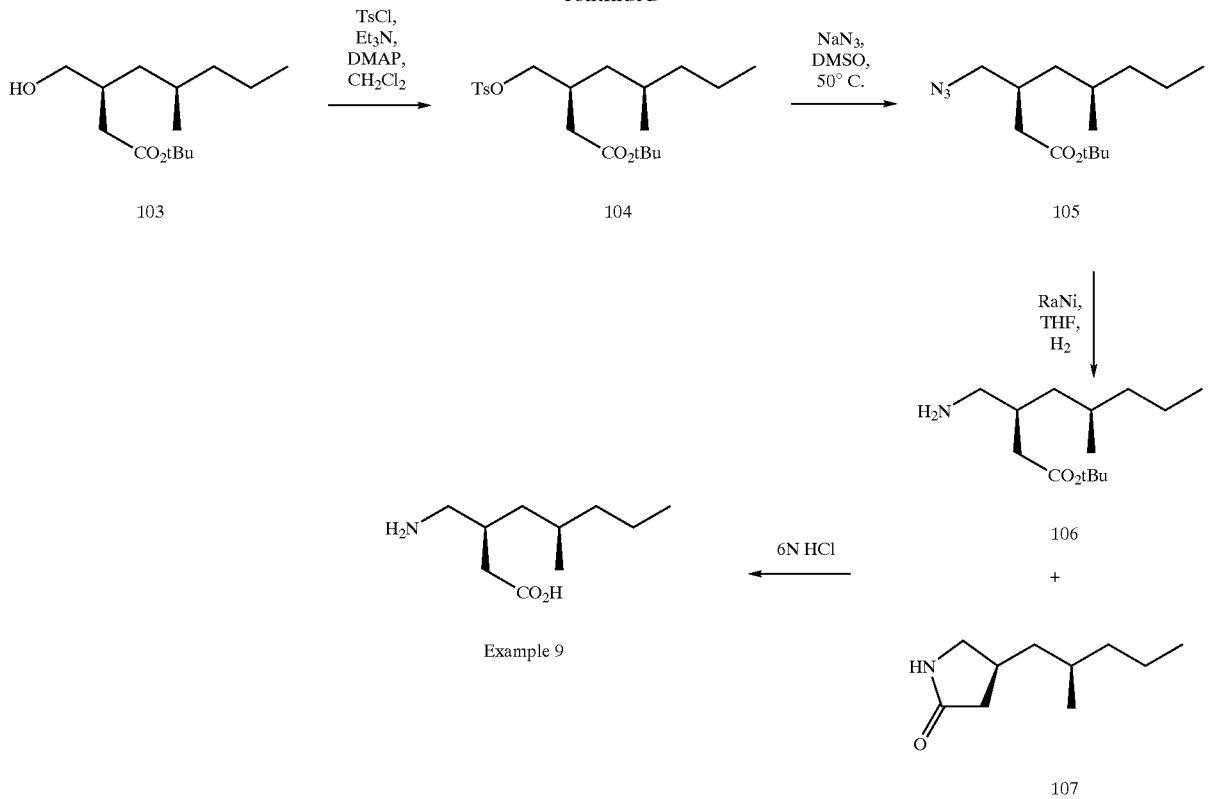

Example 9

(R)-2,6-Dimethyl-non-2-ene 98

To (S)-citronellyl bromide (50 g, 0.228 mol) in THF (800 mL) at 0° C. was added LiCl (4.3 g) followed by CuCl$_2$ (6.8 g). After 30 minutes methylmagnesium chloride (152 mL of a 3 M solution in THF, Aldrich) was added and the solution warmed to room temperature. After 10 hours the solution was cooled to 0° C. and a saturated aqueous solution of ammonium chloride carefully added. The resultant two layers were separated and the aqueous phase extracted with ether. The combined organic phases were dried (MgSO$_4$) and concentrated to give an oil. 32.6 g; 93%. Used without further purification. $^{13}$C NMR (100 MHz; CDCl$_3$) 131.13, 125.28, 39.50, 37.35, 32.35, 25.92, 25.77, 20.31, 19.74, 17.81, 14.60.

(R)-4-Methyl-heptanoic acid 99

To alkene 98 (20 g, 0.13 mol) in acetone (433 mL) was added a solution of CrO$_3$ (39 g, 0.39 mol) in H$_2$SO$_4$ (33 mL)/H$_2$O (146 mL) over 50 minutes. After 6 hours a further amount of CrO$_3$ (26 g, 0.26 mol) in H$_2$SO$_4$ (22 mL)/H$_2$O (100 mL) was added. After 12 hours the solution was diluted with brine and the solution extracted with ether. The combined organic phases were dried (MgSO$_4$) and concentrated. Flash chromatography (gradient of 6:1 to 2:1 hexane/EtOAc) gave the product 99 as an oil. 12.1 g; 65%. MS, m/z (relative intensity): 143 [M−H, 100%].

(4R,5S)-4-Methyl-3-((R)-4-methyl-heptanoyl)-5-phenyl-oxazolidin-2-one 100

To the acid 99 (19 g, 0.132 mol) and triethylamine (49.9 g, 0.494 mol) in THF (500 mL) at 0° C. was added trimethylacetylchloride (20 g, 0.17 mol). After 1 hour LiCl (7.1 g, 0.17 mol) was added followed by the oxazolidinone (30 g, 0.17 mol). The mixture was warmed to room temperature and after 16 hours the filtrate was removed by filtration and the solution concentrated under reduced pressure. Flash chromatography (7:1 hexane/EtOAc) gave the product 100 as an oil. 31.5 g; 79%. [α]$_D$=5.5 (c 1 in CHCl$_3$). MS, m/z (relative intensity): 304 [M+H, 100%].

(3S,5R)-5-Methyl-3-((4R,5S)-4-methyl-2-oxo-5-phenyl-oxazolidine-3-carbonyl)-octanoic acid tert-butyl ester 101

To oxazolidinone 100 (12.1 g, 0.04 mol) in THF (200 ml) at −50° C. was added NaHMDS (48 mL of a 1 M solution in THF). After 30 t-butylbromoaceate (15.6 g, 0.08 mol) was added. The solution was stirred for 4 hours at −50° C. and then warmed to room temperature. After 16 hours a saturated aqueous solution of ammonium chloride was added and the two layers separated. The aqueous phase was extracted with ether and the combined organic phases dried (MgSO$_4$) and concentrated. Flash chromatography (9:1 hexane/EtOAc) gave the product 101 as a white solid 12 g; 72%. [α]$_D$=30.2 (c 1 in CHCl$_3$). $^{13}$C NMR (100 MHz; CDCl$_3$) 176.47, 171.24, 152.72, 133.63, 128.87, 125.86, 80.85, 78.88, 55.34, 39.98, 38.77, 38.15, 37.58, 30.60, 28.23, 20.38, 20.13, 14.50, 14.28.

(S)-2-((R)-2-Methyl-pentyl)-succinic acid 4-tert-butyl ester 102

To ester 101 (10.8 g, 0.025 mol) in H$_2$O (73 mL) and THF (244 ML) at 0° C. was added a premixed solution of LiOH (51.2 mL of a 0.8 M solution) and H$_2$O$_2$ (14.6 mL of a 30% solution). After 4 hours a further 12.8 mL LiOH (0.8 M solution) and 3.65 mL of H$_2$O$_2$ (30% solution) was added. After 30 minutes sodium bisulfite (7 g), sodium sulfite (13 g), and water (60 mL) was added followed by hexane (100 mL) and ether (100 mL). The two layers were separated and the aqueous layer extracted with ether. The combined organic phases were concentrated to an oil that was dissolved in heptane (300 mL). The resultant solid was filtered off and the filtrate dried (MgSO$_4$) and concentrated to afford an oil (6 g, 93%) which was used without further purification. MS, m/z (relative intensity): 257 [M+H, 100%].

(3S,5R)-3-Hydroxymethyl-5-methyl-octanoic acid tert-butyl ester 103

To acid 102 (3.68 g, 0.014 mol) in THF (100 mL) at 0° C. was added $BH_3.Me_2$ (36 mL of a 2 M solution in THF, Aldrich) upon which the solution was warmed to room temperature. After 15 hours ice was carefully added (in order to control the effervescence) to the solution followed by brine. The solution was extracted with ether and the combined organic phases dried ($MgSO_4$) and concentrated under reduced pressure. Flash chromatography (4:1 hexane/EtOAc) gave alcohol 103 as an oil (2.0 g, 59%). $^{13}C$ NMR (100 MHz; $CDCl_3$) 173.56, 80.85, 65.91, 39.74, 39.20, 38.90, 35.65, 29.99, 28.31, 20.18, 19.99, 14.56.

(3S,5R)-5-Methyl-3-(toluene-4-sulfonyloxymethyl)-octanoic acid tert-butyl ester 104

To alcohol 103 (1.98 g, 8.1 mmol) in $CH_2Cl_2$ (40 mL) at room temperature was added triethylamine (2.4 g, 0.024 mol), DMAP (20 mg) and tosyl chloride (2.3 g, 0.012 mol). After 14 hours 1N HCl was added and the two layers separated. The aqueous phase was extracted with ether and the combined organic phases dried ($MgSO_4$) and concentrated. Flash chromatography (95% hexane/EtOAc) gave tosylate 104 as an oil (2.94 g, 91%). $^{13}C$ NMR (100 MHz; $CDCl_3$) 171.60, 144.92, 133.07, 130.02, 128.12, 80.80, 72.15, 39.73, 38.09, 37.89, 32.67, 29.71, 28.22, 21.83, 20.10, 19.54, 14.49.

(3S,5R)-3-Azidomethyl-5-methyl-octanoic acid tert-butyl ester 105

Tosylate 104 (2.92 g, 7.3 mmol) and sodium azide (1.43 g, 0.02 mol) were warmed to ~50° C. in DMSO (30 mL). After 2 hours the solution was cooled to room temperature and diluted with water. The solution was extracted with ether and the combined organic phases dried ($MgSO_4$) and concentrated to give an oil 1.54 g, 79%. Further purification by flash chromatography (95% hexane/EtOAc) gave an oil. $[\alpha]_D=-8.3$ (c 1 in $CHCl_3$). $^{13}C$ NMR (100 MHz; $CDCl_3$) 172.01, 80.73, 54.89, 39.73, 39.46, 39.00, 33.40, 29.85, 28.30, 20.15, 19.82, 14.52.

(S)-4-((R)-2-Methyl-pentyl)-pyrrolidin-2-one 107 and (3S,5R)-3-aminomethyl-5-methyl-octanoic acid tert-butyl ester 106

Azide 105 was treated with 5% Pd/C and shaken under an atmosphere of hydrogen for 20 hours where upon a further 200 mg of 5% Pd/C added. After 6 hours the filtrate was concentrated to afford an oil which by $^1H$ NMR was found to be a mixture of primary amine 106 and lactam 107 (1.75 g) which was used without further purification.

Example 9

(3S,5R)-3-Aminomethyl-5-methyl-octanoic acid hydrochloride

The mixture of the amine 106 and the lactam 107 (1.74 g) was treated with 3N HCl (40 mL) and the solution warmed to 50° C. for 4 hours then cooled to room temperature. After 12 hours the solution was concentrated and the residue recrystallized from ethyl acetate to give the amino acid as a white solid 605 mg. MS, m/z (relative intensity): 188 [M+H, 100%]. Anal. Calcd for $C_{10}H_{21}N_1O_2:H_1Cl_1$ C, 53.68; H, 9.91; N, 6.26. Found: C, 53.83; H, 10.12; N, 6.07.

Example 10

Synthesis of (3S,5R)-3-Aminomethyl-5-methyl-heptanoic acid

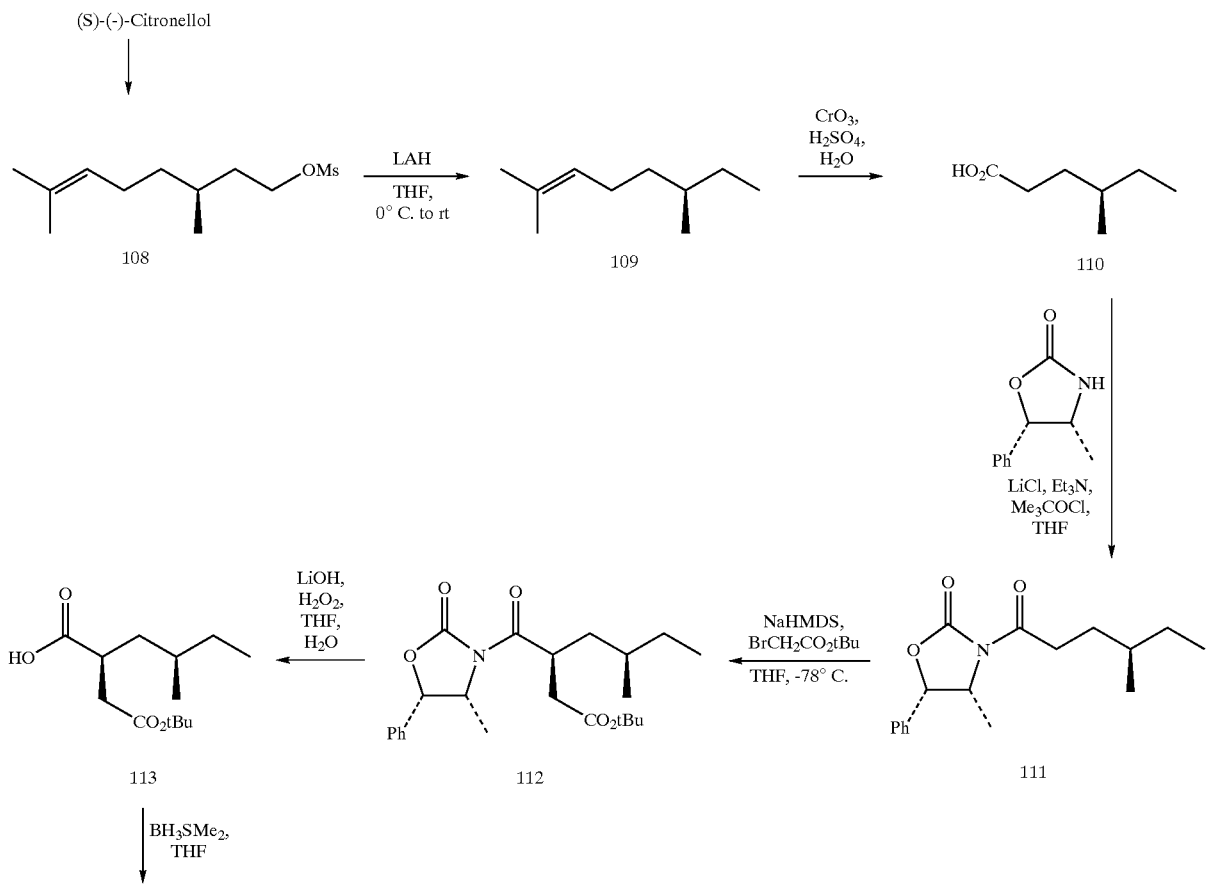

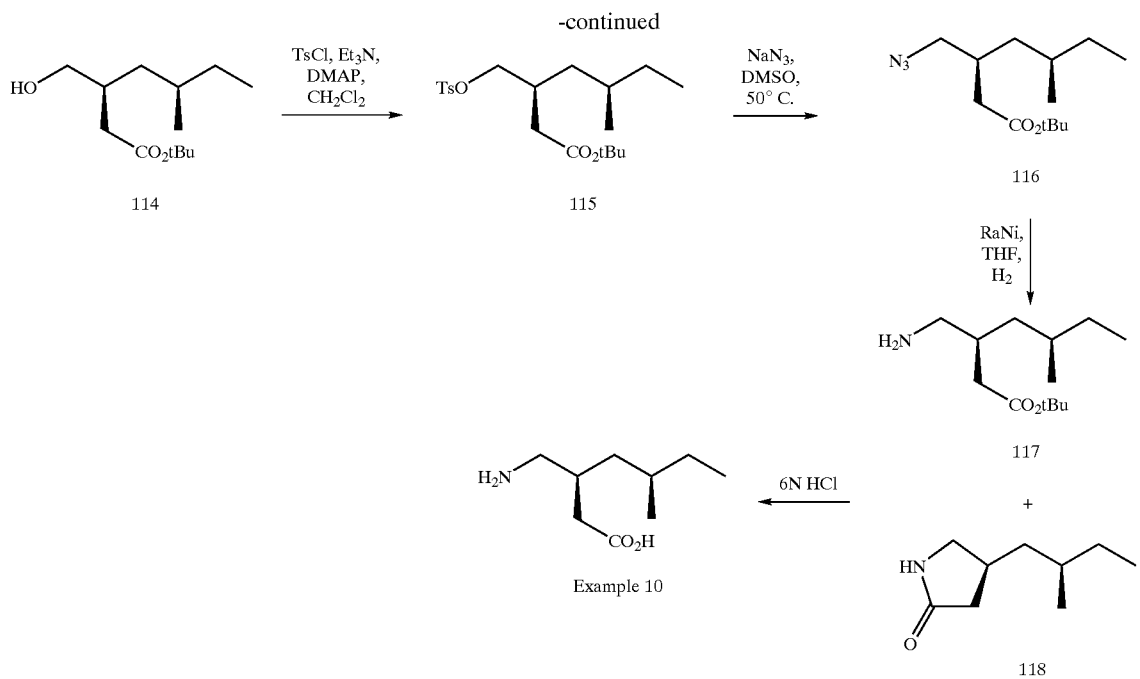

Methanesulfonic acid (S)-3,7-dimethyl-oct-6-enyl ester 108

To S-(−)-citronellol (42.8 g, 0.274 mol) and triethylamine (91 mL, 0.657 mol) in CH$_2$Cl$_2$ (800 mL) at 0° C. was added methanesulphonyl chloride (26 mL, 0.329 mol) in CH$_2$Cl$_2$ (200 mL). After 2 hours at 0° C. the solution was washed with 1N HCl then brine. The organic phase was dried (MgSO$_4$) and concentrated to afford an oil (60.5 g, 94%) which was used without further purification. $^1$H NMR (400 MHz; CDCl$_3$) 5.05 (1H, m), 4.2 (2H, m), 2.95 (3H, s), 1.98 (2H, m), 1.75 (1H, m), 1.6 (3H,s), 1.5 (4H, m), 1.35 (2H, m), 1.2 (1H, m), 0.91 (3H, d, J=6.5 Hz).

(R)-2,6-Dimethyl-oct-2-ene 109

To alkene 108 (60 g, 0.256 mol) in THF (1 L) at 0° C. was added lithium aluminum hydride (3.8 g, 0.128 mol). After 7 hours, a further 3.8 g of lithium aluminum hydride was added and the solution warmed to room temperature. After 18 hours, a further 3.8 g of lithium aluminum hydride was added. After a further 21 hours, the reaction was carefully quenched with 1N citric acid and the solution diluted further with brine. The resultant two phases were separated and the organic phase was dried (MgSO$_4$) and concentrated to afford an oil which was used without further purification. MS, m/z (relative intensity): 139 [M−H, 100%].

(R)-4-Methyl-hexanoic acid 110

A procedure similar to the synthesis of (R)-4-methyl-heptanoic acid 99 was utilized giving the acid as an oil (9.3 g, 56%). MS, m/z (relative intensity): 129 [M−H, 100%].

(4R, 5S)-4-Methyl-3-((R)-4-methyl-hexanoyl)-5-phenyl-oxazolidin-2-one 111

A procedure similar to the synthesis of (4R,5S)-4-methyl-3-((R)-4-methyl-heptanoyl)-5-phenyl-oxazolidin-2-one 100 was utilized giving oxazolidinone 111 as an oil (35.7 g, 95%). MS, m/z (relative intensity): 290 [M+H, 100%].

(3S,5R)-5-Methyl-3-[1-((4R,5S)-4-methyl-2-oxo-5-phenyl-oxazolidin-3-yl)-methanoyl]-heptanoic acid tert-butyl ester 112

A procedure similar to the preparation of (3S,5R)-5-methyl-3-((4R,5S)-4-methyl-2-oxo-5-phenyl-oxazolidine-3-carbonyl)-octanoic acid tert-butyl ester 101 was followed giving 112 as an oil (7.48 g; 31%).

(S)-2-((R)-2-Methyl-butyl)-succinic acid 4-tert-butyl ester 113

To ester 112 (7.26 g, 0.018 mol) in H$_2$O (53 mL) and THF (176 mL) at 0° C. was added a premixed solution of LiOH (37 mL of a 0.8 M solution) and H$_2$O$_2$ (10.57 mL of a 30% solution) and the solution warmed to room temperature. After 2 hours sodium bisulfite (7 g), sodium sulfite (13 g), and water (60 mL) was added and the two layers were separated and the aqueous layer extracted with ether. The combined organic phases were concentrated to an oil that was dissolved in heptane (200 mL). The resultant solid was filtered off and the filtrate dried (MgSO$_4$) and concentrated to afford an oil (4.4 g) that was used without further purification.

(3S,5R)-3-Hydroxymethyl-5-methyl-heptanoic acid tert-butyl ester 114

A procedure similar to the preparation of (3S,5R)-3-hydroxymethyl-5-methyl-octanoic acid tert-butyl ester 103 was utilized giving alcohol 114 as an oil (2.68 g, 69%). MS, m/z (relative intensity): 216 [89%], 174 [M−(CH$_3$)$_3$C, 100%].

(3S,5R)-5-Methyl-3-(toluene-4-sulfonyloxymethyl)-heptanoic acid tert-butyl ester 115

To 114 alcohol (2.53 g, 0.011 mmol) in CH$_2$Cl$_2$ (140 mL) at 0° C. was added pyridine (2.6 g, 0.033 mol), DMAP (100 mg), and tosyl chloride (3.15 g, 0.016 mol) and the solution warmed to room temperature for 3.5 hours whereupon more DMAP and TsCl (3.15 g) were added. After 14 hours 1N HCl was added and the two layers separated. The organic phase was washed with brine then or dried (MgSO$_4$) and concentrated. Flash chromatography (95% to 86% hexane/EtOAc) gave tosylate 115 as an oil (1.53 g, 36%). $^{13}$C NMR (100 MHz; CDCl$_3$) 130.03, 128.12, 72.18, 37.89, 37.71, 32.67, 31.49, 29.88, 28.22, 21.83, 19.07, 11.37.

(3S,5R)-3-Azidomethyl-5-methyl-heptanoic acid tert-butyl ester 116

A procedure similar to the preparation of (3S,5R)-3-azidomethyl-5-methyl-octanoic acid tert-butyl ester 105 was utilized giving an oil 0.956 g, 97%. MS, m/z (relative intensity): 228 [M−N$_2$, 80%].

(S)-4-((R)-2-Methyl-butyl)-pyrrolidin-2-one 118 and (3S, 5R)-3-Aminomethyl-5-methyl-heptanoic acid tert-butyl ester 117

Azide 116 (689 mg) was treated with 20% Pd/C (90 mg) in THF (20 mL) and shaken under an atmosphere of hydrogen for 36 hours. The catalyst was removed by filtration and the resultant oil used without further purification.

Example 10
(3S,5R)-3-Aminomethyl-5-methyl-heptanoic acid

The mixture of amine 117 and lactam 118 was treated with 6N HCl and the solution warmed to 50° C. for 17 hours then cooled to room temperature and concentrated. The resultant oil was subjected to ion-exchange chromatography (Dowex, strongly acidic resin) using 5% ammonium hydroxide to give a cream solid which was recrystallized from methanol/ethyl acetate to give (3S, 5R)-3-aminomethyl-5-methyl-heptanoic acid, example 10. MS, m/z (relative intensity): 174 [M+H, 100%]. Anal. Calcd for $C_{19}H_{19}N_1O_2$. C, 62.39; H, 11.05; N, 8.08. Found: C, 62.23; H, 11.33; N, 7.89.

Example 11
Synthesis of (3S,5S)-3-Aminomethyl-5-methyl-octanoic acid (S)-2,6-Dimethyl-non-2-ene 119

$CuCl_2$ (5.36 g, 39.7 mmol) and LiCl (3.36, 80.0 mmol) were stirred together in dry THF (40 mL) for 15 minutes. The resulting solution was added to methylmagnesium chloride, 3.0 M in THF (168 mL) at 0° C. under nitrogen atmosphere and stirred at that temperature for 15 minutes. To the reaction suspension was added slowly (R)-(−)-Citronellyl bromide (55.16 g, 251.8 mmol) in THF (100 mL), and stirred at 0° C. for 2.5 hours. It was warmed to room temperature and stirring was continued for an additional 1 hour. The mixture was cooled to 0° C. and quenched with saturated ammonium chloride solution. The suspension was then extracted into ether, washed with water, and dried over $MgSO_4$. The solution was concentrated under reduced pressure to afford 36.3 g; 94% of (S)-2,6-Dimethyl-non-2-ene as an oil. MS, m/z (relative intensity): 153 [M−1H, 100%], 194 [M−1H+$CH_3$CN, 45%].

(S)-4-Methyl-heptanoic acid 120

To the (S)-2,6-Dimethyl-non-2-ene 119 (39.0 g, 253.2 mmol) in acetone (1 L) at 0° C. was added Jones reagent (2.7 M, 600 mL) dropwise over 1.5 hours and let stir at room temperature for 18 hours. The reaction mixture was poured into a saturated solution of $Na_2SO_4$ and extracted into ether. It was washed with brine and concentrated in vacuo. The oily residue was dissolved in methanol (70 mL) and 1 M

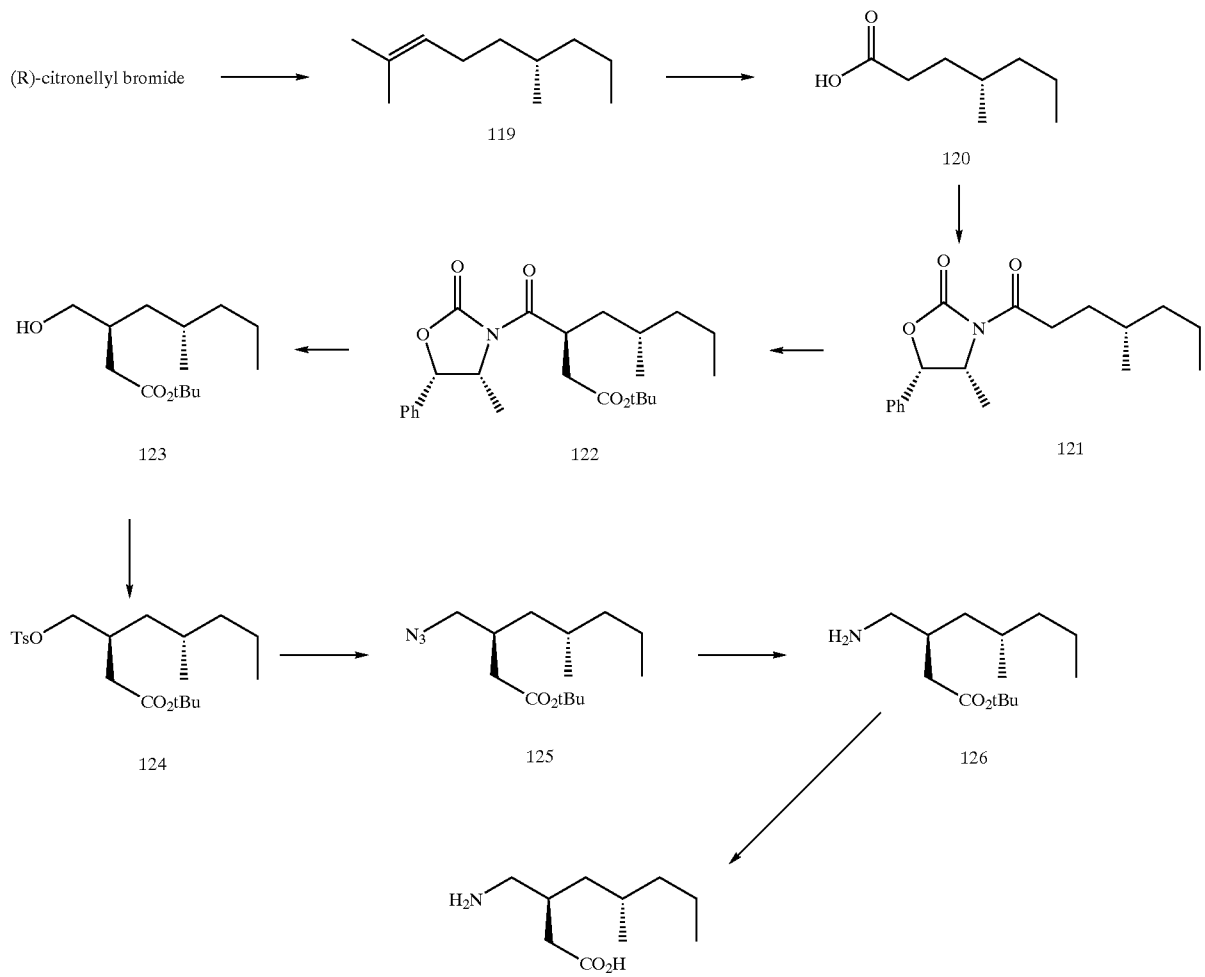

Example 11

NaOH (700 mL) and then stirred for 30 minutes. The aqueous solution was washed with $CH_2Cl_2$, acidified with 10% HCl and extracted into $CH_2Cl_2$. The solution was dried over $MgSO_4$ and concentrated to dryness to give 24.22 g; 66% of (S)-4-Methyl-heptanoic acid as an oil. MS, m/z (relative intensity): 143 [M−1H, 100%].

(4R,5S)-4-Methyl-3-((S)-4-methyl-heptanoyl)-5-phenyl-oxazolidin-2-one 121

A procedure similar to the preparation of (4R,5S)-4-methyl-3-((R)-4-methyl-heptanoyl)-5-phenyl-oxazolidin-2-one 100 was utilized giving (4R,5S)-4-methyl-3-((S)-4-methyl-heptanoyl)-5-phenyl-oxazolidin-2-one 121 6.2 g; 80.0%, as an oil. MS, m/z (relative intensity): 304 [M+1H, 90%], 355 [M+1H+$CH_3CN$, 60%].

(3S,5S)-5-Methyl-3-((4R,5S)-4-methyl-2-oxo-5-phenyl-oxazolidine-3-carbonyl)-octanoic acid tert-butyl ester 122 n-BuLi, 1.6 M in Hexane (18.0 mL, 30.1 mmol) was added dropwise to a solution of diisopropylamine (4.6 mL, 32.6 mmol) in dry THF (50 mL) under nitrogen at −5° C. keeping the temperature below 0° C. during addition. The mixture was let stir at −5° C. for 20 minutes and then cooled to −78° C. 121 (7.6 g, 25.1 mmol) in dry THF (12 mL) was added to the LDA solution and stirred at −78° C. for 30 minutes. t-Butylbromo acetate (4.8 mL, 32.6 mmol) as added to the reaction and stirring at −78° C. was continued for 2 hours. It was let warm to room temperature before stirring for an additional 18 hours. The reaction was quenched with a saturated solution $NaH_2PO_4$, extracted into ethylacetate, and dried over $MgSO_4$. The solution was concentrated to give a solid residue which was dissolved in hot hexane. The hexane solution was allowed to cool to room temperature before cooling further in an ice bath. The resulting precipitate was collected and allowed to air dry to give 122 as a fluffy white solid. 4.3 g; 41%. MS, m/z (relative intensity): 362 [M−C($CH_3$)$_3$+1H, 100%], 418 [M+1H, 20%].

(S)-2-((S)-2-Methyl-pentyl)-succinic acid 4-tert-butyl ester and (3S,5S)-3-Hydroxymethyl-5-methyl-octanoic acid tert-butyl ester 123

To the ester 122 in a mixture of THF (203.0 mL) and water (61.0 mL) at 0° C. was added a premixed solution of 30% $H_2O_2$ (12.2 mL) and LiOH (0.8 M, 42.7 mL). The resulting solution was stirred at 0° C. for 4 hours. To the reaction was added sodium bisulfite (7 g), sodium sulfite (13 g), and water (60 mL). A 1:1 mixture of ether/hexane (200 mL) was then added and the organic phase was separated. The aqueous phase was extracted with ether and the combined organic extract was dried over $MgSO_4$ and concentrated in vacuo. The residue was dissolved in heptane and let stir for 5 minutes. The resulting precipitate was filtered and the filtrate was concentrated to dryness to give as an oil.

(3S,5S)-3-Hydroxymethyl-5-methyl-octanoic acid tert-butyl ester 123

A procedure similar to the preparation of (3S,5R)-3-hydroxymethyl-5-methyl-octanoic acid tert-butyl ester 103 was followed giving 123 as an oil. 4.0 g; 76.0%. MS, m/z (relative intensity): 230 [M−C($CH_3$)$_3$+1H+$CH_3CN$, 100%], 189 [M−C($CH_3$)$_3$+1H, 70%].

(3S,5S)-5-Methyl-3-(toluene-4-sulfonyloxymethyl)-octanoic acid tert-butyl ester 124

A procedure similar to the preparation of (3S,5R)-5-methyl-3-(toluene-4-sulfonyloxymethyl)-octanoic acid tert-butyl ester 104 was followed giving 6.9 g of 124. MS, m/z (relative intensity): 343 [M−C($CH_3$)$_3$+1H, 70%], 384 [M−C($CH_3$)$_3$+1H+$CH_3CN$, 100%].

(3S,5S)-3-Azidomethyl-5-methyl-heptanoic acid tert-butyl ester 125

A procedure similar to the preparation of (3S,5R)-3-azidomethyl-5-methyl-octanoic acid tert-butyl ester 105 was followed giving 2.9 g; 66% of 125 as an oil. MS, m/z (relative intensity): 212 [M−C($CH_3$)$_3$−1H, 45%].

(3S,5S)-3-Aminomethyl-5-methyl-octanoic acid tert-butyl ester 126

A mixture of 125 (2.8 g, 10.4 mmol) and 10% Pd/C (1.0 g) in methanol (50.0 mL) was hydrogenated at 41 PSI for 96 hours. The solution was filtered to give 1.7 g of crude 126 which was used in the next step without further purification. MS, m/z (relative intensity): 244 [M+1H, 100%], 285 [M+1H+$CH_3CN$, 25%].

Example 11

(3S,5S)-3-Aminomethyl-5-methyl-octanoic acid

A procedure similar to the preparation of example 10 (3S,5R)-3-aminomethyl-5-methyl-heptanoic acid was followed giving example 11. 380 mg; 29.0%. $^1$H NMR (CD$_3$OD) δ2.90 (dd, J=3.9, 8.8 Hz, 1H), 2.80 (dd, J=7.6, 5.1 Hz, 1H), 2.40 (dd, J=3.2, 12.51 Hz, 1H), 2.20 (dd, J=8.8, 6.8 Hz, 1H), 2.05 (m, 1H), 1.55 (m, 1H), 1.30 (m, 3H), 1.10 (m, 2H), 0.85 (m, 6H); MS, m/z (relative intensity): 187 [M+1H, 100%], 211 [M+1H+$CH_3CN$, 30%].

Example 12

Synthesis of (3S,5S)-3-Aminomethyl-5-methyl-heptanoic acid

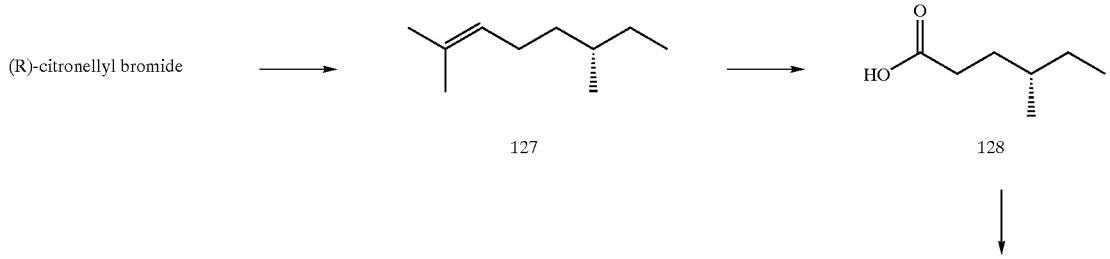

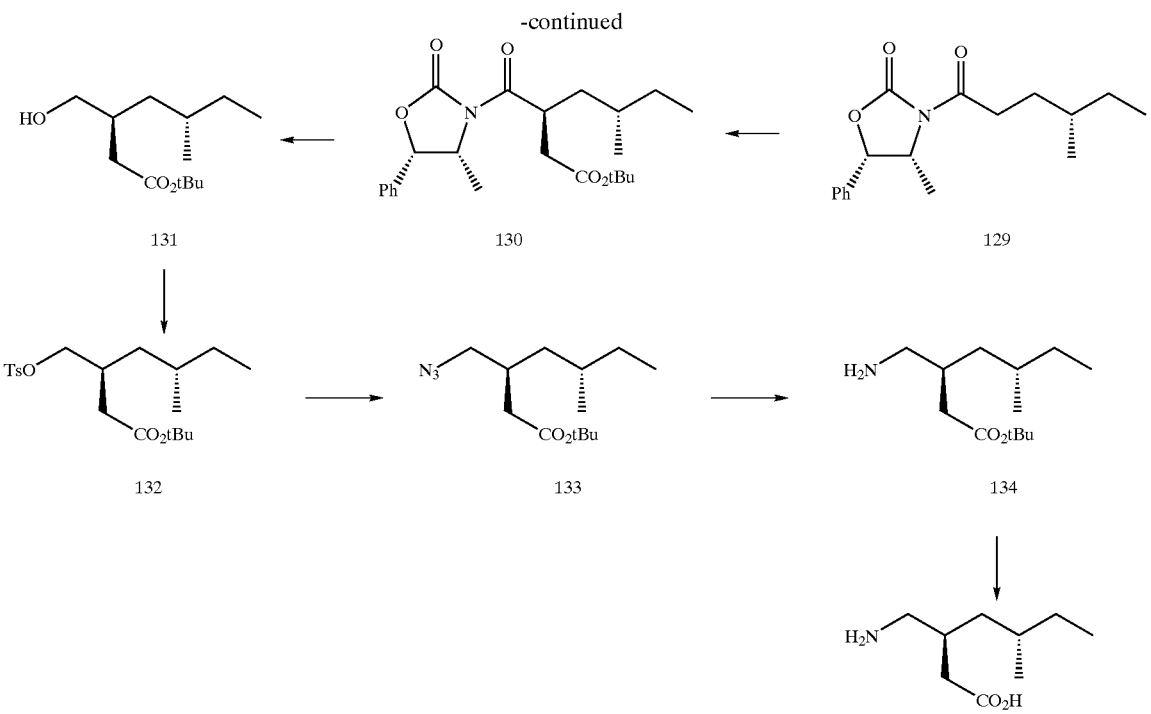

Example 12

(S)-2,6-Dimethyl-oct-2-ene 127

(R)-(−)-Citronellyl bromide (49.1 g, 224.2 mmol) was dropwise added to a solution of LAH 1.0 M in THF (336 mL, 336 mmol) at 0° C. over a 45-minute period. Stirring was continued for an additional 4 hours at 0° C. The reaction was slowly quenched with a saturated solution of ammonium chloride followed by the addition of ether (100 mL). The resulting white slurry was filtered and the filtrate was dried over $MgSO_4$. The solution was concentrated under reduced pressure to afford 26.2 g; 83% of 127 as an oil. MS, m/z (relative intensity): 180 [M−1H+$CH_3$CN, 100%], 139 [M−1H, 90%].

(S)-4-Methyl-hexanoic acid 128

A procedure similar to that used to prepare compound 120 was used giving 15.9 g of 128 as an oil. MS, m/z (relative intensity): 129 [M−1H, 100%], 170 [M−1H+$CH_3$CN, 70%].

(4R,5S)-4-Methyl-3-((S)-4-methyl-hexanoyl)-5-phenyl-oxazolidin-2-one 129

A procedure similar to that used to prepare (4R,5S)-4-Methyl-3-((S)-4-methyl-heptanoyl)-5-phenyl-oxazolidin-2-one 121 was used giving 35.0 g of crude (4R,5S)-4-methyl-3-((S)-4-methyl-hexanoyl)-5-phenyl-oxazolidin-2-one 129 as an oil. It was used in the next step without further purification. MS, m/z (relative intensity): 290 [M+1H, 100%], 331 [M+1H+$CH_3$CN, 20%].

(3S,5S)-5-Methyl-3-((4R,5S)-4-methyl-2-oxo-5-phenyl-oxazolidine-3-carbonyl)-heptanoic acid tert-butyl ester 130

A procedure similar to that used to prepare (3S,5S)-5-methyl-3-((4R,5S)-4-methyl-2-oxo-5-phenyl-oxazolidine-3-carbonyl)-octanoic acid tert-butyl ester 122 was used to give 4.6.0 g, 25.4% of 130 as a white solid. MS, m/z (relative intensity): 348 [M−C($CH_3$)$_3$+1H, 100%], 443 [M−1H+$CH_3$CN, 100%], 402 [M−1H, 55%], 404 [M+1H, 45%].

(3S,5S)-3-Hydroxymethyl-5-methyl-heptanoic acid tert-butyl ester 131

A procedure similar to that used to prepare (3S,5S)-3-Hydroxymethyl-5-methyl-octanoic acid tert-butyl ester 123 was giving 1.2 g, 52.1% of 131 as an oil. MS, m/z (relative intensity): 175 [M−C($CH_3$)$_3$+1H, 100%], 173 [M−C($CH_3$)$_3$−1H, 100%], 216 [M−C($CH_3$)$_3$+1H+$CH_3$CN, 95%].

(3S,5S)-5-Methyl-3-(toluene-4-sulfonyloxymethyl)-heptanoic acid tert-butyl ester 132

A procedure similar to the preparation of (3S,5R)-5-methyl-3-(toluene-4-sulfonyloxymethyl)-octanoic acid tert-butyl ester 104 was followed giving 2.1 g of 132 as an oil. The product was used in the next step without further purification. MS, m/z (relative intensity): 329 [M−C($CH_3$)$_3$+1H, 85%], 370 [M−C($CH_3$)$_3$+1H+$CH_3$CN, 65%].

(3S,5S)-3-Azidomethyl-5-methyl-heptanoic acid tert-butyl ester 133

A procedure similar to the preparation of (3S,5R)-3-azidomethyl-5-methyl-octanoic acid tert-butyl ester 105 was followed giving 0.76 g, 54.0% of 133 as an oil. MS, m/z (relative intensity): 198 [M−C($CH_3$)$_3$−1H, 100%]

(3S,5S)-3-Aminomethyl-5-methyl-heptanoic acid tert-butyl ester 134

A procedure similar to that used for (3S,5S)-3-aminomethyl-5-methyl-octanoic acid tert-butyl ester 126 was used giving 0.62 g of 134 as an oil. The product was used in the next step without further purification. MS, m/z (relative intensity): 230 [M+1H, 100%], 271 [M+1H+$CH_3$CN, 45%].

Example 12

(3S,5S)-3-Aminomethyl-5-methyl-heptanoic acid

A procedure similar to that used for Example 11 was used giving (3S,5S)-3-aminomethyl-5-methyl-heptanoic acid (0.3 g, 65.1%) as a white solid. $^1$H NMR (CD$_3$OD) δ2.80–3.00 (m, 2H), 2.40 (m, 1H), 2.20 (dd, J=8.2, 7.1 Hz, 1H), 2.05 (m, 1H), 1.30–1.50 (m, 3H), 1.00–1.20 (m, 2H), 0.9 (m, 6H); MS, m/z (relative intensity): 187 [M+1H, 100%], 211 [M+1H+$CH_3$CN, 30%]. MS, m/z (relative intensity): 174 [M+1H, 100%], 172 [M−1H, 100%], 215 [M+1H+$CH_3$CN, 20%].

Example 13
Synthesis of (3S,5R)-3-Aminomethyl-5-methyl-nonanoic acid hydrochloride

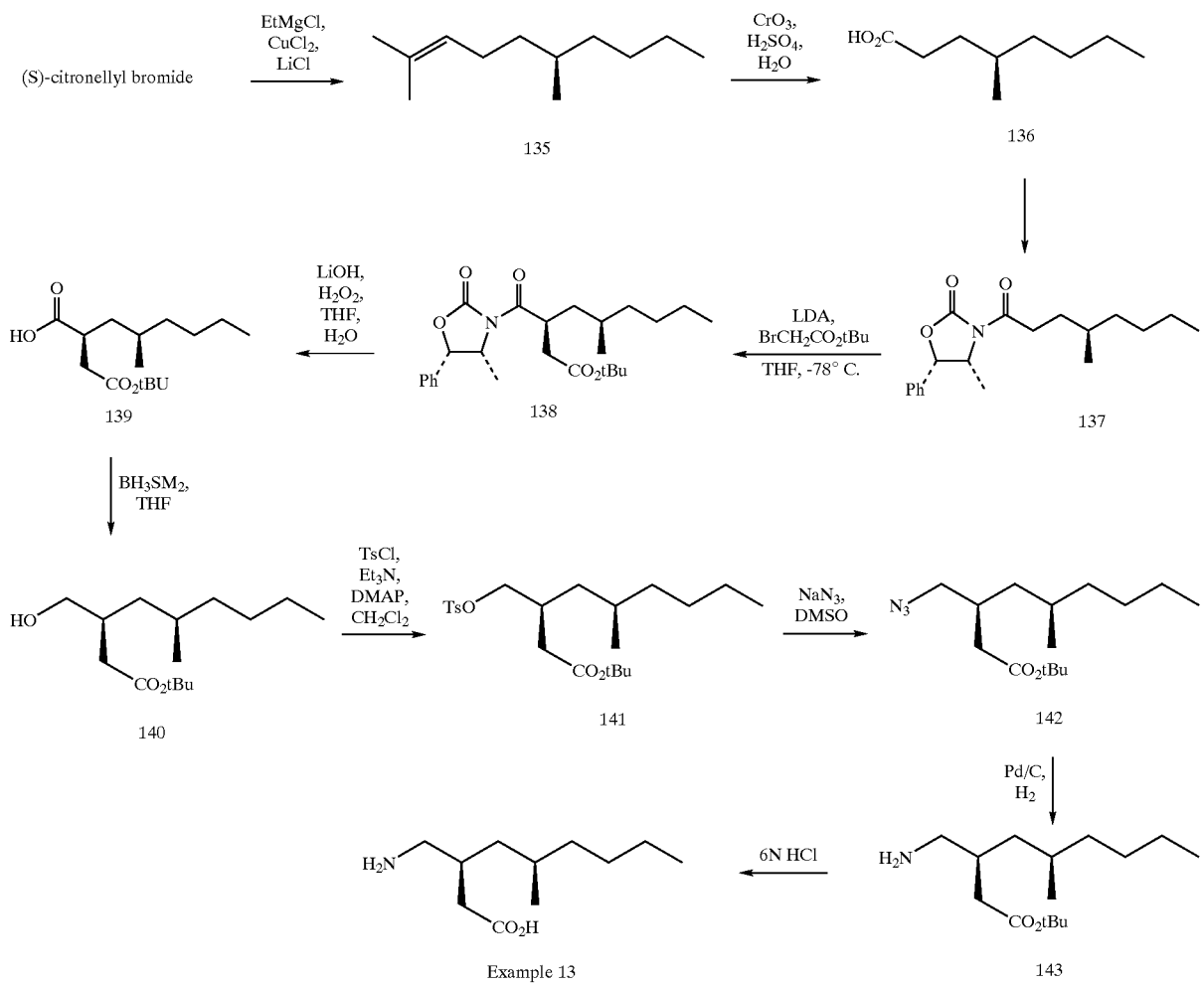

Example 13

(R)-4-Methyl-octanoic acid 136

Lithium chloride (0.39 g, 9.12 mmol) and copper (I) chloride (0.61 g, 4.56 mmol) were combined in 45 ml THF at ambient temperature and stirred 15 minutes, then cooled to 0° C. at which time ethylmagnesium bromide (1 M solution in THF, 45 mL, 45 mmol) was added. (S)-citronellyl bromide (5.0 g, 22.8 mmol) was added dropwise and the solution was allowed to warm slowly to ambient temperature with stirring overnight. The reaction was quenched by cautious addition of sat. $NH_4Cl$ (aq), and stirred with $Et_2O$ and sat. $NH_4Cl$ (aq) for 30 minutes. The phases were separated and the organic phase dried ($MgSO_4$) and concentrated. The crude product was used without purification.

To a solution of alkene 135 (3.8 g, 22.8 mmol) in 50 mL acetone at 0° C. was added Jones' reagent (2.7 M in $H_2SO_4$ (aq), 40 mL, 108 mmol) and the solution was allowed to warm slowly to ambient temperature with stirring overnight. The mixture was partitioned between $Et_2O$ and $H_2O$, the phases were separated, and the organic phase washed with brine, dried ($MgSO_4$), and concentrated. The residue was purified by flash chromatography (8:1 hexanes:EtOAc) to afford 2.14 g (59%) of acid 136 as a colorless oil: LRMS: m/z 156.9 (M+); $^1$H NMR ($CDCl_3$): δ2.33 (m, 2H), 1.66 (m, 1H), 1.43 (m, 2H), 1.23 (m, 5H), 1.10 (m, 1H), 0.86 (m, 6H).

Jones' reagent was prepared as a 2.7M solution by combining 26.7 g $CrO_3$, 23 mL $H_2SO_4$, and diluting to 100 mL with $H_2O$.

(4R, 5S)-4-Methyl-3-((R)-4-methyl-octanoyl)-5-phenyl-oxazolidin-2-one 137

To acid 136 (2.14 g, 13.5 mmol) in 25 mL $CH_2Cl_2$ at 0° C. was added 3 drops DMF, followed by oxalyl chloride (1.42 mL, 16.2 mmol) resulting in vigorous gas evolution. The solution was warmed directly to ambient temperature, stirred 30 minutes, and concentrated. Meanwhile, to a solution of the oxazolidinone (2.64 g, 14.9 mmol) in 40 mL THF at −78° C. was added n-butyllithium (1.6 M soln in hexanes, 9.3 mL, 14.9 mmol) dropwise. The mixture was stirred for 10 minutes at which time the acid chloride in 10 mL THF was added dropwise. The reaction was stirred 30 minutes at −78° C., then warmed directly to ambient temperature and quenched with sat. $NH_4Cl$. The mixture was partitioned between $Et_2O$ and sat. $NH_4Cl$ (aq), the phases were separated, and the organic phase dried ($MgSO_4$), and concentrated to furnish 3.2 g of oxazolidinone 137 as a colorless oil. LRMS: m/z 318.2 (M+); $^1$H NMR ($CDCl_3$): δ7.34 (m, 5H), 5.64 (d, J=7.3 Hz, 1H), 4.73 (quint, J=6.8 Hz, 1H), 2.96 (m, 1H), 2.86 (m, 1), 1.66 (m, 1H), 1.47 (m, 2H), 1.26 (m, 5H), 1.13 (m, 1H), 0.88 (m, 9H). The crude product was used without purification.

(3S,5R)-5-Methyl-3-((4R,5S)-4-methyl-2-oxo-5-phenyl-oxazolidine-3-carbonyl)-nonanoic acid tert-butyl ester 138

To a solution of diisopropylamine (1.8 mL, 12.6 mmol) in 30 mL THF at −78° C. was added n-butyllithium (1.6 M soln in hexanes, 7.6 mL, 12.1 mmol), and the mixture stirred 10 minutes at which time oxazolidinone 137 (3.2 g, 10.1 mmol) in 10 mL THF was added dropwise. The solution was stirred for 30 minutes, t-butyl bromoacetate (1.8 mL, 12.1 mmol) was added quickly dropwise at −50° C., and the mixture was allowed to warm slowly to 10° C. over 3 hours. The mixture was partitioned between $Et_2O$ and sat. $NH_4Cl$ (aq), the phases were separated, and the organic phase dried ($MgSO_4$), and concentrated. The residue was purified by flash chromatography (16:1 to 8:1 hexanes:EtOAc) to provide 2.65 g (61%) of ester 138 as a colorless crystalline solid, mp=84–86° C. $[\alpha]_D^{23}$+17.1 (c=1.00, $CHCl_3$); $^1H$ NMR ($CDCl_3$): δ7.34 (m, 5H), 5.62 (d, J=7.3 Hz, 1H), 4.73 (quint, J=6.8 Hz, 1H), 4.29 (m, 1H), 2.67 (dd, J=9.8, 16.4 Hz, 1H), 2.40 (dd, J=5.1, 16.4 Hz, 1H), 1.69 (m, 1H), 1.38 (s, 9H), 1.28 (m, 7H), 1.08 (m, 1H), 0.88 (m, 9H); $^{13}C$ NMR ($CDCl_3$) δ176.45, 171.22, 152.71, 133.64, 128.86, 125.86, 80.83, 78.87, 55.33, 40.02, 38.21, 37.59, 36.31, 30.86, 29.29, 28.22, 23.14, 20.41, 14.36, 14.26. Anal. Calcd for $C_{25}H_{37}NO_5$: C, 69.58; H, 8.64; N, 3.25. Found: C, 69.37; H, 8.68; N, 3.05.

(S)-2-((R)-2-Methyl-hexyl)-succinic acid 4-tert-butyl ester 139

To a solution of ester 138 (2.65 g, 6.14 mmol) in 20 mL THF at 0° C. was added a precooled (0° C.) solution of LiOH monohydrate (1.0 g, 23.8 mmol) and hydrogen peroxide (30 wt % aqueous soln, 5.0 mL) in 10 mL $H_2O$. The mixture was stirred vigorously for 90 minutes, then warmed to ambient temperature and stirred 90 minutes. The reaction was quenched at 0° C. by addition of 100 mL 10% $NaHSO_3$ (aq), then extracted with $Et_2O$. The phases were separated, and the organic phase washed with brine, dried ($MgSO_4$), and concentrated. The crude acid 139 was used without purification.

(3S,5R)-3-Hydroxymethyl-5-methyl-nonanoic acid tert-butyl ester 140

To a solution of the crude acid 139 (6.14 mmol) in 30 mL THF at 0° C. was added borane-dimethyl sulfide complex (2.0 M soln in THF, 4.6 mL, 9.2 mmol), and the mixture was allowed to warm slowly to ambient temperature overnight. Additional $BH_3$-DMS was added until the acid was completely consumed (ca. 5 mL). The reaction was quenched by addition of MeOH, then partitioned between $Et_2O$ and sat. $NaHCO_3$ (aq). The phases were separated, and the organic phase washed with brine, dried ($MgSO_4$), and concentrated to provide alcohol 140. LRMS: m/z 226.1; $^1H$ NMR ($CDCl_3$): δ3.63 (dd, J=11.0, 4.2 Hz, 1H), 3.42 (dd, J=11.0, 6.8 Hz, 1H), 2.30 (dd, J=14.9, 7.6 Hz, 1H), 2.20 (dd, J=14.9, 5.6 Hz, 1H), 2.03 (m, 2H), 1.42 (s, 9H), 1.24 (m, 6H), 1.02 (m, 2H), 0.85 (m, 6H). The crude product was used without purification.

(3S,5R)-5-Methyl-3-(toluene-4-sulfonyloxymethyl)-nonanoic acid tert-butyl ester 141

To alcohol 140 (6.14 mmol) in 30 mL $CH_2Cl_2$ at 0° C. was added DMAP (0.1 g), p-toluenesulfonyl chloride (1.37 g, 7.2 mmol), and then triethylamine (1.8 mL, 13 mmol) was added quickly dropwise. The mixture was warmed immediately to ambient temperature following addition and stirred overnight, and did not proceed to completion. The mixture was partitioned between $Et_2O$ and 1N HCl (aq), the phases were separated, and the organic phase washed with sat. $NaHCO_3$ (aq), dried ($MgSO_4$), and concentrated to provide tosylate 141. The product was used without further purification.

(3S,5R)-3-Azidomethyl-5-methyl-nonanoic acid tert-butyl ester 142

A procedure similar to the preparation of (3S,5R)-3-azidomethyl-5-methyl-octanoic acid tert-butyl ester 105 was followed giving azide 142 as a colorless oil. LRMS: m/z 200.1; $^1H$ NMR ($CDCl_3$): δ3.31 (dd, J=12.2, 4.2 Hz, 1H), 3.19 (dd, J=12.2, 5.9 Hz, 1H), 2.22 (m, 1H), 2.10 (m, 1H), 1.39 (s, 9H), 1.21 (m, 8H), 1.00 (m, 2H), 0.81 (m, 6H).

Example 13

(3S,5R)-3-Aminomethyl-5-methyl-nonanoic acid hydrochloride

The azide 142 (1.0 g) was hydrogenated in the presence of 20% Pd/C, EtOH, at 45 psi of $H_2$ for 15 hours to provide the crude amino ester 143 which was concentrated and used without purification. To the amino ester 143 was added 6 mL 6N HCl (aq) and the mixture was heated to reflux 90 minutes, cooled, and concentrated. Recrystallization from EtOAc:hexanes provided 0.38 g (45% from azide) of (3S,5R)-3-aminomethyl-5-methyl-nonanoic acid hydrochloride as a colorless crystalline solid (HCl salt), and a second crop of 82 mg (10% from azide) was also obtained. mp=146–156° C. LRMS: m/z 200.1 (M+); $^1H$ NMR ($CDCl_3$): δ2.87 (dd, J=13.2, 5.4 Hz, 1H), 2.79 (dd, J=13.2, 7.3 Hz, 1H), 2.29 (d, J=6.8 Hz, 2H), 2.08 (m, 1H), 1.31 (m, 1H), 1.09 (m, 7H0, 0.92 (m, 1H), 0.68 (m, 6H). Anal. Calcd for $C_{11}H_{24}NO_2Cl$: C, 55.57; H, 10.17; N, 5.89. Found: C, 55.69; H, 10.10; N, 5.86.

Example 14

Synthesis of (3S,5S)-3-Aminomethyl-5-methyl-nonanoic acid

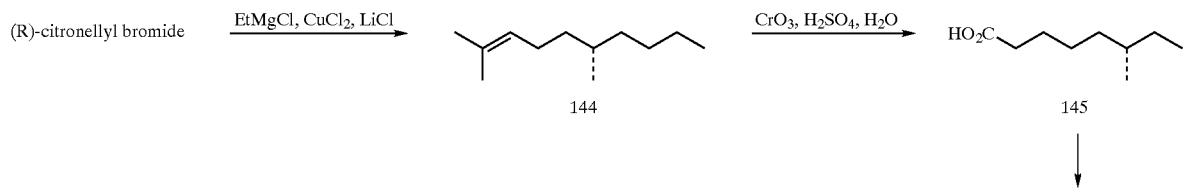

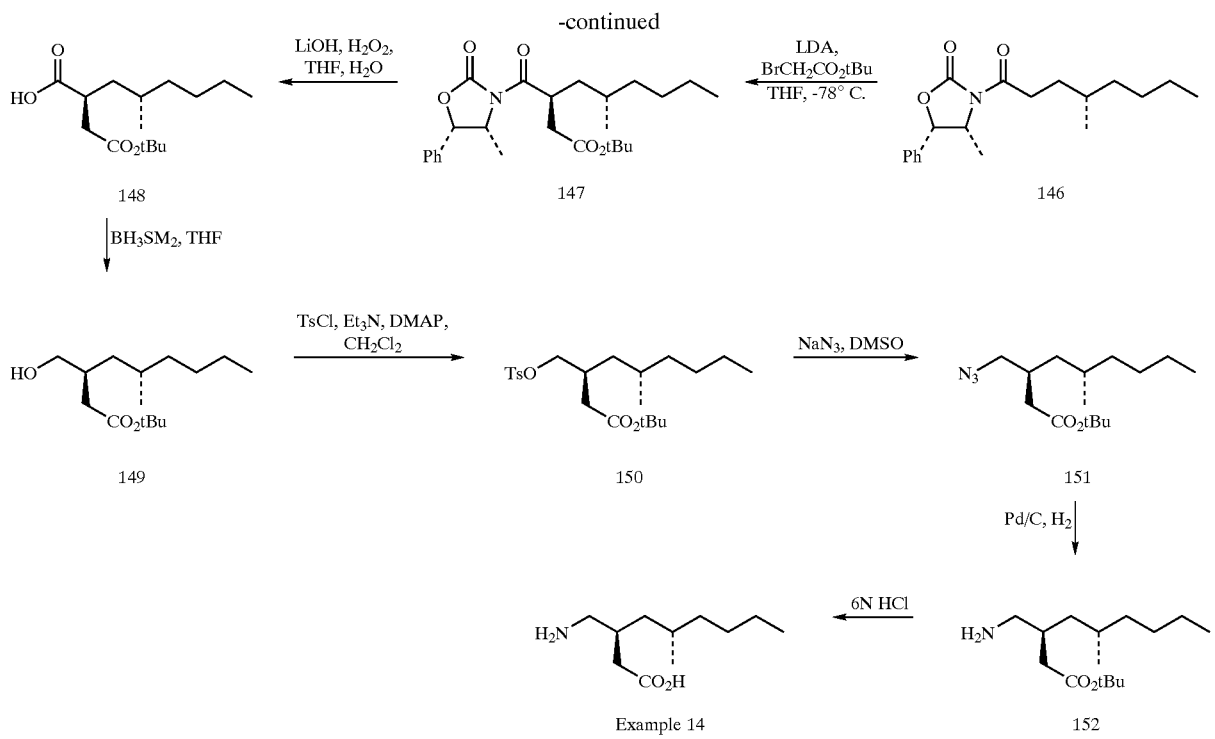

The (S)-acid 145 was prepared from (R)-citronellyl bromide according to the procedure outlined above for (R)-4-methyl-octanoic acid 136. The yield was comparable and the $^1$H NMR spectrum was identical to that of the (R)-acid enantiomer. LRMS: m/z 158.9 (M+1).

Oxazolidinone 146 was prepared from acid 145 as described above for (4R,5S)-4-methyl-3-((R)-4-methyl-octanoyl)-5-phenyl-oxazolidin-2-one 137. LRMS: m/z 290.1 (M−27); $^1$H NMR (CDCl$_3$): δ7.38 (m, 3H), 7.28 (m, 2H), 5.64 (d, J=7.1 Hz, 1H), 4.74 (quint, J=6.8 Hz, 1H), 2.92 (m, 2H), 1.71 (m, 1H), 1.42 (m, 7H), 1.18 (m, 1H), 0.88 (m, 9H).

t-Butyl ester 147 was prepared from oxazolidinone 146 as described above for compound 138. LRMS: m/z 348.1 (M−83).

Alcohol 149 was prepared from the t-butyl ester 147 as described above for (3S,5R)-3-hydroxymethyl-5-methyl-nonanoic acid tert-butyl ester 140. LRMS: m/z 156.9 (M−100); $^1$H NMR (CDCl$_3$): δ3.60 (dd, J=11.0, 4.6 Hz, 1H), 3.45 (dd, J=11.0, 6.8 Hz, 1H), 2.24 (m, 2H), 2.04 (m, 2H), 1.42 (s, 9H), 1.17–1.38 (m, 7H), 1.11 (m, 1H), 0.84 (m, 6H).

Example 14
(3S,5S)-3-Aminomethyl-5-methyl-nonanoic acid (3S,5S)-3-Aminomethyl-5-methyl-nonanoic acid was obtained from 149 as described above for (3S,5R)-3-aminomethyl-5-methyl-nonanoic acid hydrochloride. The crude HCl salt thus obtained was purified by ion exchange chromatography on Dowex 50WX8 50–100 mesh, H-Form resin, using 10% NH$_4$OH as eluant to provide the free base. The waxy solid was washed twice with Et$_2$O and dried to furnish an amorphous white solid, mp 144–146° C. LRMS: m/z 172.0 (M−28); $^1$H NMR (CDCl$_3$): δ2.76 (d, J=5.9 Hz, 2H), 2.14 (m, 1H), 1.96 (m, 2H), 1.25 (m, 1H), 1.12 (m, 6H), 0.96 (m, 2H), 0.66 (m, 6H).

Example 15
Synthesis of (3S,5R)-3-Aminomethyl-5-methyl-decanoic acid

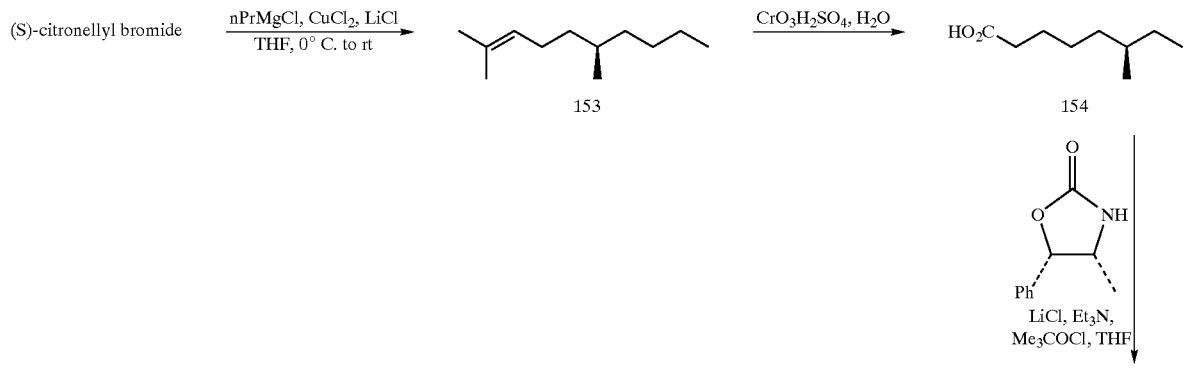

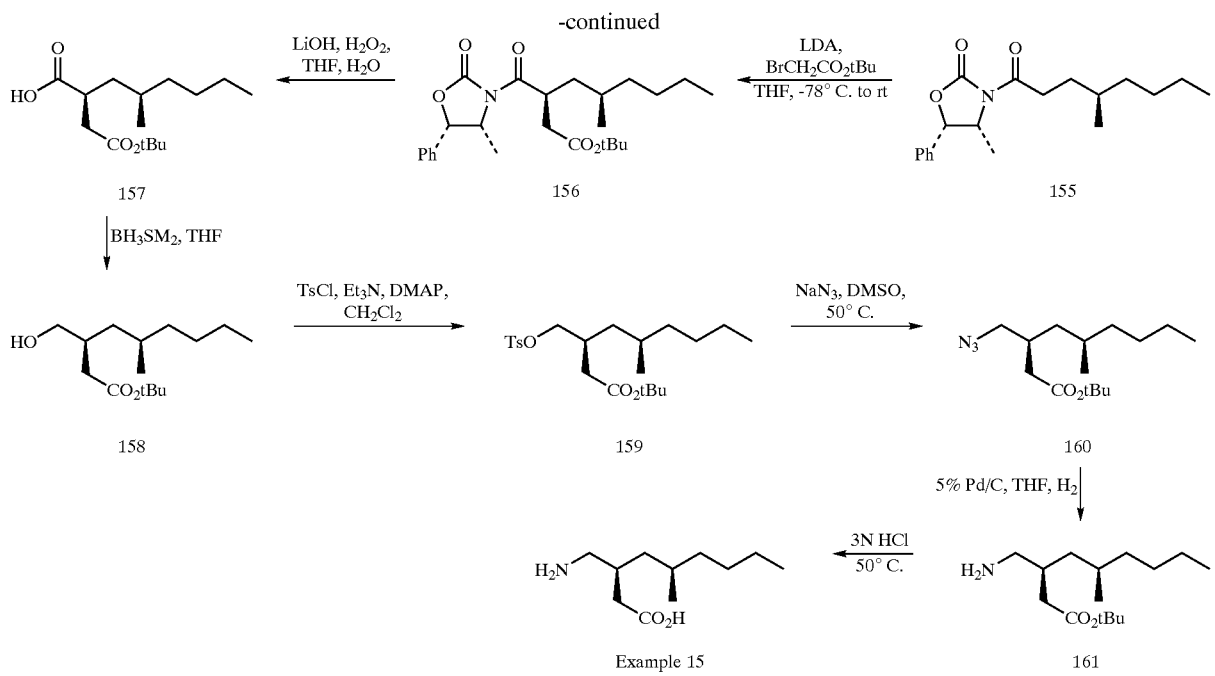

Example 15

(R)-2,6-Dimethylundec-2-ene 153

A procedure similar to the preparation of (S)-2,6-dimethyl-non-2-ene 119 was used giving 153 as a colorless oil (20.16 g, 98%). $^1$H NMR (400 MHz, CDCl$_3$) δ5.10–5.06 (m, 1H), 2.10–1.89 (m, 2H), 1.66 (s, 3H), 1.58 (s, 3H), 1.34–1.23 (m, 4H), 1.15–1.06 (m, 2H), 0.88–0.81 (m, 11H).

(R)-4-methylnonanoic acid 154

(R)-2,6-Dimethylundec-2-ene 153 (10.03 g, 55.03 mmol) was dissolved in acetone (270 mL) and cooled to 0° C. Jones reagent (CrO$_3$/H$_2$SO$_4$) (2.7 M, 120 mL) was added dropwise, and the reaction allowed to warm to room temperature over 18 hours. The reaction was poured on to water/Na$_2$SO$_4$ (200 mL), and the aqueous layer extracted with ethyl acetate (4×100 mL). The combined organics were dried over MgSO$_4$, filtered and rotovapped to give an oil. The crude oil was dissolved in CH$_2$Cl$_2$ (400 mL) and cooled to −78° C. Ozone was bubbled into reaction until blue to remove traces of the impurity (6E)(3S)-3,7-dimethylocta-1,6-diene. Dimethylsulfide (5 mL) was added, and the reaction stirred at room temperature for 2 hours. The solvent was removed, and the crude material chromatographed on silica eluting with 20% EtOAc/hex to give oil. The oil was dissolved in ether (100 mL) and extracted with 10% NaOH (2×25 mL). The aqueous layers were combined and extracted with ether (50 mL). The aqueous layer was cooled to 0° C. and acidified with HCl. The acidic layer was extracted with EtOAc (3×100 mL), and the combined extracts dried over MgSO$_4$, filtered and rotovapped to give 154 as an oil (6.86 g, 54%). $^1$H NMR (400 MHz, CDCl$_3$) δ2.40–2.25 (m, 4H), 1.70–1.62 (m, 2H), 1.47–1.11 (m, 8H), 0.87–0.84 (m, 6H); [α]$_D$=−11.4 (cl in CHCl$_3$).

(4R,5S)-4-Methyl-3-((R)-4-methyl-nonanoyl)-5-phenyl-oxazolidin-2-one 155

Compound 154 (6.504 g, 37.76 mmol) was dissolved in THF (95 mL) and cooled to 0° C. Triethylamine (19.74 mL, 141.6 mmol) was added dropwise, followed by dropwise addition of trimethylacetyl chloride (6.98 mL, 56.64 mmol). The thick white suspension was stirred at 0° C. for 90 minutes. LiCl (1.86 g, 41.54 mmol), (4R)-4-methyl-5-phenyl-1,3-oxazolidin-2-one (6.824 g, 38.51 mmol), and THF (70 mL) were added, and the reaction warmed to room temperature overnight. The solvent was evaporated. The solids were taken up in EtOAc, filtered off, and washed generously with EtOAc. The filtrate was washed with water (2×50 mL), and brine. The organics were dried over MgSO$_4$, filtered, and rotovapped. The crude material was chromatographed on silica eluting with 10% EtOAc/hexanes to give 155 as an oil (10.974 g, 88%). $^1$H NMR (400 MHz, CDCl$_3$) δ7.44–7.35 (m, 3H), 7.31–7.26 (m, 2H), 5.66 (d, J=7.33 Hz, 1H), 4.76 (quin, J=7.03 Hz, 1H), 3.04–2.96 (m, 1H), 2.93–2.86 (m, 1H), 1.74–1.66 (m, 1H), 1.52–1.47 (m, 1H), 1.46–1.36 (m, 2H), 1.27–1.16 (m, 2H), 0.92–0.87 (m, 8H); [α]$_D$=+34.1 (cl in CHCl$_3$).

(3S,5R)-5-Methyl-3-((4R,5S)-4-methyl-2-oxo-5-phenyl-oxazolidine-3-carbonyl)-decanoic acid tert-butyl ester 156

A procedure similar to the preparation of (3S,5S)-5-methyl-3-((4R,5S)-4-methyl-2-oxo-5-phenyl-oxazolidine-3-carbonyl)-octanoic acid tert-butyl ester 122 was followed giving (3S,5R)-5-methyl-3-((4R,5S)-4-methyl-2-oxo-5-phenyl-oxazolidine-3-carbonyl)-decanoic acid tert-butyl ester 156 as an oil (0.668 g, 90%). $^1$H NMR (400 MHz, CDCl$_3$) δ7.41–7.28 (m, 5H), 5.63 (d, J=7.33 Hz, 1H), 4.74 (quin, J=6.84 Hz, 1H), 4.33–4.26 (m, 1H), 2.68 (dd, J=16.4, 9.77 Hz, 1H), 2.41 (dd, J=16.6, 4.88 Hz, 1H), 1.68 (quin, J=6.6 Hz, 1H), 1.50–1.32 (m, 10H), 1.28–1.21 (m, 1H), 1.15–1.08 (m, 1H), 0.90–0.86 (m, 9H); MS (APCI) m/z 348 (M$^+$−97, 100%); [α]$_D$=+18.8 (cl in CHCl$_3$).

(S)-2-((R)-2-Methyl-heptyl)-succinic acid 4-tert-butyl ester 157

Compound 156 (5.608 b, 12.59 mmol) was dissolved in THF/H$_2$O (60 mL/14 mL) and cooled to 0° C. LiOH (1N, 18.89 mL) and H$_2$O$_2$ (35%, 4.45 mL, 50.4 mmol) were combined, and then added to the reaction dropwise keeping T<5° C. the reaction was stirred at 0° C. for 4 hours, and quenched with Na$_2$SO$_3$ (6.3 g) and NaHSO$_3$ (3.4 g) in 50 mL H$_2$O added dropwise. The reaction was stirred for 15 minutes, and the layers separated. The aqueous layer was extracted with EtOAc (3×100 mL), and the combined extracts dried over MgSO$_4$, filtered, and rotovapped to give an oil. The crude material was dissolved in EtOAc (10 mL)

and added dropwise to heptane (250 mL). The suspension was stirred for 20 minutes, and the solids filtered and washed with heptane. The filtrate was washed with 60° C. $H_2O$ (100 mL), dried over $MgSO_4$, filtered, and rotovapped to give 157 as an oil (3.52 g). the material was used directly in the next step.

(3S,5R)-3-Hydroxymethyl-5-methyl-decanoic acid tert-butyl ester 158

Compound 157 (3.52 g, 12.3 mmol) was dissolved in anhydrous THF (123 mL) and cooled to 0° C. Borane dimethylsulfide complex (10 M, 3.69 mL) was added dropwise, and the reaction then warmed to room temperature and stirred for 1 hour. the reaction was cooled to 0° C., and quenched with MeOH (20 mL) added dropwise. The reaction was stirred for 18 hours, and the solvent rotovapped off. The crude material was chromatographed on silica eluting with 20% EtOAc/hexanes to give 158 (2.28 g, 68%) as an oil. $^1$H NMR (400 MHz, $CDCl_3$) δ3.65–3.59 (m, 1H), 3.43 (dd, J=11.1, 6.96 Hz, 1H), 2.31 (dd, J=14.9, 7.57 Hz, 1H), 2.21 (dd, J=15.1, 5.62 Hz, 1 H), 2.06–2.02 (m, 1H), 1.43 (s, 9H), 1.40–1.25 (m, 4H), 1.07–1.13 (m, 1H), 1.03–0.96 (m, 1H), 0.86–0.84 (m, 6H); MS (APCI) m/z 216 ($M^+$–56, 100%).

(3S,5R)-5-Methyl-3-(toluene-4-sulfonyloxymethyl)-decanoic acid tert-butyl ester 159

Compound 158 (2.27 g, 8.33 mmol) was dissolved in $CH_2Cl_2$ (30 mL) and cooled to 0° C. Tosyl chloride (1.91 g, 10.0 mmol) and catalytic DMAP were added, followed by dropwise addition of triethylamine (2.55 mL, 18.33 mmol). The reaction was then stirred at 0° C. for 18 hours. The solvent was rotovapped off (removed under reduced pressure), and the crude material washed with EtOAc and filtered. The solids were washed with EtOAc, and the filtrate washed with 0.5N HCl (20 mL), brine (30 mL), dried over $MgSO_4$, filtered and rotovapped. The oil was chromatographed on silica eluting with a 5% EtOAc/hexanes gradient to 10% EtOAc/hexanes to give 159 (3.399 g, 96%) as an oil. $^1$H NMR (400 MHz, $CDCl_3$) δ7.75 (d, J=8.30 Hz, 2H), 7.31 (d, J=8.30 Hz, 2H), 3.99 (dd, J=9.65, 3.54 Hz, 1H), 3.89 (dd, J=9.52, 5.37 Hz, 1H), 2.42 (s, 3H), 2.28 (dd, J=14.7, 6.23 Hz, 1H), 2.19–2.14 (m, 1H), 2.10 (dd, J=14.9, 6.35 Hz, 1H), 1.38 (s, 9H), 1.31–1.17 (m, 3H), 1.08–0.81 (m, 2H), 0.79–0.76 (m, 6H); $[α]_D$=–10.1 (cl in $CHCl_3$).

(3S,5R)-3-Azidomethyl-5-methyl-decanoic acid tert-butyl ester 160

Compound 159 (3.01 g, 7.05 mmol), sodium azide (1.26 g, 19.40 mmol) and DMSO (12 mL) were combined and heated to 60° C. for 3 hours. EtOAc (100 mL) was added to the reaction and filtered. The solids were washed with EtOAc (20 mL), and the filtrated evaporated. The crude material was chromatographed on silica eluting with 5% EtOAc/hexanes to give 160 as an oil (1.86 g, 89%).

(3S,5R)-3-Aminomethyl-5-methyl-decanoic acid tert-butyl ester 161

A solution of compound 160 (1.86 g, 6.25 mmol) in THF (50 mL) was shaken over 5% Pd/C under hydrogen and pressure for 8 hours with three purges of hydrogen. The catalyst was filtered off and the filtrate evaportated. The crude material was chromatographed on silica eluting with methanol to give 161 as an oil (1.21 g, 71%). $^1$H NMR (400 MHz, $CDCl_3$) δ2.70 (dd, J=12.9, 4.40 Hz, 1H), 2.54 (dd, J=12.7, 6.59 Hz, 1H), 2.26 (dd, J=14.5, 6.96, 1H), 2.12 (dd, J=14.5, 6.47 Hz, 1H), 1.91 (m, 1H), 1.91 (m, 1H), 1.43 (s, 12H), 1.39–1.25 (m, 4H), 1.14–1.07 (m, 1H), 1.03–0.97 (m, 1H), 0.86–0.82 (m, 6H).

Example 15

(3S,5R)-3-Aminomethyl-5-methyl-decanoic acid

Compound 161 (1.20 g, 4.44 mmol) was heated to 50° C. in 3N HCl (30 mL) for 4 hours. The solvent was evaporated, and the oil washed with toluene, and evaporated. The crude material was passed through an ion exchange column (Dowex 50WX8-100, strongly acidic) eluting with water, then 0.5N $NH_4OH$. Isolate (3S,5R)-3-aminomethyl-5-methyl-decanoic acid as a white solid (0.725 g, 75%): mp=174–175° C.; $^1$H NMR (400 MHz, $CDCl_3$) δ2.83 (dd, J=12.69, 4.88 Hz, 1H), 2.70 (dd, J=13.1, 7.45 Hz, 1H), 2.08 (d, J=6.59 Hz, 2H), 1.98 (m, 1H), 1.28–1.20 (m, 1H), 1.19–1.09 (m, 2H), 0.99–0.91 (m, 2H), 0.66 (m, 6H); MS (APCI) m/z 215 ($M^+$, 10%), 174 ($M^+$–41, 100%); $[α]_D$=–5.7 (cl.025 in $H_2O$).

Example 16

Synthesis of (3S,5S)-3-Aminomethyl-5-methyl-decanoic acid

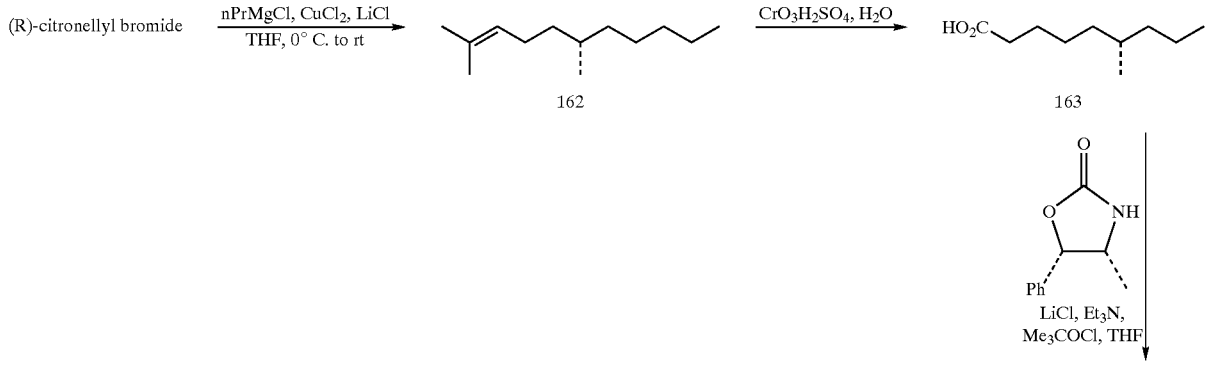

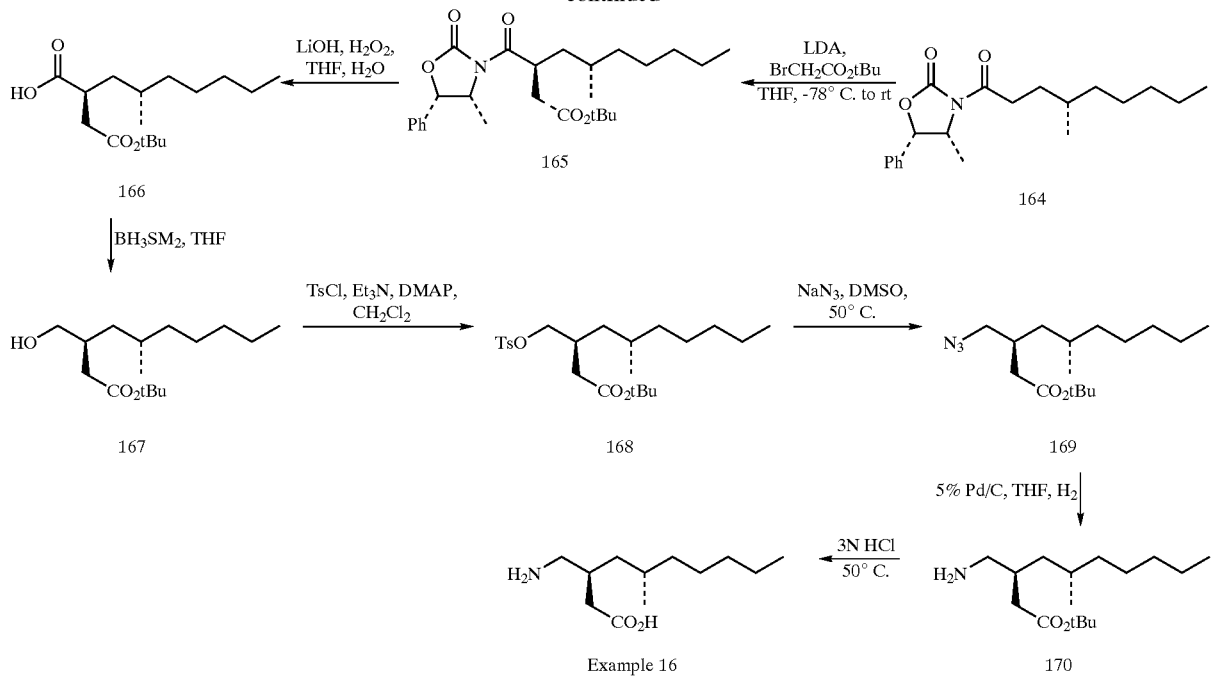

(S)-2,6-Dimethyl-undec-2-ene 162 nPropylmagnesium chloride/ether solution (2.0 M, 228 mL) was cooled to −20° C. under a $N_2$ atmosphere. LiCl (3.87 g, 91.25 mmol), $CuCl_2$ (6.13 g, 45.63 mmol), and distilled THF (456 mL) were combined and stirred for 30 minutes. The $Li_2CuCl_4$ solution was added via cannula to the Grignard reagent, and the resulting solution stirred for 30 minutes at −20° C. R-(−)-Citronellyl bromide (50 g, 228.1 mmol) was dissolved in THF (60 mL) and added dropwise to the Grignard solution. The reaction was stirred at 0° C. for 1 hour. The reaction was cooled to −40° C. and quenched with $NH_4Cl$ (sat'd, 200 mL) added dropwise. The layers were separated and the aqueous layer extracted with ether (3×100 mL). The combined organics were dried over $MgSO_4$, filtered, and rotovapped to give an oil. The crude material was chromatographed on silica eluting with hexanes to give 162 as a colorless oil (9.15 g, 22%). $^1$H NMR (400 MHz, $CDCl_3$) δ5.10–5.06 (m, 1H), 2.10–1.89 (m, 2H), 1.66 (s, 3H), 1.58 (s, 3H), 1.34–1.23 (m, 4H), 1.15–1.06 (m, 2H), 0.88–0.81 (m, 11H).

(S)-4-Methylnonanoic acid 163

Compound 162 (7.97 g, 43.7 mmol) was dissolved in acetone (214 mL) and cooled to 0° C. Jones reagent ($CrO_3$/$H_2SO_4$) (2.7 M, 95 mL) was added dropwise, and the reaction allowed to warm to room temperature over 18 hours. The reaction was poured on to water/$Na_2SO_4$ (200 mL), and the aqueous layer extracted with ethyl acetate (4×100 mL). The combined organics were dried over $MgSO_4$, filtered, and rotovapped to give an oil. The crude oil was chromatographed on silica eluting with hexanes to give 163 as an oil (5.56 g, 74%). $^1$H NMR (400 MHz, $CDCl_3$) δ2.40–2.25 (m, 4H), 1.70–1.62 (m, 2H), 1.47–1.11 (m, 8H), 0.87–0.84 (m, 6H); MS APCI m/z 170.9 (M−1, 100%).

(4R,5S)-4-Methyl-3-((S)-4-methyl-nonanoyl)-5-phenyl-oxazolidin-2-one 164

A procedure similar to that used to prepare compound 155 was used except that (S)-4-methylnonanoic acid 163 (5.56 g, 32.27 mmol) was used as a reactant to give 164 as an oil (10.70 g 100%). $^1$H NMR (400 MHz, $CDCl_3$) δ7.42–7.34 (m, 3H), 7.28 (d, J=6.59 Hz, 2H), 5.64 (d, J=7.33 Hz, 1H), 4.74 (quin, J=6.78 Hz, 1H), 2.94–2.85 (m, 2H), 1.73–1.67 (m, 1H), 1.47–1.43 (m, 1H), 1.39–1.22 (m, 7H), 0.90–0.84 (m, 8H).

(3S,5S)-5-Methyl-3-((4R,5S)-4-methyl-2-oxo-5-phenyl-oxazolidine-3-carbonyl)-decanoic acid tert-butyl ester 165

A procedure similar to that used to prepare compound 156 was used to give 165 as a solid (4.25 g, 61%). MS (APCI) m/z 446 ($M^+$+1, 10%), 390 ($M^+$−55, 100%, −tBu).

(S)-2-((S)-2-Methyl-heptyl)-succinic acid 4-tert-butyl ester 166

A procedure similar to that used for compound 157 was used except that ester 165 (8.42 g, 18.89 mmol) was used as a reactant to give 166 as an oil (5.81 g). The material was used directly in the next step. MS (APCI) m/z 285 (M−1, 100%).

(3S,5S)-3-Hydroxymethyl-5-methyl-decanoic acid tert-butyl ester 167

A procedure similar to that used to prepare compound 158 was used except that (S)-2-((S)-2-methyl-heptyl)-succinic acid 4-tert-butyl ester 166 (5.78 g, 20.18 mmol) was used as a reactant to give 167 as an oil (4.18 g, 76%). $^1$H NMR (400 MHz, $CDCl_3$) δ3.64–3.58 (m, 1H), 3.84–3.42 (m, 1H), 2.28–2.20 (m, 1H), 2.09–2.02 (m, 1H), 1.43 (s, 9H), 1.26–1.18 (m, 8H), 1.11–1.04 (m, 2H), 0.87–0.83 (m, 6H); MS (APCI) m/z 217 ($M^+$−55, 50%, −tBu).

(3S,5S)-5-Methyl-3-(toluene-4-sulfonyloxymethyl)-decanoic acid tert-butyl ester 168

A procedure similar to that used to prepare compound 159 was used except that (3S,5S)-3-Hydroxymethyl-5-methyl-decanoic acid tert-butyl ester 167 (4.164 g, 15.29 mmol) was used as a reactant to give 168 as an oil (4.17 g, 64%). $^1$H NMR (400 MHz, $CDCl_3$) δ7.75 (d, J=8.30 Hz, 2H), 7.31 (d, J=8.30 Hz, 2H), 3.97 (dd, J=9.52, 4.15 Hz, 1H), 3.90 (dd, J=9.52, 5.13 Hz, 1H), 2.42 (s, 3H), 2.28, 2.19–2.13 (m, 2H), 1.37 (s, 9H), 1.27–1.01 (m, 11H), 0.85 (t, J=7.08 Hz, 3H), 0.76 (d, J=6.35 Hz, 3H).

(3S,5S)-3-Azidomethyl-5-methyl-decanoic acid tert-butyl ester 169

A procedure similar to that used to prepare compound 160 was used except (3S,5S)-5-methyl-3-(toluene-4-sulfonyloxymethyl)-decanoic acid tert-butyl ester 168 (4.155 g, 9.74 mmol) was used as a reactant to give 169 as an oil (2.77 g, 96%). MS (APCI) m/z 270 (M$^+$–27, 30%, –N$_2$), 214 (M$^+$–87, 100%, –tBu, –N$_2$).

(3S,5S)-3-Aminomethyl-5-methyl-decanoic acid tert-butyl ester 170

A procedure similar to that used to prepare compound 161 was used except that (3S,5S)-3-Azidomethyl-5-methyl-decanoic acid tert-butyl ester 169 (2.50 g, 8.405 mmol) was used as a reactant to give 170 as an oil (1.648 g, 72%). MS (APCI) m/z 272 (M$^+$+1, 100%).

Example 14

(3S,5S)-3-Aminomethyl-5-methyl-decanoic acid

A procedure similar to that used for Example 15 was used except tert-butyl (3S,5S)-3-(aminomethyl)-5-methyldecanoate 170 (1.6 g, 6.00 mmol) was used as a reactant to give Example 16 as a white solid (72%). MS (APCI) m/z 272 (M$^+$+1, 100%). mp=174–175° C.; $^1$H NMR (400 MHz, CD$_3$OD) δ2.91 (dd, J=12.9, 3.91 Hz, 1H), 2.83 (dd, J=12.7, 7.57 Hz, 1H), 2.43 (dd, J=15.6, 3.17 Hz, 1H), 2.19 (dd, J=15.6, 8.80 Hz, 1H), 2.08–2.04 (m, 1H), 1.53 (m, 1H). 1.38–1.27 (m, 7H), 1.78–1.03 (m, 2H), 0.90–0.86 (m, 6H), 0.66 (m, 6H); MS (APCI) m/z 216 (M$^+$+1, 100%), 214 (M$^{-1}$, 100%); [α]$_D$=+21.4 (cl in MeOH).

Example 17

Synthesis of (3R,4R)-3-Aminomethyl-4,5-dimethyl-hexanoic acid

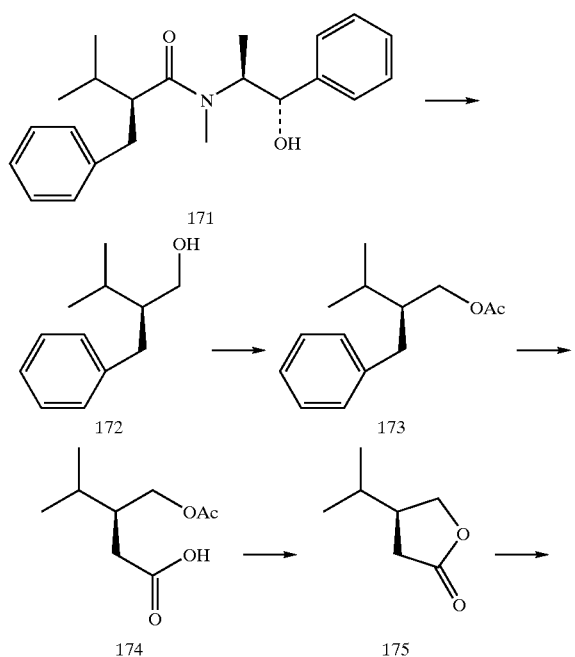

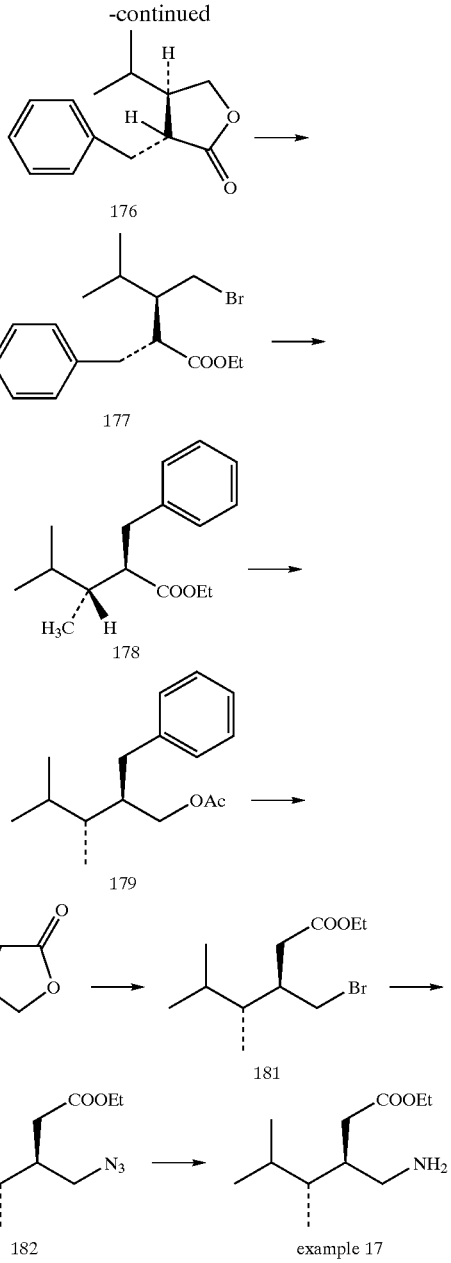

(S)-2-Benzyl-3-methyl-butan-1-ol 172 Ref. JACS 1997;119:6510. Amide 171.

Large Scale Procedure for the Synthesis of Acetic Acid (S)-2-benzyl-3-methyl-butyl ester 173 from 171

A of n-butyl lithium (10 M in hexane, 100 mL, 1000 mmol, 3.9 equiv.) was added to a solution of diisopropylamine (108.9 g, 150.9 mL, 1.076 mol, 4.20 equiv.) in THF (600 mL), at –78° C. The resulting solution was stirred for 10 minutes and warmed to 0° C., and hold at the temperature for 10 minutes. Borane-ammonia complex (31.65 g, 1.025 mmol, and 4.0 equiv) was added in one portion, and the suspension was stirred at 0° C. for 15 minutes, and at 23° C. for 15 minutes, and then cooled to 0° C. A solution of amide 171 (86 g, 256.41 mmol, 1 equiv.) in THF was added to the cold hydride via a cannula over 3 minutes. The reaction was stirred at 23° C. for overnight, then cooled to 0° C. Excess hydride was quenched by the slow addition of 3N HCl (700 mL). The reaction mixture was diluted with more aqueous HCl (3N, 200 mL), and brine and then extracted with ether (4×15 mL). The ether solution was concentrated to a small volume, and 200 mL 2N NaOH was added, and stirred at 23° C. for 2.5 hours. More ether was added and the layers were separated. The aqueous layer was saturated with salt and extracted with ether (3×200 mL). The combined organic was washed with brine and dried on sodium sulfate. The residue was flash chromatographed (Pet. ether-25% ether-TEA ) to give alcohol 172, 50 g. NMR (CDCl$_3$) δ7.35–7.16 (m, 5H, C$_6$H$_5$), 3.55 (app. t, 2H, —CH$_2$OH), 2.71 (dd, 1H, ArCH$_2$CH—), 2.52 (dd, 1H, ArCH$_2$CH), 1.87 (m, 1H, CHCH(Me), 1.67 (m, 1H, CH(Me)$_2$), 0.98 (d, 3H, CH$_3$) and 0.96 (d, 3H, CH$_3$).

A sample 3.3 g was saved for characterization and the rest was immediately acetylated (triethylamine 50 mL, DMAP 4.6 g, acetic acid anhydride 32 mL) overnight at room temperature. Work up followed by chromatography on silica gel eluted with pet ether and then 10% ether in pet ether gave 62 g of 173. NMR (CDCl$_3$) δ7.30–7.14 (m, 5H, C$_6$H$_5$), 3.98 (m, 2H, —CH$_2$OAc), 2.71 (dd, 1H, ArCH$_2$CH—), 2.51 (dd, 1H, ArCH$_2$CH), 1.99 (s, 3H, CH$_3$C═O), 1.82 (m, 1H, CHCH(Me) and CH(Me)$_2$), 0.97 (d, 3H, CH$_3$) and 0.95 (d, 3H, CH$_3$).

(S)-Acetoxymethyl-4-methyl-pentanoic acid 174 and (S)-4-Isopropyl-dihydro-furan-2-one 175

Acetate 173 (15 g, 68.18 mmol) was dissolved in CH$_3$CN (150 mL), carbon tetrachloride (150 mL) and HPLC grade water (300 mL) and stirred. Sodium periodate (262.50 g, 1220 mmol) was added followed by ruthenium chloride (650 mg, 3.136 mmol). After overnight stirring it was diluted with ether and water, and filtered through a pad of Celite. The organic portion was separated and the aqueous phase was further extracted with ether. After drying on magnesium sulfate the solvent was evaporated. Potassium carbonate (42 g) was added to the residue and refluxed overnight in methanol (250 mL) and cooled to room temperature. After evaporation, water was added to dissolve the solid, and conc. HCl was added to bring the pH to 2. Chloroform was added and extracted overnight. The organic phase was separated, and aqueous was further extracted with chloroform. The combined organic extracts were dried, evaporated, and the product was purified on a silica gel column and the compound was eluted with 20% ether in methylene chloride. Fractions were monitored by tlc, and spots were detected with I$_2$/KI solution. Fractions were combined to give 4.6 g of lactone 175. NMR (CDCl$_3$) δ4.38 (dd, 1H, CH$_a$H$_b$O), 3.93 (app. t, 1H, CH$_a$H$_b$O), 2.54 (dd, 1H, CH$_c$H$_d$ C═O), 2.23 (m, 2H, CHCH(Me) and CH$_c$H$_d$ C═O), 1.60 (m, 1H, CH(Me)$_2$), 0.92 (d, 3H, CH$_3$) and 0.85 (d, 3H, CH$_3$).

(3R,4R)-3-Benzyl-4-isopropyl-dihydro-furan-2-one 176

Lithium bis(trimethylsilyl)amide (1.0 M solution in THF, 92 mL, 92 mmol) was added in 3–5 minutes to a solution of (S)-β-(2-propyl)-γ-butyrolactone 175 (11.68 g, 91.25 mmol) in dry THF 100 mL at −78° C. under argon atmosphere. It was stirred for 1 h and a solution of benzyl iodide (21.87 g, 100.37 mmol )in dry THF was added rapidly. Stirring was continued for 1.5 hours and quenched at −78° C. by the addition of a solution of brine followed by ethyl acetate. The organic phase was separated and the aqueous was further extracted with ether. Chromatography on silica gel first eluted with 5% methylene chloride in pet ether, and finally with 10% ether in pet ether gave desired compound 11.6 g, 58%. NMR (CDCl$_3$) δ7.19 (m, 5H, C$_6$H$_5$), 4.02 (app. t, 1H, CH$_a$H$_b$O), 3.87 (dd, 1H, CH$_a$H$_b$O), 2.98 (d, 2H, ArCH$_2$), 2.57 (q, 1H, BnCHC═O), 2.05 (m, 1H, CHCH(Me)$_2$, 1.55 (m, 1H, CH(Me)$_2$), 0.81 (d, 3H, CH$_3$) and 0.72 (d, 3H, CH$_3$).

(2R,3R)-2-Benzyl-3-bromomethyl-4-methyl-pentanoic acid ethyl ester 177

Lactone 176 (6.5 g, 29.8 mmol) was dissolved in abs. ethanol (80 mL) and cooled in ice bath. Anhydrous HBr was bubbled through the solution for 1 hour and stirred at room temperature overnight while maintaining reaction under dry atmosphere. It was poured onto ice cooled mixture of pet ether and brine. The organic phase was separated, and the aqueous was further extracted with pet ether. The combined organic solution was washed repeatedly with cold water and dried. Solvent was removed in vacuo to give crude compound 7.0 g. NMR (CDCl$_3$) δ7.27 (m, 5H, C$_6$H$_5$), 4.02 (m, 2H, CH$_3$CH$_2$O), 3.70 (dd, 1H, CH$_a$H$_b$Br), 3.55 (dd, 1H, CH$_a$H$_b$Br), 2.97 (m, 2H, ArCH$_2$), 2.83 (q, 1H, BnCHC═O), 2.11 (m, 1H, CHCH(Me)$_2$, 1.97 (m, 1H, CH(Me)$_2$), 1.10 (t, 3H, CH$_3$CH$_2$O), 0.96 (d, 3H, CH$_3$) and 0.93 (d, 3H, CH$_3$).

(2R,3R)-2-Benzyl-3,4-dimethyl-pentanoic acid ethyl ester 178

Bromoester 177 (7.25 g, about 80% pure), in ethanol (100 mL) containing triethylamine (3.2 mL) was hydrogenated overnight in the presence of 20% Pd/C (1.0 g). It was filtered through a pad of Celite, and the cake was washed with ethanol. Solvent was evaporated, and the residue was taken up in ether, whereupon solid (Et$_3$N.HCl) separated. The solid was removed by filtration. The filtrate was concentrated, and the procedure was repeated to eliminate all hydrochloride salt. Product was chromatographed on a silica gel column which was eluted with pet ether to give the desired debrominated compound 3.35 g. NMR (CDCl$_3$) δ7.21 (m, 5H, C$_6$H$_5$), 3.95 (m, 2H, CH$_3$CH$_2$O), 2.85 (m, 2H, ArCH$_2$), 2.64 (q, 1H, BnCHC═O), 1.85 (m, 1H, CHCH (Me)$_2$), 1.62 (m, 1H, CH(Me)$_2$), 1.05 (t, 3H, CH$_3$CH$_2$O), 0.95 (d, 3H, CH$_3$) 0.84 (d, 3H, CH$_3$) and 0.82 (d, 3H, CH$_3$). MS gave 290 (M+CH$_3$CN), 249 (M+1), and others at 203. Further elution with ether gave lactone (2.25 g) that was carried over from previous step.

Acetic acid (2R,3R)-2-benzyl-3,4-dimethyl-pentyl-ester 179

Ethyl ester 178 (3.20 g, 12.85 mmol) was dissolved in anhydrous ether and cooled in ice bath under inert atmosphere. Lithium aluminum hydride (500 mg, 13.15 mmol) was added, and the suspension was stirred at room temperature overnight. Excess LAH was destroyed by careful addition of ethyl acetate while the reaction was stirred in ice bath. Saturated sodium sulfate was added cautiously to coagulate the alumina that separated at room temperature as white precipitate. The reaction mixture was diluted with methylene chloride, and anhydrous sodium sulfate was added to dry the mixture. After filtration the solution was concentrated to give an oil 3.0 g.

The material (3.0 g) was dissolved in dichloromethane (30 mL) and triethylamine (2.5 mL), DMAP (200 mg), and acetic anhydride (1.5 mL) were added. It was stirred at room temperature for 3 hours, and diluted with ether. The ether solution was washed with waster, 1N HCl, saturated sodium bicarbonate, brine and dried. The solution was concentrated in vacuo to give the acetoxy compound 179 3.16 g. NMR (CDCl$_3$) δ7.19 (m, 5H, C$_6$H$_5$), 4.03 (m, 2H, CH$_3$CH$_2$O), 2.69 (m, 2H, ArCH$_2$), 2.09 (m, 1H, BnCHCH$_2$O), 2.02 (s, 3H, CH$_3$C═O), 1.68 (m, 1H, CH$_3$CHCH(Me)$_2$, 1.23 (m, 1H, CH(Me)$_2$), 0.87 (d, 3H, CH$_3$), 0.84 (d, 3H, CH$_3$) and 0.81 (d, 3H, CH$_3$).

(R)-4-((R)-1,2-Dimethyl-propyl)-dihydro-furan-2-one 180

To a solution of aromatic compound 179 (5.0 g, 20.16 mmol) in HPLC grade acetonitrile (60 mL), carbon tetrachloride (60 mL), and water (120 mL) was added sodium periodate (86.24 g, 403.32 mmol, 20 equiv.), followed by RuCl$_3$ (414 mg, 10 mol %). The mixture was stirred vigorously overnight at room temperature, and diluted with methylene chloride (400 mL). The mixture was filtered through a pad of Celite to remove the solid precipitate. The organic portion was separated, and the aqueous was further extracted with methylene chloride. After the combined organic portions concentrated, the residue was dissolved in ether and applied to a column of Florisil. The compound was eluted with 3% methanol in ether, evaporated to a paste that was dissolved in methanol (100 mL). Potassium carbonate (8.0 g) was added, and the mixture was refluxed for 6 hours. The solvent was evaporated, and the solid residue was dissolved in water. The pH was adjusted to 2 by the careful addition of concentrated HCl while being cooled in ice water bath and stirred. Chloroform (200 mL) was added to the solution and stirred as such overnight at room temperature. The organic phase was separated, and the aqueous portion was further extracted with chloroform. After drying, the solvent was evaporated to give the lactone 180 5.0 g. NMR (CDCl$_3$) δ4.36 (app. t, 1H, CH$_a$H$_b$O), 3.85 (app. t, 1H, CH$_a$H$_b$O), 2.46 (m, 2H, CH$_c$H$_d$ C=O), 2.13 (m, 2H, CHCH$_2$C=O), 1.60 (m, 1H, CH(Me)$_2$), 1.35 (m, 1H, CH$_3$CHCH(Me)$_2$), 0.86 (d, 3H, CH$_3$) and 0.72 (t, 3H, CH$_3$). (3R,4R)-3-Bromomethyl-4,5-dimethyl-hexanoic acid ethyl ester 181

Lactone 180 (5.0 g) was dissolved in absolute ethanol (25 mL) and flushed with argon. While being cooled in ice water bath, anhydrous HBr gas was bubbled through the mixture for 45 minutes and allowed to stand at room temperature overnight. The mixture was poured into ice-salt water and hexane. The organic phase was separated, and the aqueous was further extracted with hexane. The combined organic extract was dried and evaporated. Flash chromatography with 10% ether in pet ether on a silica gel column gave the bromoester 181 3.54 g. NMR (CDCl$_3$) δ4.14 (q, 2H, CH$_3$H$_2$O), 3.60 (dd, 1H, CH$_a$H$_b$Br), 3.41 (dd, 1H, CH$_c$H$_b$ Br), 2.54 (dd, 1H, CH$_a$H$_b$C=O), 2.44 (dd, 1H, CH$_a$H$_b$C=O), 2.22 (m, 1H, O=CCH$_2$CHCH$_2$Br), 1.67 (m, 1H, CHCH$_3$CH(Me)$_2$, 1.37 (m, 1H, CH(Me)$_2$), 1.26 (t, 3H, CH$_3$CH$_2$O), 0.94 (d, 3H, CHCH$_3$CH(Me)$_2$, 0.81 (d, 3H, ((CH$_3$)$_2$)CHCH$_3$CH) and 0.79 (d, 3H, ((CH$_3$)$_2$)CHCH$_3$CH). (3R,4R)-3-Azidomethyl-4,5-dimethyl-hexanoic acid ethyl ester 182 and Example 17 (3R,4R)-3-Aminomethyl-4,5-dimethyl-hexanoic acid Bromoester 181 (3.54 g, 13.34 mmol), sodium azide (1.04 g, 16.13 mmol) in anhydrous DMF (8.0 mL) was stirred at room temperature overnight. Water (16 mL) and hexane were added, the organic portion was separated, and the aqueous portion was further extracted with hexane. It was dried and evaporated to give azido ester 3.0 g. NMR (CDCl$_3$) δ4.14 (q, 2H, CH$_3$H$_2$O), 3.48 (dd, 1H, CH$_a$H$_b$N$_3$), 3.21 (dd, 1H, CH$_c$H$_b$N$_3$), 2.34 (m 2H, CH$_a$H$_b$C=O), 2.20 (m, 1H, O=CCH$_2$CHCH$_2$ N$_3$), 1.60 (m, 1H, CHCH$_3$CH (Me)$_2$. Compound was submitted for hydrogenation (HPL, 66480×100). The hydrogenated crude was dissolved in 6N HCl and refluxed overnight. The solvent was evaporated in vacuo the residue was azeotroped with toluene. The crude was further purified by loading onto an ion exchange column chromatography (Dowex 50Wb×8–100), washed to neutral eluent with HPLC grade water followed by elution of compound with 0.5N NH$_4$OH solution. Crystallization of product from methanol gave 720 mg. NMR (CD$_3$OD) δ3.04 (dd, 1H, CH$_a$H$_b$NH$_2$), 2.82 (dd, 1H, CH$_c$H$_b$ NH$_2$), 2.52 (dd, 1H, CH$_a$H$_b$C=O), 2.40 (dd, 1H, CH$_a$H$_b$C=O), 2.07 (m, 1H, O=CCH$_2$CHCH$_2$NH$_2$), 1.67 (m, 1H, CHCH$_3$CH(Me)$_2$, 1.35 (m, 1H, CH(Me)$_2$), 0.97 (d, 3H, CHCH$_3$CH(Me)$_2$, 0.88 (d, 3H, ((CH$_3$)$_2$)CHCH$_3$CH) and 0.83 (d, 3H, ((CH$_3$)$_2$) CHCH$_3$CH). [α]$_D$–5.3 (c, MeOH, 1.9 mg/mL). Anal. Calcd for C$_9$H$_{19}$NO$_2$: C, 62.39; H, 11.05; N 8.08. Found C, 62.01; H, 11.35; N, 7.88. MS showed ions at 215 (M+CH$_3$CN), 197 (M+Na$^+$), 174 (M+H$^+$). Analysis of derivative by reverse phase HPLC, Hypersil BDS C$_{18}$ 5 micron and mobile phase 50/50 CH$_3$CN-water containing 0.1%TFA gave 99.93% purity at retention time of 8.21 minutes.

Examples 18–20
Synthesis of 3-Aminomethyl-4-isopropyl-heptanoic acid

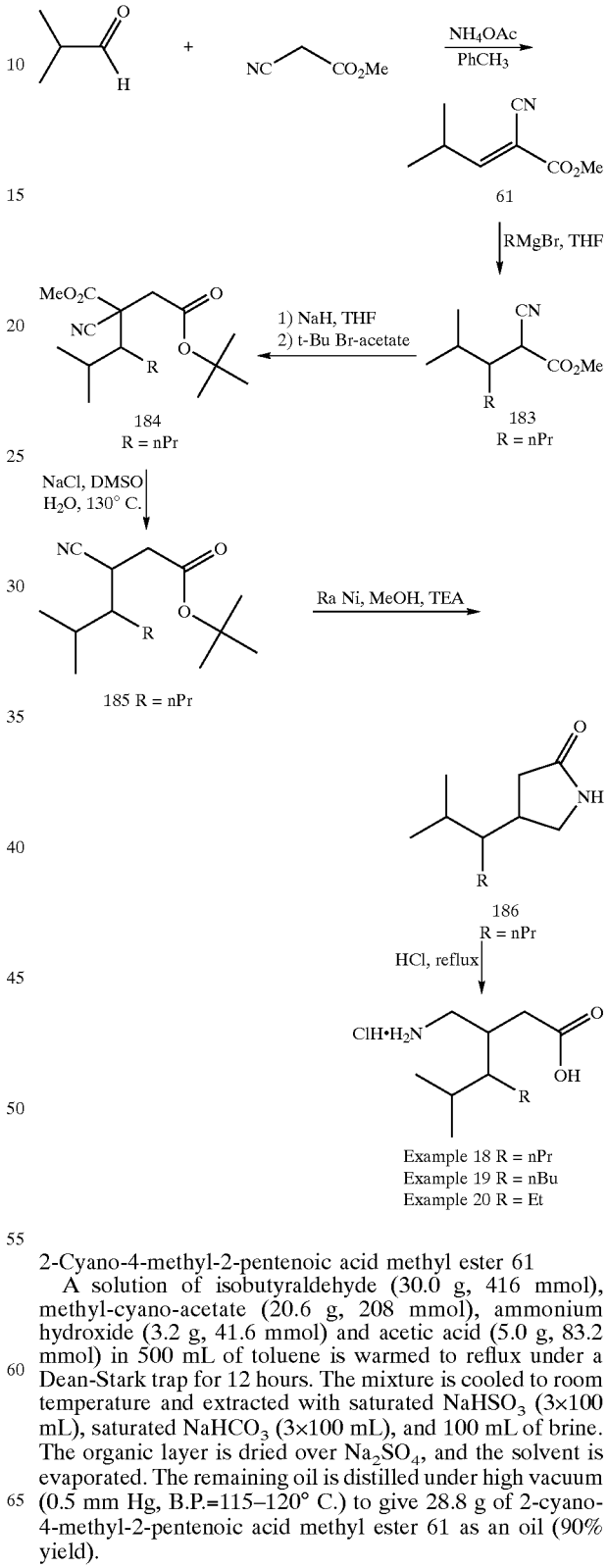

2-Cyano-4-methyl-2-pentenoic acid methyl ester 61

A solution of isobutyraldehyde (30.0 g, 416 mmol), methyl-cyano-acetate (20.6 g, 208 mmol), ammonium hydroxide (3.2 g, 41.6 mmol) and acetic acid (5.0 g, 83.2 mmol) in 500 mL of toluene is warmed to reflux under a Dean-Stark trap for 12 hours. The mixture is cooled to room temperature and extracted with saturated NaHSO$_3$ (3×100 mL), saturated NaHCO$_3$ (3×100 mL), and 100 mL of brine. The organic layer is dried over Na$_2$SO$_4$, and the solvent is evaporated. The remaining oil is distilled under high vacuum (0.5 mm Hg, B.P.=115–120° C.) to give 28.8 g of 2-cyano-4-methyl-2-pentenoic acid methyl ester 61 as an oil (90% yield).

2-Cyano-3-isopropyl-hexanoic acid methyl ester 183

A 2.0 M solution of propyl magnesium chloride in Et$_2$O (9.8 mL, 19.6 mmol) is added to a solution of 2-cyano4-methyl-2-pentenoic acid (3.0 g, 19.6 mmol) in 50 mL of THF which is cooled in an IPA/dry ice bath to −40° C. under argon. The solution is stirred for 4 hours, and the reaction is quenched by addition of 50 mL of saturated KH$_2$PO$_4$. The THF is evaporated, and the remaining oil is chromatographed under medium pressure over silica gel with 50% CH$_2$Cl$_2$/hexane. Yield=1.9 g (50%) of 2-cyano-3-isopropyl-hexanoic acid methyl ester as an oil.

2-Cyano-2-(1-isopropyl-butyl)-succinic acid 4-tert-butyl ester 1-methyl ester 184

A solution of 2-cyano-3-isopropyl-hexanoic acid methyl ester (1.9 g, 9.6 mmol) in 10 mL of THF is added to a slurry of NaH (washed with hexane, 0.23 g, 9.6 mmol) in 20 mL of THF which is cooled in an ice water bath under argon. The solution is stirred for 10 minutes, and t-butyl bromoacetate (2.1 g, 10.6 mmol) is added. The solution is warmed to room temperature. After 12 hours, the reaction is quenched by addition of 50 mL of saturated KH$_2$PO$_4$ and the THF is evaporated. The organic products are extracted into Et$_2$O (3×50 mL), and the combined organic layers are dried over MgSO$_4$. The solvent is evaporated, and the remaining oil is chromographed under medium pressure over silica gel in 25% hexane/CH$_2$Cl$_2$. Yield of 2-cyano-2-(1-isopropyl-butyl)-succinic acid 4-tert-butyl ester 1-methyl ester=1.3 g (42%) as an oil.

3-Cyano-4-isopropyl-heptanoic acid t-butyl ester 185

A mixture of 2-cyano-2-(1-isopropyl-butyl)-succinic acid 4-tert-butyl ester 1-methyl ester (1.3 g, 4.2 mmol), NaCl (0.25 g, 4.2 mmol), and H$_2$O (0.15 g, 8.3 mmol) in 25 mL of DMSO is warmed to 130° C. for 12 hours. The mixture is cooled to room temperature and diluted with 100 mL of brine. The organic products are extracted into Et$_2$O (3×50 mL). The organic layers are combined and washed with 50 mL of H$_2$O and 50 mL of brine. Drying over Na$_2$SO$_4$ and evaporation of the solvent gives 0.8 g (75% yield) of 3-cyano-4-isopropyl-heptanoic acid t-butyl ester as an oil.

4-(1-Isopropyl-butyl)-2-pyrrolidone 186

3-Cyano-4-isopropyl-heptanoic acid t-butyl ester (0.8 g, 3.2 mmol) is reduced under 50 psi of H$_2$ in MeOH containing TEA and Ra Ni. When the theoretical amount of H$_2$ is taken up, the catalyst is removed by filtration, and the solvent is evaporated to give 0.6 g (100% yield) of 4-(1-isopropyl-butyl)-2-pyrrolidone as an oil.

Example 18
3-Aminomethyl-4-isopropyl-heptanoic acid 4-(1-Isopropyl-butyl)-2-pyrrolidone (0.6 g, 2.3 mmol) is warmed to reflux in 50 mL of 6.0 M HCl for 12 hours. The solution is cooled to room temperature and filtered through Celite. The filtrate is evaporated, and the solid remaining is recrystallized from MeOH/EtOAc. Yield 0.035 g (6% yield) of 3-aminomethyl-4-isopropyl-heptanoic acid as an HCl salt, mp 160–170° C. $^1$H NMR (CD$_3$OD) δ0.9 (m, 9H), 1.30 (m, 5H), 1.78 (m, 1H), 2.30 (m, 2H), 2.45 (m, 1H), 2.95 (m, 2H). MS (APCI, CH$_3$CN, H$_2$O) 201 (M$^+$, 100%).

Example 19
3-Aminomethyl-4-isopropyl-octanoic acid

Prepared according to the procedure of Example 18. Yield=0.13 g (15%) of 3-aminomethyl-4-isopropyl-octanoic acid. mp=160–170° C. $^1$H NMR (CD$_3$OD) δ0.9 (m, 9H), 1.30 (m, 7H), 1.78 (m, 1H), 2.30 (m, 1H), 2.45 (m, 2H), 2.95 (m, 2H). MS (APCI, CH$_3$CN, H$_2$O) 198 (M−17, 100%), 216 (M$^+$, 50%).

Example 20
3-Aminomethyl-4-isopropyl-hexanoic acid

Prepared according to the procedure of Example 18. Yield=0.11 g (42%) of 3-aminomethyl-4-isopropyl-hexanoic acid. mp=170–180° C. $^1$H NMR (CD$_3$OD) δ0.9 (m, 9H), 1.18 (m, 1H), 1.39 (m, 3H), 1.78 (m, 1H), 2.30 (m, 1H), 2.45 (m, 1H), 2.95 (m, 2H). MS (APCI, CH$_3$CN, H$_2$O) 188 (M$^+$, 100%).

Example 21

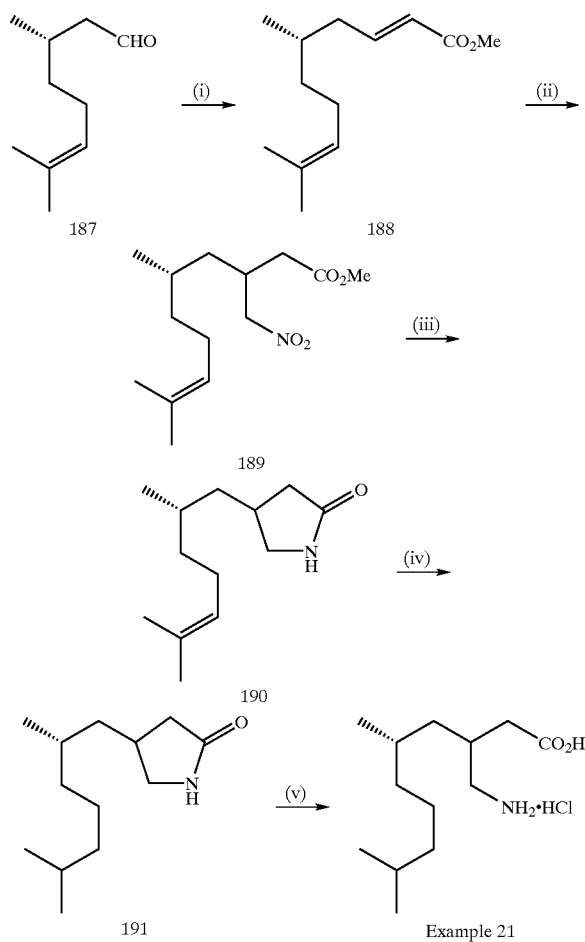

Example 21

(i) MeO$_2$CCH=PPh$_3$, THF, 40° C.; (ii) MeNO$_2$, DBU; (iii) Raney Nickel, H$_2$, MeOH; (iv) Pd-C, MeOH, H$_2$; (v) 6N HCl

Synthesis of the unsaturated ester 188

(S)-(−)-citronellal 187 (2.0 mL, 11.03 mmol) was stirred at 40° C. in dry tetrahydrofuran (30 mL) with methyl triphenylphosphoranylidene acetate (3.69 g, 11.03 mmol). After 8 hours the mixture was cooled to room temperature and stirred overnight. The solvent was removed in vacuo and the residue stirred with n-pentane (50 mL). After 1 hour the solid was removed by filtration and the solvent removed in vacuo to give an oil which was purified by flash chromatography (silica, ethyl acetate:heptane 1:9) to give 2.05 g (88%) of 188 as a clear oil. $^1$H NMR (400 MHz) (CDCl$_3$) δ0.90 (3H, d, J=6 Hz); 1.12–1.40 (2H, m); 1.60 (3H, s); 1.62 (1H, m); 1.68 (3H, s); 2.01 (3H, m); 2.21 (1H, m); 3.73 (3H, s); 5.08 (1H, m); 5.82 (1H, d, J=16 Hz); 6.94 (1H, m). MS (CI$^+$) (m/z): 211 (MH$^+$, 75%), 179 (78%), 151 (100%). IR (thin film) (cm$^{-1}$) v: 1271, 1436, 1728, 2917.

Synthesis of the nitroester 189

The ester 188 (2.02 g, 9.6 mmol) was dissolved in nitromethane (25 mL) with 1,8-diazabicyclo[5,4,0]undec-7-ene (1.44 mL, 9.6 mmol) and stirred at room temperature. After 23 hours the mixture was diluted with diethyl ether (150 mL) and washed with water (50 mL) and then 2N HCl (50 mL). The organic phase was collected, dried (MgSO$_4$), and the solvent removed in vacuo. The residue was purified by flash chromatography (silica, ethyl acetate:heptane 3:7) to give 2.26 g (87%) of 189 as a clear oil. Note that this and all subsequent compounds are equimolar mixtures of 2 diastereoisomers. $^1$H NMR (400 MHz) (CDCl$_3$) δ0.90 (2×3H, each d, J=6 Hz); 1.09–1.58 (10H, m); 1.602 (6H, s); 1.685 (6H, s); 1.94 (4H, m); 2.42 (4H, m); 2.66 (2H, m); 3.70 (6H, s); 4.42 (4H, m); 5.07 (2H, m). MS (CI$^+$) (m/z): 272 (MH$^+$, 90%), 240 (100%), 151 (100%). IR (thin film) (cm$^{-1}$) ν: 1554, 1739, 2918.

Synthesis of the lactam 191

The nitro ester 189 (2.09 g, 7.7 mmol) was dissolved in methanol (75 mL) and shaken over Raney Nickel (catalytic, prewashed with water and then methanol) under an atmosphere of hydrogen gas (39 psi) at 35° C. After 17 hours the mixture was filtered through Celite. The solvent was removed in vacuo to give an oil. $^1$H NMR showed there had been partial reduction of the double bond so this was carried on without further purification. A sample of this partial reduced product (440 mg, 2.1 mmol) was dissolved in methanol (40 mL) and shaken over 5% Pd-C under an atmosphere of hydrogen gas. After 18 hours the catalyst was removed by filtration through Celite to obtain 442 mg (99% from partial reduced material) as a clear oil which did not need purification. Note that this and all subsequent compounds are equimolar mixtures of 2 diastereoisomers. $^1$H NMR (400 MHz) (CDCl$_3$) δ: 0.88 (18H, m); 1.04–1.58 (20H, m); 1.96 (2H, m); 2.40 (2H, m); 2.58 (2H, m); 2.98 (2H, m); (3.45 (2H, m), 5.82 (2H, br s). MS (CI$^+$) (m/z): 212 (MH$^+$, 100%).

Synthesis of Example 21

The lactam 191 (428 mg, 2.0 mmol) was heated to reflux in 6N HCl (20 mL). After 5 hours the mixture was cooled to room temperature and washed with dichloromethane (2×10 mL). The aqueous phase was collected and the solvent removed in vacuo. The residue was dissolved in water (10 mL) and freeze-dried to give 382 mg (71%) of Example 34 as a white solid. Note that this compound is an equimolar mixture of 2 diastereoisomers. $^1$H NMR (400 MHz) (d$_6$-DMSO) δ0.82 (18H, m); 0.95–1.55 (20H, m); 2.05–2.45 (6H, m); 2.75 (4H, m); 7.98 (6H, br s). MS (CI$^+$) (m/z): 230 ([MH-HCl]$^+$, 90%), 212 (100%). Microanalysis: Calculated for C$_{13}$H$_{28}$NO$_2$Cl: C, 58.74; H, 10.62; N, 5.27. Found: C, 58.46; H, 10.50; N, 5.33.

To one skilled in the art, the use of (R)-(+)-citronellal would afford compounds of opposite C5-stereochemistry to Example 21.

What is claimed is:

1. A compound of Formula I

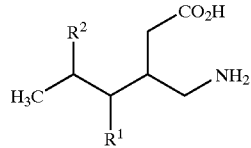

I or a pharmaceutically acceptable salt thereof wherein:

R$^1$ is hydrogen, straight or branched alkyl of from 1 to 6 carbon atoms or phenyl;

R$^2$ is straight or branched alkyl of from 4 to 8 carbon atoms,
straight or branched alkenyl of from 2 to 8 carbon atoms,
cycloalkyl of from 3 to 7 carbon atoms,
alkoxy of from 1 to 6 carbon atoms,
alkylcycloalkyl,
alkylalkoxy,
alkyl OH,
alkylphenyl,
alkylphenoxy, and
substituted phenyl.

2. A compound according to claim 1 wherein R$^1$ is hydrogen and R$^2$ is straight or branched alkyl of from 4 to 8 carbon atoms.

3. A compound or a pharmaceutically acceptable salt thereof according to claim 1 and selected from:

3-Aminomethyl-5-methyl-nonanoic acid;
3-Aminomethyl-5-methyl-decanoic acid;
3-Aminomethyl-5-methyl-undecanoic acid;
3-Aminomethyl-5-methyl-dodecanoic acid;
3-Aminomethyl-5-methyl-tridecanoic acid;
3-Aminomethyl-5-cyclopropyl-hexanoic acid;
3-Aminomethyl-5-cyclobutyl-hexanoic acid;
3-Aminomethyl-5-trifluoromethyl-hexanoic acid;
3-Aminomethyl-5-(2-chlorophenyl)-hexanoic acid;
3-Aminomethyl-5-(3-chlorophenyl)-hexanoic acid;
3-Aminomethyl-5-(4-chlorophenyl)-hexanoic acid;
3-Aminomethyl-5-(2-methoxyphenyl)-hexanoic acid;
3-Aminomethyl-5-(3-methoxyphenyl)-hexanoic acid;
3-Aminomethyl-5-(4-methoxyphenyl)-hexanoic acid; and
3-Aminomethyl-5-(phenylmethyl)-hexanoic acid.

4. A compound or a pharmaceutically acceptable salt thereof wherein said compound is (3S,5R)-3-Aminomethyl-5-methyl-heptanoic acid.

5. A compound or a pharmaceutically acceptable salt thereof wherein said compound is (3S,5R)-3-Aminomethyl-5-methyl-octanoic acid.

6. A compound or a pharmaceutically acceptable salt thereof according to claim 1 wherein said compound is (3S,5R)-3-Aminomethyl-5-methyl-nonanoic acid.

7. A compound or a pharmaceutically acceptable salt thereof according to claim 1 wherein said compound is (3S,5R)-3-Aminomethyl-5-methyl-decanoic acid.

8. A compound or a pharmaceutically acceptable salt thereof according to claim 1 wherein said compound is (3S,5R)-3-Aminomethyl-5-methyl-undecanoic acid.

9. A compound or a pharmaceutically acceptable salt thereof according to claim 1 wherein said compound is (3S,5R)-3-Aminomethyl-5-methyl-dodecanoic acid.

10. A compound according to claim 1 and selected from:

(3S,5R)-3-Aminomethyl-5,9-dimethyl-decanoic acid;
(3S,5R)-3-Aminomethyl-5-methyl-heptanoic acid;
(3S,5R)-3-Aminomethyl-5,7-dimethyl-octanoic acid;
(3S,5R)-3-Aminomethyl-5,10-dimethyl-undecanoic acid;
(3S,5R)-3-Aminomethyl-6-cyclopropyl-5-methyl-hexanoic acid;
(3S,5R)-3-Aminomethyl-6-cyclobutyl-5-methyl-hexanoic acid;

(3S,5R)-3-Aminomethyl-6-cyclopentyl-5-methyl-hexanoic acid;
(3S,5R)-3-Aminomethyl-6-cyclohexyl-5-methyl-hexanoic acid;
(3S,5R)-3-Aminomethyl-7-cyclopropyl-5-methyl-heptanoic acid;
(3S,5R)-3-Aminomethyl-7-cyclobutyl-5-methyl-heptanoic acid;
(3S,5R)-3-Aminomethyl-7-cyclopentyl-5-methyl-heptanoic acid;
(3S,5R)-3-Aminomethyl-7-cyclohexyl-5-methyl-heptanoic acid;
(3S,5R)-3-Aminomethyl-8-cyclopropyl-5-methyl-octanoic acid;
(3S,5R)-3-Aminomethyl-8-cyclobutyl-5-methyl-octanoic acid;
(3S,5R)-3-Aminomethyl-8-cyclopentyl-5-methyl-octanoic acid;
(3S,5R)-3-Aminomethyl-8-cyclohexyl-5-methyl-octanoic acid;
(3S,5R)-3-Aminomethyl-8-fluoro-5-methyl-octanoic acid; and
(3S,5R)-3-Aminomethyl-9-fluoro-5-methyl-nonanoic acid.

11. A compound according to claim 1 and selected from:

(3S,5S)-3-Aminomethyl-5-methoxy-hexanoic acid;
(3S,5S)-3-Aminomethyl-5-ethoxy-hexanoic acid;
(3S,5S)-3-Aminomethyl-5-propoxy-hexanoic acid;
(3S,5S)-3-Aminomethyl-5-isopropoxy-hexanoic acid;
(3S,5S)-3-Aminomethyl-5-tert-butoxy-hexanoic acid;
(3S,5S)-3-Aminomethyl-5-fluoromethoxy-hexanoic acid;
(3S,5S)-3-Aminomethyl-5-(2-fluoro-ethoxy)-hexanoic acid;
(3S,5S)-3-Aminomethyl-5-(3,3,3-trifluoro-propoxy)-hexanoic acid;
(3S,5S)-3-Aminomethyl-5-phenoxy-hexanoic acid;
(3S,5S)-3-Aminomethyl-5-(4-chloro-phenoxy)-hexanoic acid;
(3S,5S)-3-Aminomethyl-5-(3-chloro-phenoxy)-hexanoic acid;
(3S,5S)-3-Aminomethyl-5-(2-chloro-phenoxy)-hexanoic acid;
(3S,5S)-3-Aminomethyl-5-(4-fluoro-phenoxy)-hexanoic acid;
(3S,5S)-3-Aminomethyl-5-(3-fluoro-phenoxy)-hexanoic acid;
(3S,5S)-3-Aminomethyl-5-(2-fluoro-phenoxy)-hexanoic acid;
(3S,5S)-3-Aminomethyl-5-(4-methoxy-phenoxy)-hexanoic acid;
(3S,5S)-3-Aminomethyl-5-(3-methoxy-phenoxy)-hexanoic acid;
(3S,5S)-3-Aminomethyl-5-(2-methoxy-phenoxy)-hexanoic acid;
(3S,5S)-3-Aminomethyl-5-(4-nitro-phenoxy)-hexanoic acid;
(3S,5S)-3-Aminomethyl-5-(3-nitro-phenoxy)-hexanoic acid;
(3S,5S)-3-Aminomethyl-5-(2-nitro-phenoxy)-hexanoic acid;
(3S,5S)-3-Aminomethyl-5-methyl-6-propoxy-hexanoic acid;
(3S,5S)-3-Aminomethyl-6-isopropoxy-5-methyl-hexanoic acid;
(3S,5S)-3-Aminomethyl-6-tert-butoxy-5-methyl-hexanoic acid;
(3S,5S)-3-Aminomethyl-6-fluoromethoxy-5-methyl-hexanoic acid;
(3S,5S)-3-Aminomethyl-6-(2-fluoro-ethoxy)-5-methyl-hexanoic acid;
(3S,5S)-3-Aminomethyl-5-methyl-6-(3,3,3-trifluoro-propoxy)-hexanoic acid;
(3S,5S)-3-Aminomethyl-5-methyl-6-phenoxy-hexanoic acid;
(3S,5S)-3-Aminomethyl-6-(4-chloro-phenoxy)-5-methyl-hexanoic acid;
(3S,5S)-3-Aminomethyl-6-(3-chloro-phenoxy)-5-methyl-hexanoic acid;
(3S,5S)-3-Aminomethyl-6-(2-chloro-phenoxy)-5-methyl-hexanoic acid;
(3S,5S)-3-Aminomethyl-6-(4-fluoro-phenoxy)-5-methyl-hexanoic acid;
(3S,5S)-3-Aminomethyl-6-(3-fluoro-phenoxy)-5-methyl-hexanoic acid;
(3S,5S)-3-Aminomethyl-6-(2-fluoro-phenoxy)-5-methyl-hexanoic acid;
(3S,5S)-3-Aminomethyl-6-(4-methoxy-phenoxy)-5-methyl-hexanoic acid;
(3S,5S)-3-Aminomethyl-6-(3-methoxy-phenoxy)-5-methyl-hexanoic acid;
(3S,5S)-3-Aminomethyl-6-(2-methoxy-phenoxy)-5-methyl-hexanoic acid;
(3S,5S)-3-Aminomethyl-5-methyl 6-(4-trifluoromethyl-phenoxy)-hexanoic acid;
(3S,5S)-3-Aminomethyl-5-methyl 6-(3-trifluoromethyl-phenoxy)-hexanoic acid;
(3S,5S)-3-Aminomethyl-5-methyl 6-(2-trifluoromethyl-phenoxy)-hexanoic acid;
(3S,5S)-3-Aminomethyl-5-methyl 6-(4-nitro-phenoxy)-hexanoic acid;
(3S,5S)-3-Aminomethyl-5-methyl 6-(3-nitro-phenoxy)-hexanoic acid;
(3S,5S)-3-Aminomethyl-5-methyl 6-(2-nitro-phenoxy)-hexanoic acid;
(3S,5S)-3-Aminomethyl-6-benzyloxy-5-methyl-hexanoic acid;
(3S,5S)-3-Aminomethyl-7-hydroxy-5-methyl-heptanoic acid;
(3S,5S)-3-Aminomethyl-7-methoxy-5-methyl-heptanoic acid;
(3S,5S)-3-Aminomethyl-5-methyl-7-propoxy-heptanoic acid;
(3S,5S)-3-Aminomethyl-7-isopropoxy-5-methyl-heptanoic acid;
(3S,5S)-3-Aminomethyl-7-tert-butoxy-5-methyl-heptanoic acid;
(3S,5S)-3-Aminomethyl-7-fluoromethoxy-5-methyl-heptanoic acid;
(3S,5S)-3-Aminomethyl-7-(2-fluoro-ethoxy)-5-methyl-heptanoic acid;
(3S,5S)-3-Aminomethyl-5-methyl-7-(3,3,3-trifluoro-propoxy)-heptanoic acid;
(3S,5S)-3-Aminomethyl-7-benzyloxy-5-methyl-heptanoic acid;
(3S,5S)-3-Aminomethyl-5-methyl-7-phenoxy-heptanoic acid;
(3S,5S)-3-Aminomethyl-7-(4-chloro-phenoxy)-5-methyl-heptanoic acid;
(3S,5S)-3-Aminomethyl-7-(3-chloro-phenoxy)-5-methyl-heptanoic acid;
(3S,5S)-3-Aminomethyl-7-(2-chloro-phenoxy)-5-methyl-heptanoic acid;
(3S,5S)-3-Aminomethyl-7-(4-fluoro-phenoxy)-5-methyl-heptanoic acid;
(3S,5S)-3-Aminomethyl-7-(3-fluoro-phenoxy)-5-methyl-heptanoic acid;

(3S,5S)-3-Aminomethyl-7-(2-fluoro-phenoxy)-5-methyl-heptanoic acid;
(3S,5S)-3-Aminomethyl-7-(4-methoxy-phenoxy)-5-methyl-heptanoic acid;
(3S,5S)-3-Aminomethyl-7-(3-methoxy-phenoxy)-5-methyl-heptanoic acid;
(3S,5S)-3-Aminomethyl-7-(2-methoxy-phenoxy)-5-methyl-heptanoic acid;
(3S,5S)-3-Aminomethyl-5-methyl-7-(4-trifluoromethyl-phenoxy)-heptanoic acid;
(3S,5S)-3-Aminomethyl-5-methyl-7-(3-trifluoromethyl-phenoxy)-heptanoic acid;
(3S,5S)-3-Aminomethyl-5-methyl-7-(2-trifluoromethyl-phenoxy)-heptanoic acid;
(3S,5S)-3-Aminomethyl-5-methyl-7-(4-nitro-phenoxy)-heptanoic acid;
(3S,5S)-3-Aminomethyl-5-methyl-7-(3-nitro-phenoxy)-heptanoic acid;
(3S,5S)-3-Aminomethyl-5-methyl-7-(2-nitro-phenoxy)-heptanoic acid;
(3S,5S)-3-Aminomethyl-5-methyl-6-phenyl-hexanoic acid;
(3S,5S)-3-Aminomethyl-6-(4-chloro-phenyl)-5-methyl-hexanoic acid;
(3S,5S)-3-Aminomethyl-6-(3-chloro-phenyl)-5-methyl-hexanoic acid;
(3S,5S)-3-Aminomethyl-6-(2-chloro-phenyl)-5-methyl-hexanoic acid;
(3S,5S)-3-Aminomethyl-6-(4-methoxy-phenyl)-5-methyl-hexanoic acid;
(3S,5S)-3-Aminomethyl-6-(3-methoxy-phenyl)-5-methyl-hexanoic acid;
(3S,5S)-3-Aminomethyl-6-(2-methoxy-phenyl)-5-methyl-hexanoic acid;
(3S,5S)-3-Aminomethyl-6-(3-fluoro-phenyl)-5-methyl-hexanoic acid;
(3S,5S)-3-Aminomethyl-6-(2-fluoro-phenyl)-5-methyl-hexanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid;
(3S,5S)-3-Aminomethyl-5-methyl-hept-6-enoic acid;
(3S,5R)-3-Aminomethyl-5-methyl-oct-7-enoic acid;
(3S,5R)-3-Aminomethyl-5-methyl-non-8-enoic acid;
(E)-(3S,5S)-3-Aminomethyl-5-methyl-oct-6-enoic acid;
(Z)-(3S,5S)-3-Aminomethyl-5-methyl-oct-6-enoic acid;
(Z)-(3S,5S)-3-Aminomethyl-5-methyl-non-6-enoic acid;
(E)-(3S,5S)-3-Aminomethyl-5-methyl-non-6-enoic acid;
(E)-(3S,5R)-3-Aminomethyl-5-methyl-non-7-enoic acid;
(Z)-(3S,5R)-3-Aminomethyl-5-methyl-non-7-enoic acid;
(Z)-(3S,5R)-3-Aminomethyl-5-methyl-dec-7-enoic acid;
(E)-(3S,5R)-3-Aminomethyl-5-methyl-undec-7-enoic acid;
(3S,5S)-3-Aminomethyl-5,6,6-trimethyl-heptanoic acid;
(3S,5S)-3-Aminomethyl-5-cyclopropyl-hexanoic acid;
(3S,5S)-3-Aminomethyl-5-cyclobutyl-hexanoic acid;
(3S,5R)-3-Aminomethyl-5-methyl-8-phenyl-octanoic acid;
(3S,5S)-3-Aminomethyl-5-methyl-6-phenyl-hexanoic acid; and
(3S,5R)-3-Aminomethyl-5-methyl-7-phenyl-heptanoic acid.

12. A pharmaceutical composition comprising a therapeutically effective amount of a compound according to claim 1 and a pharmaceutically acceptable carrier.

13. A method for treating epilepsy, faintness attacks, hypokinesia, cranial disorders, neurodegenerative disorders, depression, anxiety, panic, pain, neuropathological disorders, sleep disorders, IBS or gastric damage comprising administering a therapeutically effective amount of a compound according to claim 1 to a mammal in need of said treatment.

14. A compound or a pharmaceutically acceptable salt thereof according to claim 1 wherein $R^2$ is substituted phenyl, or alkylphenyl.

15. A compound or a pharmaceutically acceptable salt thereof according to claim 1 wherein $R^2$ is alkylphenoxy.

16. A compound or a pharmaceutically acceptable salt thereof according to claim 1 wherein $R^2$ is cycloalkyl or alkylcycloalkyl.

17. A compound or a pharmaceutically acceptable salt thereof according to claim 1 wherein $R^2$ is alkylhydroxy.

18. A compound or a pharmaceutically acceptable salt thereof wherein said compound is selected from:

3-Aminomethyl-5-methylheptanoic acid;
3-Aminomethyl-5-methyl-octanoic acid;
3-Aminomethyl-4,5-dimethyl-hexanoic acid;
(3S,4S)3-Aminomethyl-4,5-dimethyl-hexanoic acid;
(3R,4R)3-Aminomethyl-4,5-dimethyl-hexanoic acid MP;
3-Aminomethyl-4-isopropyl-hexanoic acid;
3-Aminomethyl-4-isopropyl-heptanoic acid;
(3S,5S)-3-Aminomethyl-6-fluoro-5-methyl-hexanoic acid;
(3S,5S)-3-Aminomethyl-7-fluoro-5-methyl-heptanoic acid;
(3S,5S)-3-Aminomethyl-7,7,7-trifluoro-5-methyl-heptanoic acid;
(3S,5R)-3-Aminomethyl-8,8,8-trifluoro-5-methyl-octanoic acid;
(3S,5S)-3-Aminomethyl-5,6-dimethyl-heptanoic acid;
(3R,4R,5R)-3-Aminomethyl-4,5-dimethyl-heptanoic acid; and
(3R,4R,5R)-3-Aminomethyl-4,5-dimethyl-octanoic acid.

19. A pharmaceutical composition comprising a therapeutically effective amount of a compound according to claim 4 and a pharmaceutically acceptable carrier.

20. A pharmaceutical composition comprising a therapeutically effective amount of a compound according to claim 5 and a pharmaceutically acceptable carrier.

21. A pharmaceutical composition comprising a therapeutically effective amount of a compound according to claim 18 and a pharmaceutically acceptable carrier.

22. A method for treating epilepsy, faintness attacks, hypokinesia, cranial disorders, neurodegenerative disorders, depression, anxiety, panic, pain, neuropathological disorders, sleep disorders, IBS or gastric damage comprising administering a therapeutically effective amount of a compound according to claim 4 to a mammal in need of said treatment.

23. A method for treating epilepsy, faintness attacks, hypokinesia, cranial disorders, neurodegenerative disorders, depression, anxiety, panic, pain, neuropathological disorders, sleep disorders, IBS or gastric damage comprising administering a therapeutically effective amount of a compound according to claim 5 to a mammal in need of said treatment.

24. A method for treating epilepsy, faintness attacks, hypokinesia, cranial disorders, neurodegenerative disorders, depression, anxiety, panic, pain, neuropathological disorders, sleep disorders, IBS or gastric damage comprising administering a therapeutically effective amount of a compound according to claim 18 to a mammal in need of said treatment.

25. A method for treating epilepsy, anxiety, panic, pain, sleep disorders, IBS, or gastric damage comprising administering a therapeutically effective amount of a compound according to claim 1 to a mammal in need of said treatment.

26. A method for treating epilepsy, anxiety, panic, pain, sleep disorders, IBS, or gastric damage comprising administering a therapeutically effective amount of a compound according to claim 4 to a mammal in need of said treatment.

27. A method for treating epilepsy, anxiety, panic, pain, sleep disorders, IBS, or gastric damage comprising administering a therapeutically effective amount of a compound according to claim 5 to a mammal in need of said treatment.

28. A method for treating epilepsy, anxiety, panic, pain, sleep disorders, IBS, or gastric damage comprising administering a therapeutically effective amount of a compound according to claim 18 to a mammal in need of said treatment.

* * * * *